United States Patent
Maher et al.

(10) Patent No.: US 12,191,000 B2
(45) Date of Patent: Jan. 7, 2025

(54) SYSTEMS AND METHODS FOR CLASSIFYING PATIENTS WITH RESPECT TO MULTIPLE CANCER CLASSES

(71) Applicant: Grail, LLC, Menlo Park, CA (US)

(72) Inventors: M. Cyrus Maher, San Mateo, CA (US); Anton Valouev, Palo Alto, CA (US); Darya Filippova, Sunnyvale, CA (US); Virgil Nicula, Cupertino, CA (US); Karthik Jagadeesh, San Francisco, CA (US); Oliver Claude Venn, San Francisco, CA (US); Samuel S. Gross, Sunnyvale, CA (US); John F. Beausang, Menlo Park, CA (US); Robert Abe Paine Calef, Redwood City, CA (US)

(73) Assignee: GRAIL, INC., Menlo Park, CA (US)

( * ) Notice: Subject to any disclaimer, the term of this patent is extended or adjusted under 35 U.S.C. 154(b) by 64 days.

(21) Appl. No.: 18/151,197

(22) Filed: Jan. 6, 2023

(65) Prior Publication Data

US 2023/0170048 A1 Jun. 1, 2023

Related U.S. Application Data

(63) Continuation of application No. 16/709,537, filed on Dec. 10, 2019, now Pat. No. 11,581,062.

(Continued)

(51) Int. Cl.
  *G16B 30/00* (2019.01)
  *G06N 5/04* (2023.01)
  (Continued)

(52) U.S. Cl.
  CPC .............. *G16B 30/00* (2019.02); *G06N 5/04* (2013.01); *G06N 20/00* (2019.01); *G16B 20/20* (2019.02);
  (Continued)

(58) Field of Classification Search
  CPC ........ G16B 30/00; G16B 20/20; G16B 40/00; G16H 70/60; G16H 10/40; G16H 10/60;
  (Continued)

(56) References Cited

U.S. PATENT DOCUMENTS

| 8,642,349 B1 | 2/2014 | Yeatman et al. |
| 8,706,422 B2 | 4/2014 | Lo et al. |

(Continued)

FOREIGN PATENT DOCUMENTS

| CN | 106795562 A | 5/2017 |
| CN | 107430588 A | 12/2017 |

(Continued)

OTHER PUBLICATIONS

"International Search Report and Written Opinion" for International Application No. PCT/US2019/034994, Sep. 13, 2019, 28 pages.

(Continued)

*Primary Examiner* — Michael Tomaszewski
(74) *Attorney, Agent, or Firm* — Bookoff McAndrews, PLLC

(57) ABSTRACT

Technical solutions for classifying patients with respect to multiple cancer classes are provided. The classification can be done using cell-free whole genome sequencing information from subjects. A reference set of subjects is used to train classifiers to recognize genomic markers that distinguish such cancer classes. The classifier training includes dividing the reference genome into a set of non-overlapping bins, applying a dimensionality reduction method to obtain a feature set, and using the feature set to train classifiers. For subjects with unknown cancer class, the trained classifiers provide probabilities or likelihoods that the subject has a respective cancer class for each cancer in a set of cancer classes. The present disclosure thus describes methods to improve the screening and detection of cancer class from (Continued)

among several cancer classes. This serves to facilitate early and appropriate treatment for subjects afflicted with cancer.

27 Claims, 30 Drawing Sheets

Related U.S. Application Data

(60) Provisional application No. 62/777,693, filed on Dec. 10, 2018.

(51) Int. Cl.
*G06N 20/00* (2019.01)
*G16B 20/20* (2019.01)
*G16B 40/00* (2019.01)
*G16H 10/40* (2018.01)
*G16H 10/60* (2018.01)
*G16H 50/20* (2018.01)
*G16H 50/70* (2018.01)
*G16H 70/60* (2018.01)

(52) U.S. Cl.
CPC .............. *G16B 40/00* (2019.02); *G16H 10/40* (2018.01); *G16H 10/60* (2018.01); *G16H 50/20* (2018.01); *G16H 50/70* (2018.01); *G16H 70/60* (2018.01)

(58) Field of Classification Search
CPC ........ G16H 50/70; G16H 50/20; G06N 20/00; G06N 5/04
USPC ........................................................ 514/789
See application file for complete search history.

(56) References Cited

U.S. PATENT DOCUMENTS

| | | | |
|---|---|---|---|
| 9,260,745 B2 | 2/2016 | Rava et al. | |
| 9,373,059 B1 | 6/2016 | Heifets et al. | |
| 10,457,995 B2 | 10/2019 | Talasaz | |
| 2010/0112590 A1 | 5/2010 | Lo et al. | |
| 2010/0145894 A1 | 6/2010 | Semizarov et al. | |
| 2012/0053253 A1 | 3/2012 | Stone et al. | |
| 2013/0034546 A1 | 2/2013 | Rava et al. | |
| 2013/0325360 A1 | 12/2013 | Deciu et al. | |
| 2014/0066317 A1 | 3/2014 | Talasaz | |
| 2014/0080715 A1 | 3/2014 | Lo et al. | |
| 2014/0100121 A1 | 4/2014 | Lo et al. | |
| 2014/0242588 A1 | 8/2014 | Boom et al. | |
| 2014/0371078 A1 | 12/2014 | Abdueva | |
| 2015/0102216 A1* | 4/2015 | Roder .................. | G06V 20/698 250/281 |
| 2016/0002739 A1 | 1/2016 | Schütz et al. | |
| 2016/0232290 A1 | 8/2016 | Rava et al. | |
| 2016/0251704 A1 | 9/2016 | Talasaz et al. | |
| 2016/0364522 A1 | 12/2016 | Frey et al. | |
| 2017/0107576 A1 | 4/2017 | Babiarz et al. | |
| 2017/0121767 A1 | 5/2017 | Dor et al. | |
| 2017/0220735 A1 | 8/2017 | Duenwald et al. | |
| 2017/0240973 A1 | 8/2017 | Eltoukhy et al. | |
| 2017/0270245 A1* | 9/2017 | van Rooyen .......... | G16B 50/40 |
| 2017/0329893 A1 | 11/2017 | Julio et al. | |
| 2017/0342477 A1 | 11/2017 | Jensen et al. | |
| 2017/0342500 A1 | 11/2017 | Marquard et al. | |
| 2017/0362638 A1 | 12/2017 | Chudova et al. | |
| 2018/0046851 A1 | 2/2018 | Kienzle et al. | |
| 2018/0144261 A1 | 5/2018 | Wnuk et al. | |
| 2018/0148777 A1 | 5/2018 | Kirkizlar et al. | |
| 2018/0173845 A1 | 6/2018 | Sigurjonsson et al. | |
| 2019/0106737 A1 | 4/2019 | Underhill | |
| 2019/0164627 A1 | 5/2019 | Blocker et al. | |
| 2019/0287646 A1 | 9/2019 | Hubbell | |
| 2019/0287649 A1 | 9/2019 | Filippova et al. | |
| 2019/0287652 A1 | 9/2019 | Gross et al. | |
| 2019/0316209 A1 | 10/2019 | Hubbell et al. | |
| 2020/0005901 A1* | 1/2020 | Cohen .................. | G06N 20/20 |
| 2020/0219587 A1 | 7/2020 | Hubbell | |
| 2020/0294624 A1 | 9/2020 | Filippova et al. | |
| 2020/0365229 A1 | 11/2020 | Fields et al. | |
| 2020/0372296 A1 | 11/2020 | Maher | |
| 2021/0324477 A1* | 10/2021 | Xiang .................. | C12Q 1/708 |

FOREIGN PATENT DOCUMENTS

| | | |
|---|---|---|
| CN | 108064314 A | 5/2018 |
| WO | 2010037001 A2 | 4/2010 |
| WO | 2010051318 A2 | 5/2010 |
| WO | 2011127136 A1 | 10/2011 |
| WO | 2012071621 A1 | 6/2012 |
| WO | 2013052907 A2 | 4/2013 |
| WO | 2014149134 A2 | 9/2014 |
| WO | 2016094853 A1 | 6/2016 |
| WO | 2017062382 A1 | 4/2017 |
| WO | 2017161175 A1 | 9/2017 |
| WO | 2017212428 A1 | 12/2017 |
| WO | 2017181202 A3 | 1/2018 |
| WO | 2018009723 A1 | 1/2018 |
| WO | 2018022890 A1 | 2/2018 |
| WO | 2018022906 A1 | 2/2018 |
| WO | 2018031929 A1 | 2/2018 |
| WO | 2019084559 A1 | 5/2019 |
| WO | 2019232435 A1 | 12/2019 |
| WO | 2021119471 A1 | 6/2021 |

OTHER PUBLICATIONS

"International Search Report and Written Opinion," for International Application No. PCT/US2019/22139, Jul. 11, 2019, 18 pages.
"Patent Application," U.S. Appl. No. 62/679,347, entitled "Models for Targeted Sequencing", filed Jun. 1, 2018.
"Patent Application," U.S. Appl. No. 62/818,013, entitled Systems and Methods for Enriching for Cancer-Derived Fragments Using Fragment Size, filed Mar. 13, 2019, Mar. 13, 2019.
"Patent Application," U.S. Appl. No. 62/827,682, entitled "Systems and Methods for Using Fragment Lengths as a Predictor of Cancer," filed Apr. 1, 2019, Apr. 10, 2019.
"Patent Application," U.S. Appl. No. 62/851,486, entitled "Systems and Methods for Determining Whether a Subject Has a Cancer Condition Using Transfer Learning," filed May 22, 2019, May 22, 2019.
"Patent Application," U.S. Appl. No. 62/847,223, entitled "Model-Based Featurization and Classification," filed May 13, 2019, May 13, 2019.
Aengus S. O'Marcaigh, et al., "Estimating the Predictive Value of a Diagnostic Test: How to Prevent Misleading or Confusing Results, Clinical Pediatrics", vol. 32, Issue 8, First Published Aug. 1, 1993, 7 pages.
Alan Agresti, "Building and Applying Logistic Regression Models", An Introduction to Categorical Data Analysis, Second Edition, Aug. 7, 2006, pp. 137-172.
Alan Agresti, "Introduction to Categorical Data Analysis; Chapter 5: Logist Analysis", Wiley-Interscience, A John Wiley & Sons Inc., Publication, Copyright 1996, 44 pages.
Alan H. Lipkus, "A proof of the triangle inequality for the Tanimoto distance", Journal of Mathematical Chemistry, vol. 26, Published Oct. 1, 1999, pp. 263-265.
Alkan et al., "Personalized copy number and segmental duplication maps using next-generation sequencing," 2009, Nat Genet 41:1061-7.
Alkes L. Price, et al., "Principal components analysis corrects for stratification in genome-wide association studies", vol. 38 No. 8, Aug. 2006, Nature Genetics, pp. 904-909.
Antonio Fabregat et al., "The Reactome Pathway Knowledgebase", Nucleic Acids Research, 2018, vol. 46, Database Issue D649-D655, Published online Nov. 14, 2017, 7 pp.
Benjamini et al., "Summaraizing and Correcting the GC Content Bias in High-Throughput Sequencing," 2012, Nucleic Acids Research 40(10): e72.

(56) References Cited

OTHER PUBLICATIONS

Bernhard E. Boser et al., "A Training Algorithm for Optimal Margin Classifiers", Proceedings of the fifth annual workshop on Computational learning theory, Jul. 1992, pp. 144-152.
Boeva et al., "Control-free calling of copy number alterations indeep-sequencing data using GC-content normalization", 2011, Bioinformatics 27(2), p. 268-9.
Breiman, "Random Forests—Random Features", Technical Report 567, Sep. 1999, Statistics Department, U.C. Berkeley, pp. 1-29.
Casadio et al., 2013, "Urine cell-free DNA integrity as a marker for early bladder cancer diagnosis: preliminary data," Urol Oncol. 31(8):1744-1750.
Chan et al., 2003, "Clinical Sciences Reviews Committee of the Association of ClinicalBiochemists Cell-free nucleic acids in plasma, serum and urine: a new tool in molecular diagnosis," Ann Clin Biochem. 40(Pt 2):122-130.
Changhong Shan, U.S. Appl. No. 62/642,506, filed Mar. 13, 2018, "Single Radio Voice Call Continuity (SRVCC) Handover and Return to Next Generation Radio Access Network (NG-RAN) After SRVCC" (54 pages).
Christof Angermueller et al., "DeepCpG: accurate prediction of single-cell DNA methylation states using deep learning", Genome Biology, 18:67, Apr. 11, 2017, pp. 1-13.
David J. Rogers et al., "A Computer Program for Classifying Plants", vol. 132, Issue 3434, Oct. 21, 1960.
De Mattos-Arruda and Caldas, 2016, "Cell-free circulating tumour DNA as a liquid biopsy in breast cancer," Mol Oncol. 10(3):464-474.
Dingdong Zhang et al., "A novel method to quantify local CpG methylation density by regional methylation elongation assay on microarray", Published Jan. 31, 2008, BMC Genomics 9, Article No. 59, BioMed Central, 9 pp.
Duda, "Support Vector Machines", Pattern Classification (Chapter 5—Linear Discriminant Functions), 2001, pp. 259 and 262-265.
Erickson, "Somatic gene mutation and human disease other than cancer: An update," Mutat Res 705(2), 2010, 96-106.
Erickson, et al., "Somatic gene mutation and human disease other than cancer," Mutat Res 543(2), 2003, 125-136.
Frenel et al., 2015, "Serial next-generation sequencing of circulating cell-free DNA evaluating tumor clone response to molecularly targeted drug administration," Clin Cancer Res.21(20):4586-4596.
Fushun Chen et al., "Conflicts of CpG density and DNA methylation are proximally and distally involved in gene regulation in human and mouse tissues", Epigenetics, ISSN: 1559-2294 (Print) 1559-2308 (Online), 2018, vol. 13, No. 7, pp. 721-741.
G.R. Oxnard et al., "Simultaneous multi-cancer detection and tissue of origin (TOO) localization using targeted bisulfite sequencing of plasma cell-free DNA (cfDNA)", New Diagnostic Tools, ESMO, vol. 30, Supplement 5, Oct. 2019, 1 pp.
Garrett Jenkinson et al., "Potential energy landscapes identify the information-theoretic nature of the epigenome", vol. 49, No. 5, May 2017, Nature Genetics, pp. 719-732.
Goessl et al., 2000, "Fluorescent methylation-specific polymerase chain reaction for DNA-based detection of prostate cancer in bodily fluids," Cancer Res. 60(21):5941-5945.
Gold, 1996, "Softmax to Softassign: Neural Network Algorithms for Combinatorial Optimization," Journal of Artificial Neural Networks 2, 381-399.
Gregory Nuel et al., "Exact distribution of a pattern in a set of random sequences generated by a Markov source: applications to biological data", Algorithms for Molecular Biology 5, Article No. 15, (2010), pp. 1-18.
Hao et al., 2014, "Circulating cell-free DNA in serum as a biomarker for diagnosis and prognostic prediction of colorectal cancer," Br J Cancer 111(8):1482-1489.
Heitzer et al., 2013, "Establishment of tumorspecific copy No. alterations from plasma DNA of patients with cancer," Int J Cancer. 133(2):346-356).
Heitzer et al., 2015, "Circulating tumor DNA as a liquid biopsy for cancer," Clin Chem. 61(1):112-123.

Heng Li et al., "Mapping short DNA sequencing reads and calling variants using mapping quality scores", Genome Research, ISSN 1088-9051/08, accepted in revised form Aug. 13, 2008, pp. 1851-1858.
Hoadley, et al., "Multi-platform analysis of 12 cancer types reveals molecular classification within and across tissues-of-origin," Cell 158(4), 2014, 929-944.
Hugo Larochelle et al., "Exploring Strategies for Training Deep Neural Networks", Journal of Machine Learning Research 1 (2009), pp. 1-40.
Huihuan Qian et al., "Intelligent Surveillance Systems", International Series on Intelligent Systems, Control and Automation: Science and Engineering, vol. 51, © Springer Science+Business Media B.V. 2011, 187 pp.
I. T. Jolliffe, "Principal Component Analysis", Springer, New York © 2002, 518 pages.
International Search Report and Written Opinion mailed Mar. 9, 2021 in International Application No. PCT/US2020/064577 (13 pages).
Jihoon Yang et al., "DistAI: An inter-pattern distance-based constructive learning algorithm", Intelligent Data Analysis, vol. 3, No. 1, Published Jan. 1, 1999, pp. 55-73.
Karen Simonyan et al., "Very Deep Convolutional Networks for Large-Scale Image Recognition", Published as a conference paper at ICLR 2015, Apr. 10, 2015, 14 pp.
Kim et al., 2014, "Circulating cell-free DNA as a promising biomarker in patients with gastriccancer: diagnostic validity and significant reduction of cfDNA after surgical resection," Ann Surg Treat Res 86(3):136-1420.
Laure Sorber et al., "A Comparison of Cell-Free DNA Isolation Kits: Isolation and Quantification of Cell-Free DNA in Plasma", The Journal of Molecular Diagnostics, vol. 19, No. 1, Jan. 2017, pp. 162-168.
Levandowsky et al., "Distance between Sets", Nature vol. 234, Nov. 5, 1971, pp. 34-35.
Iu et al., 2019, "Bisulfite-free direct detection of 5-methylcytosine and 5-hydroxymethylcytosine at base resolution," Nature Biotechnology 37, pp. 424-429.
Lo et al., 2010, "Maternal plasma DNA sequencing reveals the genome-wide genetic and mutational profile of the jetus," Sci Transl Med. 2(61):61ra91.
Margaret Sullivan Pepe, et al., "Limitations of the Odds Ration in Gauging the Performance of a Diagnostic, Prognostic, or Screening Marker", American Journal of Epidemiology, American Journal of Epidemiology, vol. 159, Issue 9, May 1, 2004, pp. 882-890.
Miller et al., "ReadDepth: A Parallel R Package for Detecting Copy Number Alterations from Short Sequencing Reads", 2011, PLoS ONE 6(1), p. e16327.
Minoru Kanehisa et al., "KEGG: Kyoto Encyclopedia of Genes and Genomes", Nucleic Acids Research, 2000, vol. 28, No. 1, pp. 27-30.
Mohamad H. Hassoun, "Fundamentals of Artificial Neural Networks", Adaptive Multilayer Nerual Networks I, pp. 197-283.
Nancy R. Cook, "Use and Misuse of the Receiver Operating Characteristic Curve in Risk Prediction", vol. 115, Issue 7, Feb. 20, 2007, pp. 928-935.
Nello Cristianini et al., "An Introduction to Support Vector Machines and other kernel-based learning methods", Support Vector Machines, © Cambridge University Press 2000, pp. 93-124.
Ning Yu et al., "GaussianCpG: a Gaussian model for detection of CpG island in human genome sequences", The Author(s) BMC Genomics 2017, 18(Suppl 4):392, 9 pp.
Pan Du et al., "Comparison of Beta-value and M-value methods for quantifying methylation levels by microarray analysis", Du et al. BMC Bioinformatics 2010, 11:587, 9 pp.
Pang-Ning Tan et al., "Instructor's Solution Manual", © 2006 Pearson Addison-Wesley, 169 pp.
Pascal Vincent et al., "Stacked Denoising Autoencoders: Learning Useful Representations in a Deep Network with a Local Denoising Criterion", Journal of Machine Learning Research, 11(110), © 2010, pp. 3371-3408.
Paul Jaccard, "The Distribution of the Flora in the Alpine Zone", The New Phytologist, vol. 11, No. 2, Feb. 29, 1912, pp. 37-50.

(56) References Cited

OTHER PUBLICATIONS

Raptis et al., 1980, "Quantitation and characterization of plasma DNA in normals and patients with systemic lupus erythematosus," J Clin Invest. 66(6):1391-1399.

Richard O. Duda et al., "Pattern Classification and Scene Analysis", © 1973 John Wiley & Sons, Inc., 496 pp.

Richard O. Duda et al., "Pattern Classification and Scene Analysis", John Wiley & Sons, Inc., New York, A Wiley-Interscience Publication, Copyright 1973, 496 pages.

Ryan Moulton et al., "Maximally Consistent Sampling and the Jaccard Index of Probability Distributions", Sep. 11, 2018, 11 pp.

Ryan Poplin et al., "A universal SNP and small-indel variant caller using deep neural networks", Nature Biotechnology, vol. 36, No. 10, Oct. 2018, 9 pp.

Salvi et al., 2016, "Cell-free DNA as a diagnostic marker for cancer: current insights," Onco Targets Ther. 9:6549-6559.

Shao et al., 2015 "Quantitative analysis of cell-free DNA in ovarian cancer," Oncol Lett 10(6):3478-3482).

Shapiro et al., 1983, "Determination of circulating DNA levels in patients with benign or malignant gastrointestinal disease," Cancer. 51(11):2116-2120.

Siegel et al., 2015, "Cancer statistics," CA Cancer J Clin. 65(1):5-29.

Sozzi et al., "Quantification of free circulating DNA as a diagnostic marker in lung cancer," J Clin Oncol. 21(21):3902-3908.

Steven Kothen-Hill et al., "Deep Learning Mutation Prediction Enables Early Stage Lung Cancer Detection in Liquid Biopsy", Workshop track—ICLR 2018, 24 pages.

Stroun et al., 1989, "Neoplastic characteristics of the DNA found in the plasma of cancer patients," Oncology 46(5):318-322.

Sven Kosub, "A note on the triangle inequality for the Jaccard distance", Dec. 9, 2016, pp. 1-5.

Swanton, et al., "Phylogenetic ctDNA analysis depicts early stage lung cancer evolution", Nature. Apr. 26, 2017, Author manuscript; available in PMC Feb. 14, 2018; 545(7655), 446-451, 47 pages.

T. Hastie et al., "Additive Models, Trees, and Related Methods", The Elements of Statistical Learning, Second Edition, © Springer Science+Business Media, LLC 2009, pp. 295-336.

T.T. Tanimoto, "An Elementary Mathematical Theory of Classification and Prediction", Nov. 17, 1958, 11 pp.

Terrence S. Furey et al., "Support vector machine classification and validation of cancer tissue samples using microarray expression data", Bioinformatics, vol. 16, No. 10, 2000, pp. 906-914.

Terry et al., 2016, "A prospective evaluation of early detection biomarkers for ovarian cancer in the European EPIC cohort," Clin Cancer Res. Apr. 8, 2016; Epub.

U.S. Appl. No. 62/642,507, filed Mar. 13, 2018, entitled, "Identifying Copy Number Aberrations" (67 pages).

Vladimir N. Vapnik, "Statistical Learning Theory", © 1998 by John Wiley & Sons Inc., 28 pp.

Yoon et al., "Sensitive and Accurate Detection of Copy Number Variants Using Read Depth of Coverage", 2009, Genome Research 19(9):1586.

Yuchen Yuan et al., "DeepGene: an advanced cancer type classifier based on deep learning and somatic point mutations", Dec. 2016, BMC Bioinformatics 17(Suppl 17):476, 15 pages.

Zhang et al., 2015, "Tumor markers CA19-9, CA242 and CEA in the diagnosis of pancreatic cancer: a meta-analysis," Int J Clin Exp Med. 8(7):11683-11691.

Zhao, et al., "Detection of fetal subchromosomal abnormalities by sequencing circulating cell-free DNA from maternal plasma", Clinical Chemistry, vol. 61, Issue 4, Apr. 1, 2015, pp. 608-616.

Zonta et al., 2015, "Assessment of DNA integrity, applications for cancer research," Adv Clin Chem 70:197-246.

Hudecova, I., & Chiu, R. W. (2017). Non-invasive prenatal diagnosis of thalassemias using maternal plasma cell free DNA. Best practice & research. Clinical obstetrics & gynaecology, 39, 63-73. (Year: 2017).

Smedley, D., Schubach, M., Jacobsen, J. O. B., Kohler, S., Zemotjel, T., Spielmann, M., Jager, M., Hochheiser, H., Washington, N.L., McMurry, J. A., Haendel, M.A., Mungall, C.J., Lewis, S.E., Groza, T., Valentini, G., Robinson, P.N. (2016). A Whole-Genome Analysis Framework for Effective Identification of Pathogenic Regulatory Variants in Mendelian Disease. American journal of human genetics, 99(3), 595-606. (Year: 2016).

Ulz, P., Thallinger, G. G., Auer, M., Graf, R., Kashofer, K., Jahn, S. W., Abete, L., Pristauz, G., Petru, E., Geigl, J. B., Heitzer, E., & Speicher, M. R. (2016). Inferring expressed genes by whole-genome sequencing of plasma DNA. Nature genetics, 48(10), 1273-1278. (Year: 2016).

Jaccard, Paul, Comparative Study of the Floral distribution in a portion of the Als and the Jura, Bull.Soc.Vaud.Sci Nat. XXXVII, 142, pp. 547-579, 1901, English translation.

Jaccard, Étude comparative de la distribution florale dans une portion des Alpes et des Jura, 1901, pp. 547-579, Bulletin de la Société vaudoise des sciences naturelles, 37.

\* cited by examiner

| Tissue Stage | Breast | Colorectal | Esophageal | Head/Neck | Lung | Lymphoma | Ovarian | Pancreas | Prostate | Renal | Uterine | Non-cancer |
|---|---|---|---|---|---|---|---|---|---|---|---|---|
| I | 0.04 (6/165) | 0.00 (0/5) | 0.00 (0/2) | 0.00 (0/2) | 0.09 (2/23) | 0.00 (0/5) | 0.00 (0/2) | 0.00 (0/2) | 0.00 (0/17) | 0.00 (0/15) | 0.00 (0/25) | |
| II | 0.24 (30/125) | 0.25 (2/8) | 0.00 (0/6) | 0.00 (0/3) | 0.07 (1/14) | 0.33 (2/6) | 0.00 (0/1) | 0.00 (0/6) | 0.02 (1/46) | 0.00 (0/2) | 0.00 (0/1) | |
| III | 0.30 (15/50) | 0.31 (5/16) | 0.11 (1/9) | 0.40 (2/5) | 0.28 (11/39) | 0.00 (0/5) | 0.22 (2/9) | 0.00 (0/2) | 0.00 (0/3) | 0.00 (0/3) | | |
| IV | 0.33 (2/6) | 0.68 (13/19) | 0.40 (2/5) | 0.30 (3/10) | 0.49 (22/45) | 0.80 (4/5) | 0.57 (4/7) | 0.35 (6/17) | 0.00 (0/4) | 0.00 (0/5) | 0.00 (0/1) | |
| Non-cancer | | | | | | | | | | | | 0.94 (535/572) |

Figure 6

| Tissue Stage | Breast | Colorectal | Esophageal | Head/Neck | Lung | Lymphoma | Ovarian | Pancreas | Prostate | Renal | Uterine | Non-cancer |
|---|---|---|---|---|---|---|---|---|---|---|---|---|
| I | 0.00 (0/1) | | | | 1.00 (1/1) | | | | | | | |
| II | 0.75 (9/12) | | | 0.00 (0/1) | 0.00 (0/1) | 0.40 (2/5) | | | | | | |
| III | 0.53 (8/15) | 0.75 (3/4) | 0.25 (1/4) | 1.00 (1/1) | 0.38 (8/21) | 0.00 (0/2) | 0.40 (2/5) | | | | | |
| IV | 0.00 (0/3) | 0.71 (12/17) | 0.50 (2/4) | 0.25 (1/4) | 0.59 (17/29) | 0.80 (4/5) | 0.80 (4/5) | 0.50 (6/12) | 0.00 (0/3) | 0.00 (0/4) | 0.00 (0/1) | |
| Non-cancer | | | | | | | | | | | | 0.00 (0/3) |

Figure 8

SYSTEMS AND METHODS FOR CLASSIFYING PATIENTS WITH RESPECT TO MULTIPLE CANCER CLASSES

CROSS-REFERENCE TO RELATED PATENT APPLICATIONS

This application is a continuation of and claims the benefit of priority to U.S. patent application Ser. No. 16/709,537, filed on Dec. 10, 2019, which claims the benefit of priority to U.S. Provisional Patent Application No. 62/777,693 entitled "SYSTEMS AND METHODS FOR CLASSIFYING PATIENTS WITH RESPECT TO MULTIPLE CANCER CLASSES," filed Dec. 10, 2018, all of which are incorporated herein by reference in their entireties.

TECHNICAL FIELD

This specification describes using nucleic acids, in particular cell-free nucleic acid of a subject, to classify a disease state or condition of the subject.

BACKGROUND

The increasing knowledge of the molecular basis for cancer and the rapid development of next generation sequencing techniques are advancing the study of early molecular alterations involved in cancer development in body fluids. Specific genetic and epigenetic alterations associated with such cancer development are found in plasma, serum, and urine cell-free DNA (cfDNA). Such alterations could potentially be used as diagnostic biomarkers for several classes of cancers. See Salvi et al., 2016, "Cell-free DNA as a diagnostic marker for cancer: current insights," Onco Targets Ther. 9:6549-6559.

With a total of over 1.6 million new cases each year in the United States as of 2017, cancer represents a prominent worldwide public health problem. See, Siegel et al., 2017, "Cancer statistics," CA Cancer J Clin. 67 (1): 7-30. Screening programs and early diagnosis have an important impact in improving disease-free survival and reducing mortality in cancer patients. As noninvasive approaches for early diagnosis foster patient compliance, they can be included in screening programs.

Noninvasive serum-based biomarkers used in clinical practice include carcinoma antigen 125 (CA 125), carcinoembryonic antigen, carbohydrate antigen 19-9 (CA19-9), and prostate-specific antigen (PSA) for the detection of ovarian, colon, and prostate cancers, respectively. See, Terry et al., 2016, "A prospective evaluation of early detection biomarkers for ovarian cancer in the European EPIC cohort," Clin Cancer Res. 2016 Apr. 8; Epub and Zhang et al., "Tumor markers CA19-9, CA242 and CEA in the diagnosis of pancreatic cancer: a meta-analysis," Int J Clin Exp Med. 2015; 8 (7): 11683-11691.

These biomarkers generally have low specificity (high number of false-positive results). Thus, new noninvasive biomarkers are actively being sought. The increasing knowledge of the molecular pathogenesis of cancer and the rapid development of new molecular techniques such as next generation nucleic acid sequencing techniques is promoting the study of early molecular alterations in body fluids.

Cell-free DNA (cfDNA) can be found in serum, plasma, urine, and other body fluids (Chan et al., "Clinical Sciences Reviews Committee of the Association of Clinical Biochemists Cell-free nucleic acids in plasma, serum and urine: a new tool in molecular diagnosis," Ann Clin Biochem. 2003; 40 (Pt 2): 122-130) representing a "liquid biopsy," which is a circulating picture of a specific disease. See, De Mattos-Arruda and Caldas, 2016, "Cell-free circulating tumour DNA as a liquid biopsy in breast cancer," Mol Oncol. 2016; 10 (3): 464-474. This represents a potential, non-invasive method of screening for a variety of cancers.

The existence of cfDNA was demonstrated by Mandel and Metais (Mandel and Metais), "P. Les acides nucleiques du plasma sanguin chez l'homme [The nucleic acids in blood plasma in humans]," C R Seances Soc Biol Fil. 1948; 142 (3-4): 241-243). cfDNA originates from necrotic or apoptotic cells, and it is generally released by all types of cells. Stroun et al further showed that specific cancer alterations could be found in the cfDNA of patients. See, Stroun et al., "Neoplastic characteristics of the DNA found in the plasma of cancer patients," Oncology. 1989; 46 (5): 318-322). A number of subsequent articles confirmed that cfDNA contains specific tumor-related alterations, such as mutations, methylation, and copy number variations (CNVs), thus confirming the existence of circulating tumor DNA (ctDNA). See, Goessl et al., "Fluorescent methylation-specific polymerase chain reaction for DNA-based detection of prostate cancer in bodily fluids," Cancer Res. 2000; 60 (21): 5941-5945 and Frenel et al., 2015, "Serial next-generation sequencing of circulating cell-free DNA evaluating tumor clone response to molecularly targeted drug administration. Clin Cancer Res. 21 (20): 4586-4596.

cfDNA in plasma or serum is well characterized, while urine cfDNA (ucfDNA) has been traditionally less characterized. However, recent studies demonstrated that ucfDNA could also be a promising source of biomarkers. See, Casadio et al., 2013, "Urine cell-free DNA integrity as a marker for early bladder cancer diagnosis: preliminary data," Urol Oncol. 2013; 31 (8): 1744-1750.

In blood, apoptosis is a frequent event that determines the amount of cfDNA. In cancer patients, however, the amount of cfDNA seems to be also influenced by necrosis. See Hao et al., "Circulating cell-free DNA in serum as a biomarker for diagnosis and prognostic prediction of colorectal cancer," Br J Cancer. 2014; 111 (8): 1482-1489 and Zonta et al., "Assessment of DNA integrity, applications for cancer research," Adv Clin Chem. 2015; 70:197-246. Since apoptosis seems to be the main release mechanism, circulating cfDNA has a size distribution that reveals an enrichment in short fragments of about 167 bp, (see, Heitzer et al., 2015, "Circulating tumor DNA as a liquid biopsy for cancer," Clin Chem. 61 (1): 112-123 and Lo et al., 2010, "Maternal plasma DNA sequencing reveals the genome-wide genetic and mutational profile of the fetus," Sci Transl Med. 2 (61): 61ra91) corresponding to nucleosomes generated by apoptotic cells.

The amount of circulating cfDNA in serum and plasma seems to be significantly higher in patients with tumors than in healthy controls, especially in those with advanced-stage tumors than in early-stage tumors. See, Sozzi et al., 2003 "Quantification of free circulating DNA as a diagnostic marker in lung cancer," J Clin Oncol. 21 (21): 3902-3908, Kim et al., 2014, "Circulating cell-free DNA as a promising biomarker in patients with gastric cancer: diagnostic validity and significant reduction of cfDNA after surgical resection," Ann Surg Treat Res. 2014; 86 (3): 136-142; and Shao et al. 2015 "Quantitative analysis of cell-free DNA in ovarian cancer," Oncol Lett. 2015; 10 (6): 3478-3482). The variability of the amount of circulating cfDNA is higher in cancer patients than in healthy individuals, (Heitzer et al., 2013, "Establishment of tumor-specific copy number alterations from plasma DNA of patients with cancer," Int J Cancer. 133 (2): 346-356) and the amount of circulating cfDNA is influenced by several physiological and pathological conditions, including proinflammatory diseases. See, Raptis and Menard, 1980, "Quantitation and characterization of plasma DNA in normals and patients with systemic lupus erythematosus," J Clin Invest. 66 (6): 1391-1399, and Shapiro et al., 1983, "Determination of circulating DNA levels in patients with benign or malignant gastrointestinal disease," Cancer. 51 (11): 2116-2120.

Given the promise of circulating cfDNA, as well as other forms of genotypic data, as a diagnostic indicator, ways of processing such data in order to derive accurate classifiers for cancer diagnosis are needed in the art.

SUMMARY

The present disclosure addresses the shortcomings identified in the background by providing robust techniques for classifying a cancer condition for a species based on cfDNA. The combination of methylation data with whole genome sequencing data provides additional diagnostic power beyond previous screening methods.

In one aspect, all or a portion of a reference genome of the species is represented by a plurality of bins. Each bin in the plurality of bins represents a different and non-overlapping portion of the reference genome. There is obtained, for each respective reference subject in a first plurality of reference subjects, (i) a cancer class of the respective reference subject and (ii) a sequencing construct for the respective reference subject that includes a first bin count for each respective bin in the plurality of bins. Each respective first bin count is representative of a number of nucleic acid fragments measured from nucleic acids in a biological sample obtained from the reference subject. Each bin maps onto a different and non-overlapping portion of the reference genome of the species represented by the bin corresponding to the respective first bin. For each respective cancer class in the plurality of cancer classes, the first plurality of reference subjects includes at least one subject that has the respective cancer class. There is obtained a feature set by collectively subjecting the first bin count, of each bin in the plurality of bins for each reference subject in the plurality of reference subjects, to a dimensionality reduction method. The feature set consists of a number of features that is fewer than the number of bins in the plurality of bins. The dimensionality reduction method yields a value training set comprising a value for each feature in the feature set for each reference subject in the plurality of reference subjects. There is obtained a trained first classifier by using the value training set as a collective input to an untrained first classifier, in conjunction with the cancer class of each respective reference subject in the first plurality of reference subjects as ground truth, to train the untrained first classifier on cancer class. The trained first classifier is used to classify the test subject to a cancer class in the plurality of cancer classes using counts of nucleic acid fragments in a biological sample obtained from the test subject.

Other embodiments are directed to systems, portable consumer devices, and computer readable media associated with methods described herein.

As disclosed herein, any embodiment disclosed herein when applicable can be applied to any aspect.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications herein are incorporated by reference in their entireties. In the event of a conflict between a term herein and a term in an incorporated reference, the term herein controls.

BRIEF DESCRIPTION OF THE DRAWINGS

The implementations disclosed herein are illustrated by way of example, and not by way of limitation, in the figures of the accompanying drawings. Like reference numerals refer to corresponding parts throughout the several views of the drawings.

FIG. 6 is a tabular representation of the data of FIG. 5.

FIG. 8 is a tabular representation of the data of FIG. 7.

DETAILED DESCRIPTION

Figure 1:
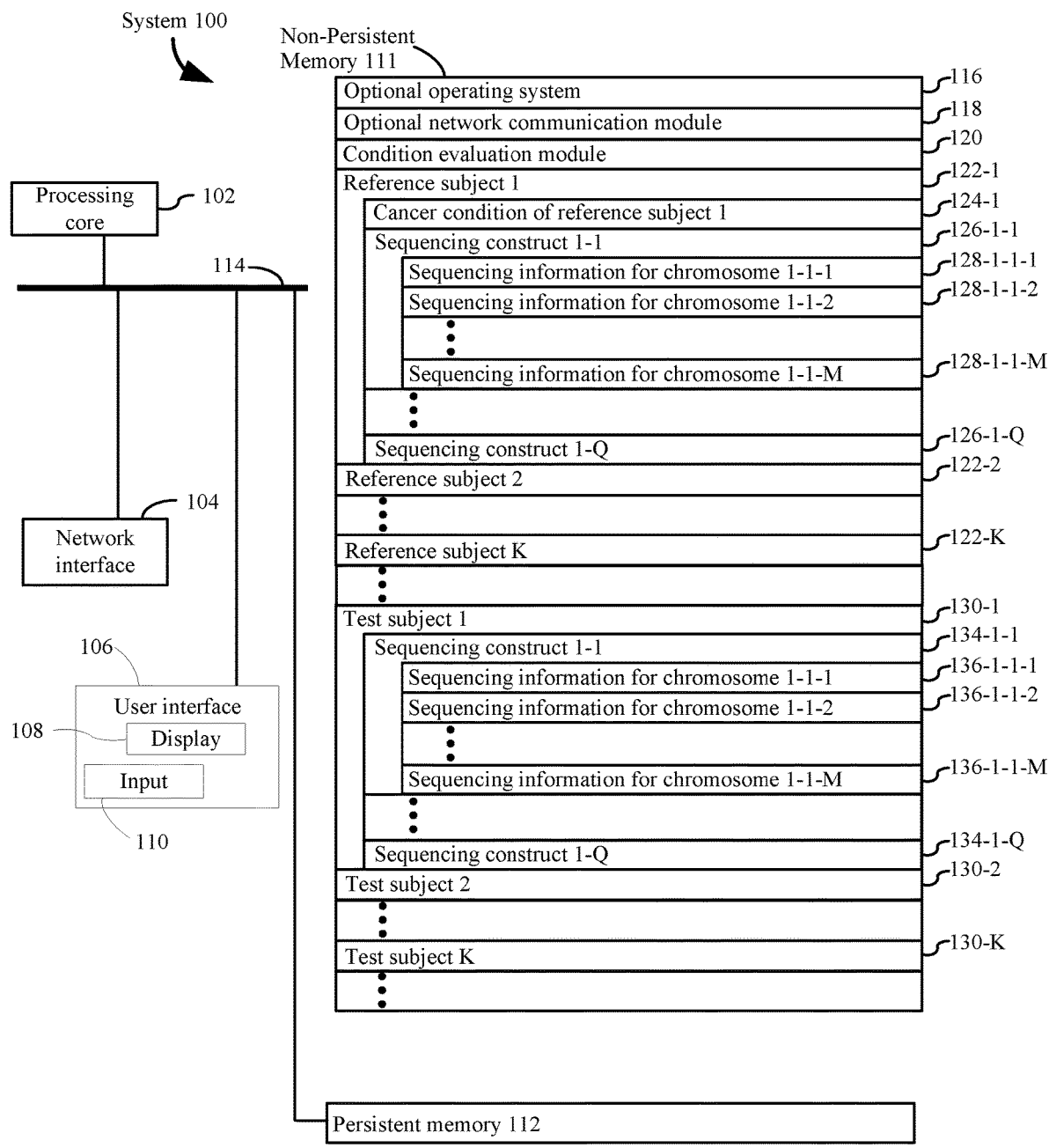
FIG. 1 illustrates an example block diagram illustrating a computing device in accordance with some embodiments of the present disclosure.

Reference will now be made in detail to embodiments, examples of which are illustrated in the accompanying drawings. In the following detailed description, numerous specific details are set forth in order to provide a thorough understanding of the present disclosure. However, it will be apparent to one of ordinary skill in the art that the present disclosure may be practiced without these specific details. In other instances, well-known methods, procedures, components, circuits, and networks have not been described in detail so as not to unnecessarily obscure aspects of the embodiments.

The implementations described herein provide various technical solutions for classifying subjects to cancer classes. Cell-free whole genome sequencing (WGS) is performed for each subject. A reference set of subjects is used to train a classifier to recognize genomic markers (e.g. signatures) that distinguish cancer classes. The classifier training apportions the reference genome into a set of non-overlapping bins, applies a dimensionality reduction method to the binned data to obtain a feature set, and applies the feature set to untrained classifiers to obtain trained classifiers. Sequencing data from a subject with unknown cancer class are then provided as input to the trained classifier. The trained classifier then provides the probability that the subject has certain cancers in a set of cancer classes. The disclosed methods serve to improve screening and detection of multiple cancer classes and facilitates early and appropriate treatment.

Definitions

As used herein, the term "about" or "approximately" mean within an acceptable error range for the particular value as determined by one of ordinary skill in the art, which depends in part on how the value is measured or determined, e.g., the limitations of the measurement system. For example, in some embodiments "about" mean within 1 or more than 1 standard deviation, per the practice in the art. In some embodiments, "about" means a range of ±20%, ±10%, ±5%, or ±1% of a given value. In some embodiments, the term "about" or "approximately" means within an order of magnitude, within 5-fold, or within 2-fold, of a value. Where particular values are described in the application and claims, unless otherwise stated the term "about" meaning within an acceptable error range for the particular value should be assumed. The term "about" can have the meaning as commonly understood by one of ordinary skill in the art. In some embodiments, the term "about" refers to ±10%. In some embodiments, the term "about" refers to ±5%.

As used herein, the term "assay" refers to a technique for determining a property of a substance, e.g., a nucleic acid, a protein, a cell, a tissue, or an organ. An assay (e.g., a first assay or a second assay) can comprise a technique for determining the copy number variation of nucleic acids in a sample, the methylation status of nucleic acids in a sample, the fragment size distribution of nucleic acids in a sample, the mutational status of nucleic acids in a sample, or the fragmentation pattern of nucleic acids in a sample. Any assay known to a person having ordinary skill in the art can be used to detect any of the properties of nucleic acids mentioned herein. Properties of a nucleic acids can include a sequence, genomic identity, copy number, methylation state at one or more nucleotide positions, size of the nucleic acid, presence or absence of a mutation in the nucleic acid at one or more nucleotide positions, and pattern of fragmentation of a nucleic acid (e.g., the nucleotide position(s) at which a nucleic acid fragments). An assay or method can have a particular sensitivity and/or specificity, and their relative usefulness as a diagnostic tool can be measured using ROC-AUC statistics.

As disclosed herein, the term "subject" refers to any living or non-living organism, including but not limited to a human (e.g., a male human, female human, fetus, pregnant female, child, or the like), a non-human animal, a plant, a bacterium, a fungus or a protist. Any human or non-human animal can serve as a subject, including but not limited to mammal, reptile, avian, amphibian, fish, ungulate, ruminant, bovine (e.g., cattle), equine (e.g., horse), caprine and ovine (e.g., sheep, goat), swine (e.g., pig), camelid (e.g., camel, llama, alpaca), monkey, ape (e.g., gorilla, chimpanzee), ursid (e.g., bear), poultry, dog, cat, mouse, rat, fish, dolphin, whale and shark. The terms "subject" and "patient" are used interchangeably herein and refer to a human or non-human animal who is known to have, or potentially has, a medical condition or disorder, such as, e.g., a cancer. In some embodiments, a subject is a male or female of any stage (e.g., a man, a women or a child).

A subject from whom a sample is taken, or is treated by any of the methods or compositions described herein can be of any age and can be an adult, infant or child. In some cases, the subject, e.g., patient is 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 years old, or within a range therein (e.g., between about 2 and about 20 years old, between about 20 and about 40 years old, or between about 40 and about 90 years old). A particular class of subjects, e.g., patients that can benefit from a method of the present disclosure is subjects, e.g., patients over the age of 40.

Another particular class of subjects, e.g., patients that can benefit from a method of the present disclosure is pediatric patients, who can be at higher risk of chronic heart symptoms. Furthermore, a subject, e.g., patient from whom a sample is taken, or is treated by any of the methods or compositions described herein, can be male or female.

The term "normalize" as used herein means transforming a value or a set of values to a common frame of reference for comparison purposes. For example, when a diagnostic ctDNA level is "normalized" with a baseline ctDNA level, the diagnostic ctDNA level is compared to the baseline ctDNA level so that the amount by which the diagnostic ctDNA level differs from the baseline ctDNA level can be determined.

As used herein, the terms "biological sample," "patient sample," and "sample" are interchangeably used and refer to any sample taken from a subject, which can reflect a biological state associated with the subject. In some embodiments such samples contain cell-free nucleic acids such as cell-free DNA. In some embodiments, such samples include nucleic acids other than or in addition to cell-free nucleic acids. Examples of biological samples include, but are not limited to, blood, whole blood, plasma, serum, urine, cerebrospinal fluid, fecal, saliva, sweat, tears, pleural fluid, pericardial fluid, or peritoneal fluid of the subject. In some embodiments, the biological sample consists of blood, whole blood, plasma, serum, urine, cerebrospinal fluid, fecal, saliva, sweat, tears, pleural fluid, pericardial fluid, or peritoneal fluid of the subject. In such embodiments, the biological sample is limited to blood, whole blood, plasma, serum, urine, cerebrospinal fluid, fecal, saliva, sweat, tears, pleural fluid, pericardial fluid, or peritoneal fluid of the subject and does not contain other components (e.g., solid tissues, etc.) of the subject. A biological sample can include any tissue or material derived from a living or dead subject. A biological sample can be a cell-free sample. A biological sample can comprise a nucleic acid (e.g., DNA or RNA) or a fragment thereof. A sample can be a liquid sample or a solid sample (e.g., a cell or tissue sample). A biological sample can be a bodily fluid, such as blood, plasma, serum, urine, vaginal fluid, fluid from a hydrocele (e.g., of the testis), vaginal flushing fluids, pleural fluid, ascitic fluid, cerebrospinal fluid, saliva, sweat, tears, sputum, bronchoalveolar lavage fluid, discharge fluid from the nipple, aspiration fluid from different parts of the body (e.g., thyroid, breast), etc. A biological sample can be a stool sample. In various embodiments, the majority of DNA in a biological sample that has been enriched for cell-free DNA (e.g., a plasma sample obtained via a centrifugation protocol) can be cell-free (e.g., greater than 50%, 60%, 70%, 80%, 90%, 95%, or 99% of the DNA can be cell-free). A biological sample can be treated to physically disrupt tissue or cell structure (e.g., centrifugation and/or cell lysis), thus releasing intracellular components into a solution which can further contain enzymes, buffers, salts, detergents, and the like which can be used to prepare the sample for analysis. A biological sample can be obtained from a subject invasively (e.g., surgical means) or non-invasively (e.g., a blood draw, a swab, or collection of a discharged sample).

As used herein, the terms "nucleic acid" and "nucleic acid molecule" are used interchangeably. The terms refer to nucleic acids of any composition form, such as deoxyribonucleic acid (DNA, e.g., complementary DNA (cDNA), genomic DNA (gDNA) and the like), ribonucleic acid (RNA, e.g., message RNA (mRNA), short inhibitory RNA (siRNA), ribosomal RNA (rRNA), transfer RNA (tRNA), microRNA, RNA highly expressed by the fetus or placenta, and the like), and/or DNA or RNA analogs (e.g., containing base analogs, sugar analogs and/or a non-native backbone and the like), RNA/DNA hybrids and polyamide nucleic acids (PNAs), all of which can be in single- or double-stranded form. Unless otherwise limited, a nucleic acid can comprise known analogs of natural nucleotides, some of which can function in a similar manner as naturally occurring nucleotides. A nucleic acid can be in any form useful for conducting processes herein (e.g., linear, circular, supercoiled, single-stranded, double-stranded and the like). A nucleic acid may be, or may be from, a plasmid, phage, autonomously replicating sequence (ARS), centromere, artificial chromosome, chromosome, or other nucleic acid able to replicate or be replicated in vitro or in a host cell, a cell, a cell nucleus or cytoplasm of a cell in certain embodiments. A nucleic acid in some embodiments can be from a single chromosome or fragment thereof (e.g., a nucleic acid sample may be from one chromosome of a sample obtained from a diploid organism). In certain embodiments nucleic acids comprise nucleosomes, fragments or parts of nucleosomes or nucleosome-like structures. Nucleic acids sometimes comprise protein (e.g., histones, DNA binding proteins, and the like). Nucleic acids analyzed by processes described herein sometimes are substantially isolated and are not substantially associated with protein or other molecules. Nucleic acids also include derivatives, variants and analogs of RNA or DNA synthesized, replicated or amplified from single-stranded ("sense" or "antisense", "plus" strand or "minus" strand, "forward" reading frame or "reverse" reading frame) and double-stranded polynucleotides. Deoxyribonucleotides include deoxyadenosine, deoxycytidine, deoxyguanosine and deoxythymidine. For RNA, the base cytosine is replaced with uracil and the sugar 2' position includes a hydroxyl moiety. A nucleic acid may be prepared using a nucleic acid obtained from a subject as a template.

As used herein the term "cancer" or "tumor" refers to an abnormal mass of tissue in which the growth of the mass surpasses and is not coordinated with the growth of normal tissue. A cancer or tumor can be defined as "benign" or "malignant" depending on the following characteristics: degree of cellular differentiation including morphology and functionality, rate of growth, local invasion and metastasis. A "benign" tumor can be well differentiated, have characteristically slower growth than a malignant tumor and remain localized to the site of origin. In addition, in some cases a benign tumor does not have the capacity to infiltrate, invade or metastasize to distant sites. A "malignant" tumor can be a poorly differentiated (anaplasia), have characteristically rapid growth accompanied by progressive infiltration, invasion, and destruction of the surrounding tissue. Furthermore, a malignant tumor can have the capacity to metastasize to distant sites.

As used herein, the term "calibration sample" can correspond to a biological sample whose tissue-specific nucleic acid fraction is known or determined via a calibration method, e.g., using an allele specific to the tissue. As another example, a calibration sample can correspond to a sample from which preferred ending positions can be determined. A calibration sample can be used for both purposes.

As used herein the term "calibration data point" can include a "calibration value" and a measured or known proportional distribution of the nucleic acid of interest (e.g., DNA of particular tissue type). The calibration value can be a relative abundance as determined for a calibration sample, for which the proportional distribution of the tissue type can be known. The calibration data points can be defined in a variety of ways, e.g., as discrete points or as a calibration function (also called a calibration curve or calibration surface). The calibration function can be derived from additional mathematical transformation of the calibration data points.

As used herein the term "untrained classifier" refers to a classifier that has not been trained on a target dataset. For instance, consider the case of a target dataset that is a value training set discussed in further detail below. The value training set is applied as collective input to an untrained classifier, in conjunction with the cancer class of each respective reference subject represented by the value training set, to train the untrained classifier on cancer class thereby obtaining a trained classifier. The target dataset may represent raw or normalized measurements from subjects represented by the target dataset, principal components derived from such raw or normalized measurements, regression coefficients derived from the raw or normalized measurements (or the principal components of the raw or normalized measurements), or any other form of data from subjects with known disease class that is used to train classifiers in the art. In general, a target dataset is the dataset that is used to directly train an untrained classifier. However, it will be appreciated that the term "untrained classifier" does not exclude the possibility that transfer learning techniques are used in such training of the untrained classifier. For instance, Fernandes et al., 2017, "Transfer Learning with Partial Observability Applied to Cervical Cancer Screening," Pattern Recognition and Image Analysis: 8th Iberian Conference Proceedings, 243-250, which is hereby incorporated by reference, provides nonlimiting examples of such transfer learning. In the case where transfer learning is used, the untrained classifier described above is provided with additional data over and beyond that of the disease class labeled target dataset. That is, in non-limiting examples of transfer learning embodiments, the untrained classifier receives (i) the disease class labeled target training dataset (e.g., the value training set with each respective reference subject represented by the value training set labeled by cancer class) and (ii) additional data. Typically, this additional data is in the form of coefficients (e.g., regression coefficients) that were learned from another, auxiliary training dataset. More specifically, in some embodiments, the target training dataset is in the form of a first two-dimensional matrix, with one axis representing patients, and the other axis representing some property of respective patients, such as bin counts across all or a portion of the genome of respective patients in the target training set. Application of pattern classification techniques to the auxiliary training dataset yields a second two-dimensional matrix, where one axis is the learned coefficients and the other axis is the property of respective patients in the auxiliary training dataset, such as bin counts across all or a portion of respective patients in the first auxiliary training dataset. Matrix multiplication of the first and second matrices by their common dimension (e.g., bin counts) yields a third matrix of auxiliary data that can be applied, in addition to the first matrix to the untrained classifier. One reason it might be useful to train the untrained classifier using this additional information from an auxiliary training dataset is a paucity of subjects in one or more categories in the target dataset (e.g., the value training set). This is a particular issue for many healthcare datasets, where there may not be a large number of patients who have a particular disease or who are at a particular stage of a given disease. Making use of as much of the available data as possible can increase the accuracy of classifications and thus improve patient results. Thus, in the case where an auxiliary training dataset is used to train an untrained classifier beyond just the target training dataset (e.g., value training set), the auxiliary training dataset is subjected to classification techniques (e.g., principal component analysis followed by logistic regression) to learn coefficients (e.g., regression coefficients) that discriminate disease class based on the auxiliary training dataset. Such coefficients can be multiplied against a first instance of the target training dataset (e.g., the value training set) and inputted into the untrained classifier in conjunction with the target training dataset (e.g., the value training set) as collective input, in conjunction with the disease class (e.g., cancer class) of each respective reference subject in the target training dataset. As one of skill in the art will appreciate, such transfer learning can be applied with or without any form of dimension reduction technique on the auxiliary training dataset or the target training dataset. For instance, the auxiliary training dataset (from which coefficients are learned and used as input to the untrained classifier in addition to the target training dataset) can be subjected to a dimension reduction technique prior to regression (or other form of label based classification) to learn the coefficients that are applied to the target training dataset. Alternatively, no dimension reduction other than regression or some other form of pattern classification is used in some embodiments to learn such coefficients from the auxiliary training dataset prior to applying the coefficients to an instance of the target training dataset (e.g., through matrix multiplication where one matrix is the coefficients learned from the auxiliary training dataset and the second matrix is an instance of the target training dataset). Moreover, in some embodiments, rather than applying the coefficients learned from the auxiliary training dataset to the target training dataset, such coefficients are applied (e.g., by matrix multiplication based on a common axis of bin counts) to the bin count data that was collected from the first plurality of reference subjects that was used as a basis for forming the value training set as disclosed herein. Moreover, while a description of a single auxiliary training dataset has been disclosed, it will be appreciated that there is no limit on the number of auxiliary training datasets that may be used to complement the target training dataset in training the untrained classifier in the present disclosure. For instance, in some embodiments, two or more auxiliary training datasets, three or more auxiliary training datasets, four or more auxiliary training datasets or five or more auxiliary training datasets are used to complement the target training dataset through transfer learning, where each such auxiliary dataset is different than the target training dataset. Any manner of transfer learning may be used in such embodiments. For instance, consider the case where there is a first auxiliary training dataset and a second auxiliary training dataset in addition to the target training dataset (where, as before the target training dataset is any dataset that is directly used to train the untrained classifier). The coefficients learned from the first auxiliary training dataset (by application of a classifier such as regression to the first auxiliary training dataset) may be applied to the second auxiliary training dataset using transfer learning techniques (e.g., the above described two-dimensional matrix multiplication), which in turn may result in a trained intermediate classifier whose coefficients are then applied to the target training dataset and this, in conjunction with the target training dataset itself, is applied to the untrained classifier. Alternatively, a first set of coefficients learned from the first auxiliary training dataset (by application of a classifier such as regression to the first auxiliary training dataset) and a second set of coefficients learned from the second auxiliary training dataset (by application of a classifier such as regression to the second auxiliary training dataset) may each independently be applied to a separate instance of the target training dataset (e.g., by separate independent matrix multiplications) and both such applications of the coefficients to separate instances of the target training dataset in conjunction with the target training dataset itself (or some reduced form of the target training dataset such as principal components learned from the target training set) may then be applied to the untrained classifier in order to train the untrained classifier. In either example, knowledge regarding disease (e.g., cancer) classification derived from the first and second auxiliary training datasets is used, in conjunction with the disease labeled target training dataset (e.g., the value training dataset), to train the untrained classifier.

The term "classification" can refer to any number(s) or other characters(s) that are associated with a particular property of a sample. For example, a "+" symbol (or the word "positive") can signify that a sample is classified as having deletions or amplifications. In another example, the term "classification" refers to an amount of tumor tissue in the subject and/or sample, a size of the tumor in the subject and/or sample, a stage of the tumor in the subject, a tumor load in the subject and/or sample, and presence of tumor metastasis in the subject. In some embodiments, the classification is binary (e.g., positive or negative) or has more levels of classification (e.g., a scale from 1 to 10 or 0 to 1). In some embodiments, the terms "cutoff" and "threshold" refer to predetermined numbers used in an operation. In one example, a cutoff size refers to a size above which fragments are excluded. In some embodiments, a threshold value is a value above or below which a particular classification applies. Either of these terms can be used in either of these contexts.

As used herein, the term "cancer-associated changes" or "cancer-specific changes" can include cancer-derived mutations (including single nucleotide mutations, deletions or insertions of nucleotides, deletions of genetic or chromosomal segments, translocations, inversions), amplification of genes, virus-associated sequences (e.g., viral episomes, viral insertions, viral DNA that is infected into a cell and subsequently released by the cell, and circulating or cell-free viral DNA), aberrant methylation profiles or tumor-specific methylation signatures, aberrant cell-free nucleic acid (e.g., DNA) size profiles, aberrant histone modification marks and other epigenetic modifications, and locations of the ends of cell-free DNA fragments that are cancer-associated or cancer-specific.

As used herein, the term "cell-free nucleic acids" refers to nucleic acid molecules that can be found outside cells, in bodily fluids such as blood, whole blood, plasma, serum, urine, cerebrospinal fluid, fecal, saliva, sweat, sweat, tears, pleural fluid, pericardial fluid, or peritoneal fluid of a subject. Cell-free nucleic acids originate from one or more healthy cells and/or from one or more cancer cells Cell-free nucleic acids are used interchangeably as circulating nucleic acids. Examples of the cell-free nucleic acids include but are not limited to RNA, mitochondrial DNA, or genomic DNA. As used herein, the terms "cell-free nucleic acid," "cell-free DNA," and "cfDNA" are used interchangeably.

As used herein, the term "circulating tumor DNA" or "ctDNA" refers to nucleic acid fragments that originate from tumor cells or other types of cancer cells, which may be released into a fluid from an individual's body (e.g., bloodstream) as result of biological processes such as apoptosis or necrosis of dying cells or actively released by viable tumor cells. Examples of the cell-free nucleic acids include but are not limited to RNA, mitochondrial DNA, or genomic DNA.

As used herein, the terms "control," "control sample," "reference," "reference sample," "normal," and "normal sample" describe a sample from a subject that does not have a particular condition, or is otherwise healthy. In an example, a method as disclosed herein can be performed on a subject having a tumor, where the reference sample is a sample taken from a healthy tissue of the subject. A reference sample can be obtained from the subject, or from a database. The reference can be, e.g., a reference genome that is used to map nucleic acid fragments obtained from sequencing a sample from the subject. A reference genome can refer to a haploid or diploid genome to which sequence reads from the biological sample and a constitutional sample can be aligned and compared. An example of constitutional sample can be DNA of white blood cells obtained from the subject. For a haploid genome, there can be only one nucleotide at each locus. For a diploid genome, heterozygous loci can be identified; each heterozygous locus can have two alleles, where either allele can allow a match for alignment to the locus.

As used herein the term "ending position" or "end position" (or just "end") can refer to the genomic coordinate or genomic identity or nucleotide identity of the outermost base, e.g., at the extremities, of a cell-free DNA molecule, e.g., plasma DNA molecule. The end position can correspond to either end of a DNA molecule. In this manner, if one refers to a start and end of a DNA molecule, both can correspond to an ending position. In some cases, one end position is the genomic coordinate or the nucleotide identity of the outermost base on one extremity of a cell-free DNA molecule that is detected or determined by an analytical method, e.g., massively parallel sequencing or next-generation sequencing, single molecule sequencing, double- or single-stranded DNA sequencing library preparation protocols, polymerase chain reaction (PCR), or microarray. In some cases, such in vitro techniques can alter the true in vivo physical end(s) of the cell-free DNA molecules. Thus, each detectable end can represent the biologically true end or the end is one or more nucleotides inwards or one or more nucleotides extended from the original end of the molecule e.g., 5' blunting and 3' filling of overhangs of non-blunt-ended double stranded DNA molecules by the Klenow fragment. The genomic identity or genomic coordinate of the end position can be derived from results of alignment of sequence reads to a human reference genome, e.g., hg19. It can be derived from a catalog of indices or codes that represent the original coordinates of the human genome. It can refer to a position or nucleotide identity on a cell-free DNA molecule that is read by but not limited to target-specific probes, mini-sequencing, DNA amplification. The term "genomic position" can refer to a nucleotide position in a polynucleotide (e.g., a gene, a plasmid, a nucleic acid fragment, a viral DNA fragment). The term "genomic position" is not limited to nucleotide positions within a genome (e.g., the haploid set of chromosomes in a gamete or microorganism, or in each cell of a multicellular organism).

As used herein, the term "false positive" (FP) refers to a subject that does not have a condition. In some embodiments, false positive refers to a subject that does not have a tumor, a cancer, a precancerous condition (e.g., a precancerous lesion), a localized or a metastasized cancer, a non-malignant disease, or is otherwise healthy. In some embodiments, the term false positive refers to a subject that does not have a condition, but is identified as having the condition by an assay or method of the present disclosure.

As used herein, the term "false negative" (FN) refers to a subject that has a condition. In some embodiments, false negative refers to a subject that has a tumor, a cancer, a precancerous condition (e.g., a precancerous lesion), a localized or a metastasized cancer, or a non-malignant disease. In some embodiments, the term false negative refers to a subject that has a condition, but is identified as not having the condition by an assay or method of the present disclosure.

As used herein, the term "true positive" (TP) refers to a subject having a condition. "True positive" can refer to a subject that has a tumor, a cancer, a precancerous condition (e.g., a precancerous lesion), a localized or a metastasized cancer, or a non-malignant disease. "True positive" can refer to a subject having a condition, and is identified as having the condition by an assay or method of the present disclosure.

As used herein, the term "true negative" (TN) refers to a subject that does not have a condition or does not have a detectable condition. In some embodiments, true negative refers to a subject that does not have a disease or a detectable disease, such as a tumor, a cancer, a precancerous condition (e.g., a precancerous lesion), a localized or a metastasized cancer, a non-malignant disease, or a subject that is otherwise healthy. In some embodiments, true negative refers to a subject that does not have a condition or does not have a detectable condition, or is identified as not having the condition by an assay or method of the present disclosure.

As used herein, the "negative predictive value" or "NPV" can be calculated by TN/(TN+FN) or the true negative fraction of all negative test results. Negative predictive value can be inherently impacted by the prevalence of a condition in a population and pre-test probability of the population intended to be tested. The term "positive predictive value" or "PPV" can be calculated by TP/(TP+FP) or the true positive fraction of all positive test results. PPV can be inherently impacted by the prevalence of a condition in a population and pre-test probability of the population intended to be tested. See, e.g., O'Marcaigh A S, Jacobson R M, "Estimating The Predictive Value of a Diagnostic Test, How to Prevent Misleading or Confusing Results," Clin. Ped. 1993, 32 (8): 485-491, which is entirely incorporated herein by reference.

As used herein, the term "sensitivity" or "true positive rate" (TPR) refers to the number of true positives divided by the sum of the number of true positives and false negatives (e.g., calculated by TP/(TP+FN)). Sensitivity can characterize the ability of an assay or method to correctly identify a proportion of the population that truly has a condition. For example, sensitivity can characterize the ability of a method to correctly identify the number of subjects within a population having cancer. In another example, sensitivity can characterize the ability of a method to correctly identify the one or more markers indicative of cancer.

As used herein, the term "specificity" or "true negative rate" (TNR) refers to the number of true negatives divided by the sum of the number of true negatives and false positives (e.g., calculated by TN/(TN+FP)). Specificity can characterize the ability of an assay or method to correctly identify a proportion of the population that truly does not have a condition. For example, specificity can characterize the ability of a method to correctly identify the number of subjects within a population not having cancer. In another example, specificity can characterize the ability of a method to correctly identify one or more markers indicative of cancer.

As used herein, the term "fragment" is used interchangeably with "nucleic acid fragment" (e.g., a DNA fragment), and refers to a portion of a polynucleotide or polypeptide sequence that comprises at least three consecutive nucleotides. In the context of sequencing of nucleic cell-free nucleic acid fragments found in a biological sample, the terms "fragment" and "nucleic acid fragment" interchangeably refer to a cell-free nucleic acid molecule that is found in the biological sample or a representation thereof. In such a context, sequencing data (e.g., sequence reads from whole genome sequencing, targeted sequencing, etc.) are used to derive one or more copies of all or a portion of such a nucleic acid fragment. Such sequence reads, which in fact may be obtained from sequencing of PCR duplicates of the original nucleic acid fragment, therefore "represent" or "support" the nucleic acid fragment. There may be a plurality of sequence reads that each represent or support a particular nucleic acid fragment in the biological sample (e.g., PCR duplicates). In some embodiments, nucleic acid fragments can be considered cell-free nucleic acids. In some embodiments, sequence reads from PCR duplicates can be misleading; for example, when the abundance level of a particular cell-free nucleic acid molecule needs to be determined. In such embodiments, only one copy of a nucleic acid fragment is used to represent the original cell-free nucleic acid molecule (e.g., duplicates are removed through molecular identifiers that are attached to the cell-free nucleic acid molecule during the library preparation process). In some embodiments, methylation sequencing data can be used to further distinguish these nucleic acid fragments. For example, two nucleic acid fragments that share identical or near identical sequences may still correspond to different original cell-free nucleic acid molecules if they each harbor a different methylation pattern.

As used herein, the term "informative cancer DNA fragment" or an "informative DNA fragment" can correspond to a DNA fragment bearing or carrying any one or more of the cancer-associated or cancer-specific change or mutation, or a particular ending-motif (e.g., a number of nucleotides at each end of the DNA fragment having a particular sequence).

As used herein, the phrase "healthy," refers to a subject possessing good health. A healthy subject can demonstrate an absence of any malignant or non-malignant disease. A "healthy individual" can have other diseases or conditions, unrelated to the condition being assayed, which can normally not be considered "healthy."

The terms "cancer load," "tumor load," "cancer burden" and "tumor burden" are used interchangeably herein to refer to a concentration or presence of tumor-derived nucleic acids in a test sample. As such, the terms "cancer load," "tumor load," "cancer burden" and "tumor burden" are non-limiting examples of a cell source fraction in a biological sample.

As used herein, the term "level of cancer" refers to whether cancer exists (e.g., presence or absence), a stage of a cancer, a size of tumor, presence or absence of metastasis, the total tumor burden of the body, and/or other measure of a severity of a cancer (e.g., recurrence of cancer). The level of cancer can be a number or other indicia, such as symbols, alphabet letters, and colors. The level can be zero. The level of cancer can also include premalignant or precancerous conditions (states) associated with mutations or a number of mutations. The level of cancer can be used in various ways. For example, screening can check if cancer is present in someone who is not known previously to have cancer. Assessment can investigate someone who has been diagnosed with cancer to monitor the progress of cancer over time, study the effectiveness of therapies or to determine the prognosis. In one embodiment, the prognosis can be expressed as the chance of a subject dying of cancer, or the chance of the cancer progressing after a specific duration or time, or the chance of cancer metastasizing. Detection can comprise 'screening' or can comprise checking if someone, with suggestive features of cancer (e.g., symptoms or other positive tests), has cancer.

As used herein, a "local maximum" can refer to a genomic position (e.g., a nucleotide) at which the largest value of the parameter of interest is obtained when compared with the neighboring positions or refer to the value of the parameter of interest at such a genomic position. As examples, the neighboring positions can range from 50 bp to 2000 bp. Examples for the parameter of interest include, but are not limited to, the number of fragments ending on a genomic position, the number of fragments overlapping with the position, or the proportion of fragments covering the genomic position that are larger than a threshold size. Many local maxima can occur when the parameter of interest has a periodic structure. A global maximum is a specific one of the local maxima. Similarly, a "local minimum" refers to a genomic position at which the smallest value of the parameter of interest is obtained when compared with the neighboring positions or refer to the value of the parameter of interest at such a genomic position.

As used herein a "methylome" can be a measure of an amount of DNA methylation at a plurality of sites or loci in a genome. The methylome can correspond to all of a genome, a substantial part of a genome, or relatively small portion(s) of a genome. A "tumor methylome" can be a methylome of a tumor of a subject (e.g., a human). A tumor methylome can be determined using tumor tissue or cell-free tumor DNA in plasma. A tumor methylome can be one example of a methylome of interest. A methylome of interest can be a methylome of an organ that can contribute nucleic acid, e.g., DNA into a bodily fluid (e.g., a methylome of brain cells, a bone, lungs, heart, muscles, kidneys, etc.). The organ can be a transplanted organ.

As used herein, the term "methylation" refers to a modification of deoxyribonucleic acid (DNA) where a hydrogen atom on the pyrimidine ring of a cytosine base is converted to a methyl group, forming 5-methylcytosine. In particular, methylation tends to occur at dinucleotides of cytosine and guanine referred to herein as "CpG sites". In other instances, methylation may occur at a cytosine not part of a CpG site or at another nucleotide that's not cytosine; however, these are rarer occurrences. In this present disclosure, methylation is discussed in reference to CpG sites for the sake of clarity.

Anomalous cfDNA methylation can identified as hypermethylation or hypomethylation, both of which may be indicative of cancer status. As is well known in the art, DNA methylation anomalies (compared to healthy controls) can cause different effects, which may contribute to cancer.

Various challenges arise in the identification of anomalously methylated cfDNA fragments. First, determining a subject's cfDNA to be anomalously methylated only holds weight in comparison with a group of control subjects, such that if the control group is small in number, the determination loses confidence with the small control group. Additionally, among a group of control subjects' methylation status can vary which can be difficult to account for when determining a subject's cfDNA to be anomalously methylated. On another note, methylation of a cytosine at a CpG site causally influences methylation at a subsequent CpG site.

Those of skill in the art will appreciate that the principles described herein are equally applicable for the detection of methylation in a non-CpG context, including non-cytosine methylation. Further, the methylation state vectors may contain elements that are generally vectors of sites where methylation has or has not occurred (even if those sites are not CpG sites specifically). With that substitution, the remainder of the processes described herein are the same, and consequently the inventive concepts described herein are applicable to those other forms of methylation.

As used herein the term "methylation index" for each genomic site (e.g., a CpG site, a region of DNA where a cytosine nucleotide is followed by a guanine nucleotide in the linear sequence of bases along its 5'→3' direction) can refer to the proportion of nucleic acid fragments showing methylation at the site over the total number of reads covering that site. The "methylation density" of a region can be the number of reads at sites within a region showing methylation divided by the total number of reads covering the sites in the region. The sites can have specific characteristics, (e.g., the sites can be CpG sites). The "CpG methylation density" of a region can be the number of reads showing CpG methylation divided by the total number of reads covering CpG sites in the region (e.g., a particular CpG site, CpG sites within a CpG island, or a larger region). For example, the methylation density for each 100-kb bin in the human genome can be determined from the total number of unconverted cytosines (which can correspond to methylated cytosine) at CpG sites as a proportion of all CpG sites covered by nucleic acid fragments mapped to the 100-kb region. In some embodiments, this analysis is performed for other bin sizes, e.g., 50-kb or 1-Mb, etc. In some embodiments, a region is an entire genome or a chromosome or part of a chromosome (e.g., a chromosomal arm). A methylation index of a CpG site can be the same as the methylation density for a region when the region only includes that CpG site. The "proportion of methylated cytosines" can refer the number of cytosine sites, "C's," that are shown to be methylated (for example unconverted after bisulfite conversion) over the total number of analyzed cytosine residues, e.g., including cytosines outside of the CpG context, in the region. The methylation index, methylation density and proportion of methylated cytosines are examples of "methylation levels."

As used herein, the term "methylation profile" (also called methylation status) can include information related to DNA methylation for a region. Information related to DNA methylation can include a methylation index of a CpG site, a methylation density of CpG sites in a region, a distribution of CpG sites over a contiguous region, a pattern or level of methylation for each individual CpG site within a region that contains more than one CpG site, and non-CpG methylation. A methylation profile of a substantial part of the genome can be considered equivalent to the methylome. "DNA methylation" in mammalian genomes can refer to the addition of a methyl group to position 5 of the heterocyclic ring of cytosine (e.g., to produce 5-methylcytosine) among CpG dinucleotides. Methylation of cytosine can occur in cytosines in other sequence contexts, for example 5'-CHG-3' and 5'-CHH-3', where H is adenine, cytosine or thymine. Cytosine methylation can also be in the form of 5-hydroxymethylcytosine. Methylation of DNA can include methylation of non-cytosine nucleotides, such as N6-methyladenine.

As used herein, the term "mutation," refers to a detectable change in the genetic material of one or more cells. In a particular example, one or more mutations can be found in, and can identify, cancer cells (e.g., driver and passenger mutations). A mutation can be transmitted from apparent cell to a daughter cell. A person having skill in the art will appreciate that a genetic mutation (e.g., a driver mutation) in a parent cell can induce additional, different mutations (e.g., passenger mutations) in a daughter cell. A mutation generally occurs in a nucleic acid. In a particular example, a mutation can be a detectable change in one or more deoxyribonucleic acids or fragments thereof. A mutation generally refers to nucleotides that is added, deleted, substituted for, inverted, or transposed to a new position in a nucleic acid. A mutation can be a spontaneous mutation or an experimentally induced mutation. A mutation in the sequence of a particular tissue is an example of a "tissue-specific allele." For example, a tumor can have a mutation that results in an allele at a locus that does not occur in normal cells. Another example of a "tissue-specific allele" is a fetal-specific allele that occurs in the fetal tissue, but not the maternal tissue.

As used herein the term "preferred end" (or "recurrent ending position") can refer to an end that is more highly represented or prevalent (e.g., as measured by a rate) in a biological sample having a physiological or pathological (disease) state (e.g., cancer) than a biological sample not having such a state or than at different time points or stages of the same pathological or physiological state, e.g., before or after treatment. A preferred end can have an increased likelihood or probability for being detected in the relevant physiological or pathological state relative to other states. The increased probability can be compared between the pathological state and a non-pathological state, for example in subjects with and without a cancer and quantified as likelihood ratio or relative probability. The likelihood ratio can be determined based on the probability of detecting at least a threshold number of preferred ends in the tested sample or based on the probability of detecting the preferred ends in subjects with such a condition than subjects without such a condition. Examples for the thresholds of likelihood ratios include but are not limited to 1.1, 1.2, 1.3, 1.4, 1.5, 1.6, 1.8, 2.0, 2.5, 3.0, 3.5, 4.0, 4.5, 5, 6, 8, 10, 20, 40, 60, 80 and 100. In some embodiments, such likelihood ratios are measured by comparing relative abundance values of samples with and without the relevant state. Because the probability of detecting a preferred end in a relevant physiological or disease state can be higher, such preferred ending positions can be seen in more than one individual with that same physiological or disease state. With the increased probability, more than one cell-free DNA molecule can be detected as ending on a same preferred ending position, even when the number of cell-free DNA molecules analyzed is far less than the size of the genome. Thus, the preferred or recurrent ending positions can also be referred to as the "frequent ending positions." A quantitative threshold generally requires that ends be detected at least multiple times (e.g., 3, 4, 5, 6, 7, 8, 9, 10, 15, 20, or 50) within the same sample or same sample aliquot to be considered as a preferred end. A relevant physiological state can include a state when a person is healthy, disease-free, or free from a disease of interest. Similarly, in some embodiments, a "preferred ending window" corresponds to a contiguous set of preferred ending positions.

As used herein, the term "random sequencing," refers to sequencing whereby nucleic acid fragments sequenced have not been specifically identified or predetermined before the sequencing procedure. Sequence-specific primers to target specific gene loci are not required. In some embodiments, adapters are added to the end of a nucleic acid fragment, and primers for sequencing are attached (e.g., hybridized) to the adapters. Thus, any fragment can be sequenced with the same primer, e.g., that attaches to a same universal adapter, and thus the sequencing can be random. Massively parallel sequencing can include using random sequencing.

As used herein, the term "rate" of nucleic acid molecules (e.g., DNA or RNA) ending on a position can relate to how frequently a nucleic acid molecule ends on the position. The rate can be based on a number of nucleic acid molecules that end on the position normalized against a number of nucleic acid molecules analyzed. The rate can be based on a number of nucleic acid molecules that end on the position normalized against a number of nucleic acid molecules that end on a different position. The rate can be based on a number of nucleic acid molecules from a first sample that end on the position normalized against a number of nucleic acid molecules from a second sample (e.g., a reference sample) that end on the position. The rate can be based on a number of nucleic acid molecules from a first sample that end on a first set of positions (e.g., genomic positions) normalized against a number of nucleic acid molecules from a second sample (e.g., a reference sample) that end on a second set of positions. Accordingly, the rate can correspond to a frequency of how many nucleic acid molecules end on a position, and in some cases does not relate to a periodicity of positions having a local maximum in the number of nucleic acid molecules ending on the position.

As used herein, the term "relative abundance" can refer to a ratio of a first amount of nucleic acid fragments having a particular characteristic (e.g., a specified length, ending at one or more specified coordinates/ending positions, aligning to a particular region of the genome, or having a particular methylation status) to a second amount nucleic acid fragments having a particular characteristic (e.g., a specified length, ending at one or more specified coordinates/ending positions, aligning to a particular region of the genome, or having a particular methylation status). In one example, relative abundance may refer to a ratio of the number of DNA fragments ending at a first set of genomic positions to the number of DNA fragments ending at a second set of genomic positions. In some aspects, a "relative abundance" can be a type of separation value that relates an amount (one value) of cell-free DNA molecules ending within one window of genomic position to an amount (other value) of cell-free DNA molecules ending within another window of genomic positions. The two windows can overlap, but can be of different sizes. In other embodiments, the two windows cannot overlap. Further, in some embodiments, the windows are of a width of one nucleotide, and therefore are equivalent to one genomic position.

As used herein, the term "ROC" or "ROC curve," refers to a receiver operator characteristic curve. In some embodiments, a ROC curve is depicted as a graphical representation of the performance of a binary classifier system. For any given method, a ROC curve can be generated by plotting the sensitivity against the specificity at various threshold settings. In some embodiments, the sensitivity and specificity of a method for detecting the presence of a tumor in a subject is determined at various concentrations of tumor-derived DNA in the plasma sample of the subject. Furthermore, in some embodiments, provided at least one of three parameters (e.g., sensitivity, specificity, and the threshold setting), a ROC curve determines the value or expected value for any unknown parameter. The unknown parameter can be determined using a curve fitted to a ROC curve. For example, provided the concentration of tumor-derived DNA in a sample, the expected sensitivity and/or specificity of a test can be determined. The term "AUC" or "ROC-AUC" can refer to the area under a receiver operator characteristic curve. This metric can provide a measure of diagnostic utility of a method, taking into account both the sensitivity and specificity of the method. A ROC-AUC can range from 0.5 to 1.0, where a value closer to 0.5 can indicate a method has limited diagnostic utility (e.g., lower sensitivity and/or specificity) and a value closer to 1.0 indicates the method has greater diagnostic utility (e.g., higher sensitivity and/or specificity). See, e.g., Pepe et al., "Limitations of the Odds Ratio in Gauging the Performance of a Diagnostic, Prognostic, or Screening Marker," Am. J. Epidemiol 2004, 159 (9): 882-890, which is entirely incorporated herein by reference. Additional approaches for characterizing diagnostic utility include using likelihood functions, odds ratios, information theory, predictive values, calibration (including goodness-of-fit), and reclassification measurements. Examples of the approaches are summarized, e.g., in Cook, "Use and Misuse of the Receiver Operating Characteristic Curve in Risk Prediction," Circulation 2007, 115:928-935, which is entirely incorporated herein by reference.

As used herein, the term "reference genome" refers to any particular known, sequenced or characterized genome, whether partial or complete, of any organism or virus that may be used to reference identified sequences from a subject. Exemplary reference genomes used for human subjects as well as many other organisms are provided in the on-line genome browser hosted by the National Center for Biotechnology Information ("NCBI") or the University of California, Santa Cruz (UCSC). A "genome" refers to the complete genetic information of an organism or virus, expressed in nucleic acid sequences. As used herein, a reference sequence or reference genome often is an assembled or partially assembled genomic sequence from an individual or multiple individuals. In some embodiments, a reference genome is an assembled or partially assembled genomic sequence from one or more human individuals. The reference genome can be viewed as a representative example of a species' set of genes. In some embodiments, a reference genome comprises sequences assigned to chromosomes. Exemplary human reference genomes include but are not limited to NCBI build 34 (UCSC equivalent: hg16), NCBI build 35 (UCSC equivalent: hg17), NCBI build 36.1 (UCSC equivalent: hg18), GRCh37 (UCSC equivalent: hg19), and GRCh38 (UCSC equivalent: hg38).

As disclosed herein, the term "regions of a reference genome," "genomic region," or "chromosomal region" refers to any portion of a reference genome, contiguous or non-contiguous. It can also be referred to, for example, as a bin, a partition, a genomic portion, a portion of a reference genome, a portion of a chromosome and the like. In some embodiments, a genomic section is based on a particular length of genomic sequence. In some embodiments, a method can include analysis of multiple mapped nucleic acid fragments to a plurality of genomic regions. Genomic regions can be approximately the same length or the genomic sections can be different lengths. In some embodiments, genomic regions are of about equal length. In some embodiments genomic regions of different lengths are adjusted or weighted. In some embodiments, a genomic region is about 10 kilobases (kb) to about 500 kb, about 20 kb to about 400 kb, about 30 kb to about 300 kb, about 40 kb to about 200 kb, and sometimes about 50 kb to about 100 kb. In some embodiments, a genomic region is about 100 kb to about 200 kb. A genomic region is not limited to contiguous runs of sequence. Thus, genomic regions can be made up of contiguous and/or non-contiguous sequences. A genomic region is not limited to a single chromosome. In some embodiments, a genomic region includes all or part of one chromosome or all or part of two or more chromosomes. In some embodiments, genomic regions may span one, two, or more entire chromosomes. In addition, the genomic regions may span joint or disjointed portions of multiple chromosomes.

As used herein, the term "sequence reads" or "reads" refers to nucleotide sequences produced by any sequencing process described herein or known in the art. Reads can be generated from one end of nucleic acid fragments ("single-end reads"), and sometimes are generated from both ends of nucleic acids (e.g., paired-end reads, double-end reads). The length of the sequence read is often associated with the particular sequencing technology. High-throughput methods, for example, provide sequence reads that vary in size from tens to hundreds of base pairs (bp). In some embodiments, the sequence reads are of a mean, median or average length of about 15 bp to 900 bp long (e.g., about 20 bp, about 25 bp, about 30 bp, about 35 bp, about 40 bp, about 45 bp, about 50 bp, about 55 bp, about 60 bp, about 65 bp, about 70 bp, about 75 bp, about 80 bp, about 85 bp, about 90 bp, about 95 bp, about 100 bp, about 110 bp, about 120 bp, about 130, about 140 bp, about 150 bp, about 200 bp, about 250 bp, about 300 bp, about 350 bp, about 400 bp, about 450 bp, or about 500 bp. In some embodiments, the sequence reads are of a mean, median or average length of about 1000 bp, 2000 bp, 5000 bp, 10,000 bp, or 50,000 bp or more. Nanopore sequencing, for example, can provide sequence reads that can vary in size from tens to hundreds to thousands of base pairs. Illumina parallel sequencing can provide sequence reads that do not vary as much, for example, most of the sequence reads can be smaller than 200 bp. A sequence read (or sequencing read) can refer to sequence information corresponding to a nucleic acid molecule (e.g., a string of nucleotides). For example, a sequence read can correspond to a string of nucleotides (e.g., about 20 to about 150) from part of a nucleic acid fragment, can correspond to a string of nucleotides at one or both ends of a nucleic acid fragment, or can correspond to nucleotides of the entire nucleic acid fragment. A sequence read can be obtained in a variety of ways, e.g., using sequencing techniques or using probes, e.g., in hybridization arrays or capture probes, or amplification techniques, such as the polymerase chain reaction (PCR) or linear amplification using a single primer or isothermal amplification.

As used herein, the terms "sequencing," "sequence determination," and the like as used herein refers generally to any and all biochemical processes that may be used to determine the order of biological macromolecules such as nucleic acids or proteins. For example, sequencing data can include all or a portion of the nucleotide bases in a nucleic acid molecule such as a DNA fragment.

As used herein the term "sequencing breadth" refers to what fraction of a particular reference genome (e.g., human reference genome) or part of the genome has been analyzed. The denominator of the fraction can be a repeat-masked genome, and thus 100% can correspond to all of the reference genome minus the masked parts. A repeat-masked genome can refer to a genome in which sequence repeats are masked (e.g., sequence reads align to unmasked portions of the genome). Any parts of a genome can be masked, and thus one can focus on any particular part of a reference genome. Broad sequencing can refer to sequencing and analyzing at least 0.1% of the genome.

As used herein the term "sequencing depth" refers to the number of times a locus is covered by a sequence read aligned to the locus. In some embodiments, the locus is as small as a nucleotide, or as large as a chromosome arm, or as large as an entire genome. In some embodiments, sequencing depth is expressed as "Yx", e.g., 50×, 100×, etc., where "Y" refers to the number of times a locus is covered with a sequence read. In some embodiments, sequencing depth is also applied to multiple loci, or the whole genome, in which case Y refers to the mean number of times a loci or a haploid genome, or a whole genome, respectively, is sequenced. In some embodiments, when a mean depth is quoted, the actual depth for different loci included in the dataset spans over a range of values. In some embodiments, the term "ultra-deep" sequencing refers to at least 100× in sequencing depth at a locus.

As used herein, the term "single nucleotide variant" or "SNV" refers to a substitution of one nucleotide to a different nucleotide at a position (e.g., site) of a nucleotide sequence, e.g., a sequence read from an individual. A substitution from a first nucleobase X to a second nucleobase Y may be denoted as "X>Y." For example, a cytosine to thymine SNV may be denoted as "C>T."

As used herein, the terms "size profile" and "size distribution" can relate to the sizes of DNA fragments in a biological sample. A size profile can be a histogram that provides a distribution of an amount of DNA fragments at a variety of sizes. Various statistical parameters (also referred to as size parameters or just parameter) can distinguish one size profile to another. In some embodiments, one such parameter is the percentage of DNA fragment of a particular size or range of sizes relative to all DNA fragments or relative to DNA fragments of another size or range.

As used herein, the term "tissue" can correspond to a group of cells that group together as a functional unit. More than one type of cell can be found in a single tissue. Different types of tissue may consist of different types of cells (e.g., hepatocytes, alveolar cells or blood cells), but also can correspond to tissue from different organisms (mother vs. fetus) or to healthy cells vs. tumor cells. The term "tissue" can generally refer to any group of cells found in the human body (e.g., heart tissue, lung tissue, kidney tissue, nasopharyngeal tissue, oropharyngeal tissue). In some aspects, the term "tissue" or "tissue type" can be used to refer to a tissue from which a cell-free nucleic acid originates. In one example, viral nucleic acid fragments can be derived from blood tissue. In another example, viral nucleic acid fragments can be derived from tumor tissue.

The terminology used herein is for the purpose of describing particular cases only and is not intended to be limiting. As used herein, the singular forms "a," "an" and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising."

Several aspects are described below with reference to example applications for illustration. It should be understood that numerous specific details, relationships, and methods are set forth to provide a full understanding of the features described herein. One having ordinary skill in the relevant art, however, will readily recognize that the features described herein can be practiced without one or more of the specific details or with other methods. The features described herein are not limited by the illustrated ordering of acts or events, as some acts can occur in different orders and/or concurrently with other acts or events. Furthermore, not all illustrated acts or events are required to implement a methodology in accordance with the features described herein.

Exemplary System Embodiments

Details of an exemplary system are now described in conjunction with FIG. 1. FIG. 1 is a block diagram illustrating system 100 in accordance with some implementations. Device 100 in some implementations includes one or more processing units CPU(s) 102 (also referred to as processors or processing core), one or more network interfaces 104, user interface 106, non-persistent memory 111, persistent memory 112, and one or more communication buses 114 for interconnecting these components. One or more communication buses 114 optionally include circuitry (sometimes called a chipset) that interconnects and controls communications between system components. Non-persistent memory 111 typically includes high-speed random access memory, such as DRAM, SRAM, DDR RAM, ROM, EEPROM, flash memory, whereas persistent memory 112 typically includes CD-ROM, digital versatile disks (DVD) or other optical storage, magnetic cassettes, magnetic tape, magnetic disk storage or other magnetic storage devices, magnetic disk storage devices, optical disk storage devices, flash memory devices, or other non-volatile solid state storage devices. Persistent memory 112 optionally includes one or more storage devices remotely located from the CPU(s) 102. Persistent memory 112, and the non-volatile memory device(s) within non-persistent memory 112, comprise non-transitory computer readable storage medium. In some implementations, non-persistent memory 111 or alternatively non-transitory computer readable storage medium stores the following programs, modules and data structures, or a subset thereof, sometimes in conjunction with persistent memory 112:

optional operating system 116, which includes procedures for handling various basic system services and for performing hardware dependent tasks;

optional network communication module (or instructions) 118 for connecting the system 100 with other devices, or a communication network;

condition evaluation module 120 for screening for a cancer condition in a test subject;

information for each respective reference subject 122 in a plurality of reference subjects including (i) cancer condition 124 of the respective reference subject and (ii) at least one sequencing construct 126 (e.g., genotypic data construct 126) for the respective subject;

information for each respective test subject 130 in a plurality of reference subjects including at least one sequencing construct 134 for the respective subject.

In various embodiments, sequencing data construct 126 or 134 includes sequencing information 128, 136 for each respective chromosome in a plurality of chromosomes of a particular species (e.g., human).

In various implementations, one or more of the above identified elements are stored in one or more of the previously mentioned memory devices, and correspond to a set of instructions for performing a function described above. The above identified modules, data, or programs (e.g., sets of instructions) need not be implemented as separate software programs, procedures, datasets, or modules, and thus various subsets of these modules and data may be combined or otherwise re-arranged in various implementations. In some implementations, non-persistent memory 111 optionally stores a subset of the modules and data structures identified above. Furthermore, in some embodiments, the memory stores additional modules and data structures not described above. In some embodiments, one or more of the above identified elements is stored in a computer system, other than that of visualization system 100, that is addressable by visualization system 100 so that visualization system 100 may retrieve all or a portion of such data when needed.

Although FIG. 1 depicts a "system 100," the figure is intended more as functional description of the various features which may be present in computer systems than as a structural schematic of the implementations described herein. In practice, and as recognized by those of ordinary skill in the art, items shown separately could be combined and some items could be separated. Moreover, although FIG. 1 depicts certain data and modules in non-persistent memory 111, some or all of these data and modules may be in persistent memory 112.

Figure 2:
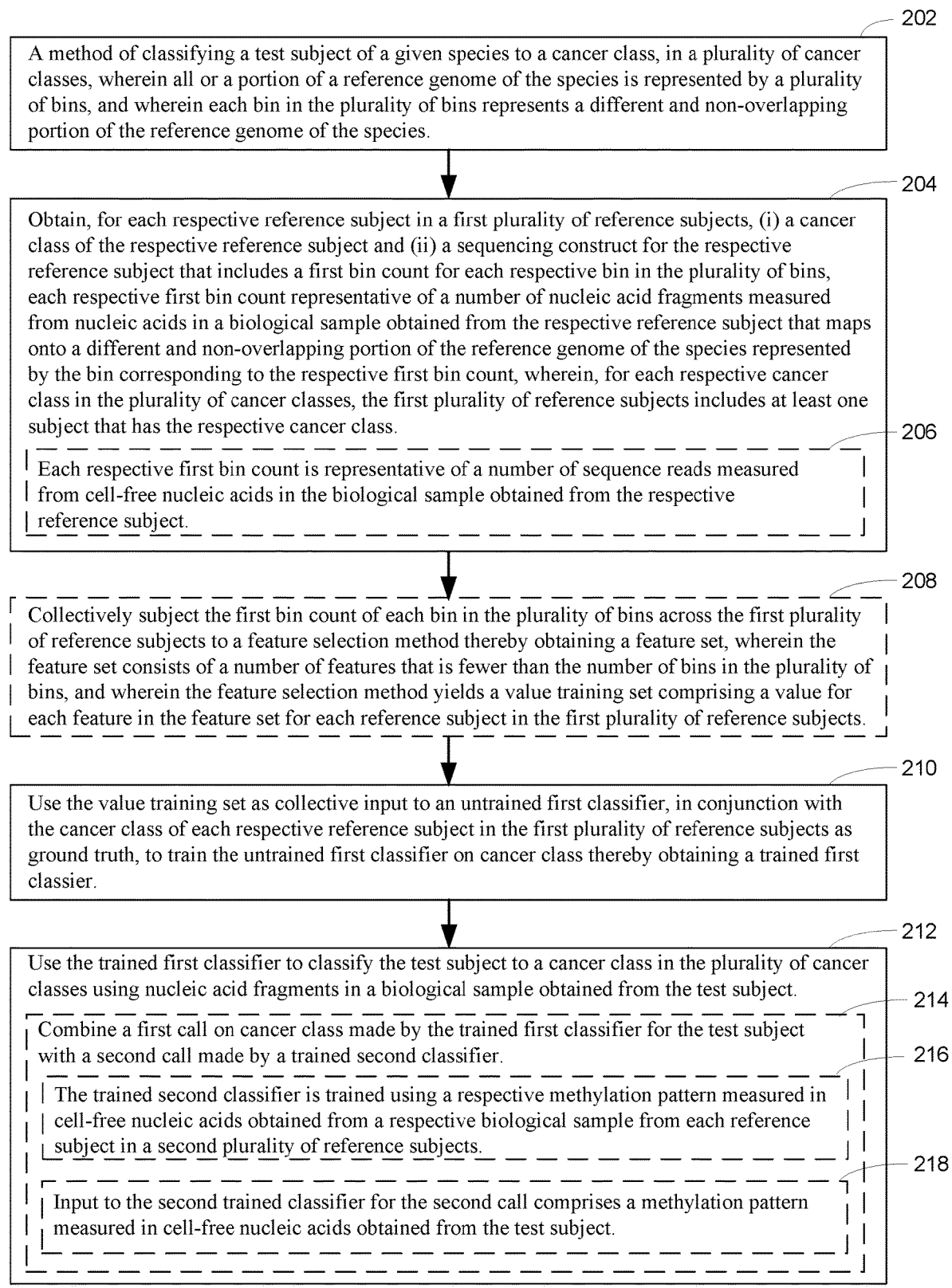
FIG. 2 illustrates an example flowchart of a method for classifying a cancer condition, in a plurality of different cancer conditions, for a species in accordance with some embodiments of the present disclosure.

While a system in accordance with the present disclosure has been disclosed with reference to FIG. 1, methods in accordance with the present disclosure are now detailed with reference to FIG. 2. It will be appreciated that any of the disclosed methods can make use of any of the assays or algorithms disclosed in U.S. patent application Ser. No. 15/793,830, filed Oct. 25, 2017 and/or International Patent Publication No. PCT/US17/58099, having an International Filing Date of Oct. 24, 2017, each of which is hereby incorporated by reference, in order to determine a cancer condition in a test subject or a likelihood that the subject has the cancer condition. For instance, any of the disclosed methods can work in conjunction with any of the disclosed methods or algorithms disclosed in U.S. patent application Ser. No. 15/793,830, filed Oct. 25, 2017, and/or International Patent Publication No. PCT/US17/58099, having an International Filing Date of Oct. 24, 2017.

Block 202. A method of classifying a test subject of a given species to a cancer class, in a plurality of cancer classes, is provided. All or a portion of a reference genome of the species is represented by a plurality of bins. Each bin in the plurality of bins represents a different and non-overlapping portion of the reference genome of the species.

In some embodiments, the terms bin and region are interchangeable. In some embodiments, the reference genome is represented by a plurality of bins, as represented in clustered form in the columns of FIG. 3 and as further disclosed in Example 1.

Block 204. Using computer system 100, there is obtained, for each respective reference subject in a first plurality of reference subjects, (i) a cancer class of respective reference subject 124 and (ii) a sequencing construct 126 for respective reference subject that includes a first bin count for each respective bin in the plurality of bins, each respective first bin count representative of a number of nucleic acid fragments measured from a biological sample obtained from the respective reference subject that maps onto a different and non-overlapping portion of the reference genome of the species represented by the bin corresponding to the respective first bin count, wherein, for each respective cancer class in the plurality of cancer classes, the first plurality of reference subjects includes at least one subject that has the respective cancer class.

In some embodiments, each respective first bin count is representative of a number of nucleic acid fragments measured from cell-free nucleic acids in the biological sample obtained from the respective reference subject. The feasibility of using cell-free DNA to detect cancer is disclosed in Example 1 and Example 6.

In some embodiments, the first plurality of reference subjects is a training set.

In some embodiments, each respective first bin count is representative of a number of nucleic acid fragments measured from cell-free nucleic acids in the biological sample obtained from the respective reference subject.

In some embodiments, the sequencing construct for each respective reference subject in the first plurality of reference subjects is obtained by targeted panel or whole genome sequencing. In some such embodiments, the sequencing is performed by whole genome sequencing and the average coverage rate of the plurality of nucleic acid fragments taken from a biological sample from a reference subject is at least 1×, 2×, 3×, 4×, 5×, 6×, 7×, 8×, 9×, 10×, at least 20×, at least 30×, or at least 40× across the genome of the test subject. As disclosed in FIG. 3, each respective cancer class presents a distinct genomic signature, as revealed by whole genome sequencing data.

In some embodiments, the biological sample is processed to extract cell-free nucleic acids in preparation for sequencing analysis. By way of a non-limiting example, in some embodiments, cell-free nucleic acid is extracted from a blood sample collected from a subject in K2 EDTA tubes. Samples are processed within two hours of collection by double spinning of the blood first at ten minutes at 1000 g then plasma ten minutes at 2000 g. The plasma is then stored in 1 ml aliquots at −80° C. In this way, a suitable amount of plasma (e.g. 1-5 ml) is prepared from the biological sample for the purposes of cell-free nucleic acid extraction. In some such embodiments cell-free nucleic acid is extracted using the QIAamp Circulating Nucleic Acid kit (Qiagen) and eluted into DNA Suspension Buffer (Sigma). In some embodiments, the purified cell-free nucleic acid is stored at −20° C. until use. See, for example, Swanton, et al., 2017, "Phylogenetic ctDNA analysis depicts early stage lung cancer evolution," Nature, 545 (7655): 446-451, which is hereby incorporated by reference. Other equivalent methods can be used to prepare cell-free nucleic acid from biological methods for the purpose of sequencing, and all such methods are within the scope of the present disclosure.

In some embodiments, the cell-free nucleic acid that is obtained from the first biological sample is in any form of nucleic acid defined in the present disclosure, or a combination thereof. For example, in some embodiments, the cell-free nucleic acid that is obtained from a biological sample is a mixture of RNA and DNA.

In some embodiments the nucleic acid fragments obtained from cell-free nucleic acid of a biological sample comprise more than ten nucleic acid fragments, more than one hundred nucleic acid fragments, more than five hundred nucleic acid fragments, more than one thousand nucleic acid fragments, more than two thousand nucleic acid fragments, between twenty five hundred nucleic acid fragments and five thousand nucleic acid fragments, or more than five thousand nucleic acid fragments. In some embodiments, each of these nucleic acid fragments maps to a different portion of a reference genome. In some embodiments one nucleic acid fragment maps to all or a same portion of a region of a reference genome that another nucleic acid fragments maps to. In some embodiments one nucleic acid fragment maps to the exact same portion of a reference genome that another nucleic acid fragments maps to. In some embodiments more than one of the nucleic acid fragment maps have the same nucleic acid sequence and uniquely map to the exact same portion of a reference genome.

The time between obtaining a biological sample and performing an assay, such as a sequence assay, can be optimized to improve the sensitivity and/or specificity of the assay or method. In some embodiments, a biological sample can be obtained immediately before performing an assay. In some embodiments, a biological sample can be obtained, and stored for a period of time (e.g., hours, days or weeks) before performing an assay. In some embodiments, an assay can be performed on a sample within 1 day, 2 days, 3 days, 4 days, 5 days, 6 days, 1 week, 2 weeks, 3 weeks, 4 weeks, 5 weeks, 6 weeks, 7 weeks, 8 weeks, 3 months, 4 months, 5 months, 6 months, 1 year, or more than 1 year after obtaining the sample from the reference subject.

In some embodiments, sequence construct 126 for each respective reference subject in the plurality of reference subjects is obtained by targeted panel sequencing in which the nucleic acid fragments taken from a biological sample of a reference subject in order to form sequence construct 126 have at least 50,000× coverage for this targeted panel of genes, at least 55,000× coverage for this targeted panel of genes, at least 60,000× coverage for this targeted panel of genes, or at least 70,000× coverage for this targeted panel of genes. In some such embodiments, the targeted panel of genes is between 450 and 500 genes, between 2 and 30 genes, between 5 and 50 genes, between 10 and 100 genes, between 30 and 500 genes, or between 50 and 1000 genes. In some embodiments, the targeted panel of genes is within the range of 500±5 genes, within the range of 500±10 genes, or within the range 500±25 genes. In some embodiments, a bin count for targeted panel may be determined In some such embodiments, the targeted assay looks for single nucleotide variants in the targeted panel of genes, insertions in the targeted panel of genes, deletions in the targeted panel of genes, somatic copy number alterations (SCNAs) in the targeted panel of genes, or re-arrangements affecting the targeted panel of genes. In some embodiments, SCNAs can be detected from either WGBS or WGS data, as described in Example 7. In some embodiments, the test subject is human and the first feature is a single nucleotide variant count, an insertion mutation count, a deletion mutation count, or a nucleic acid rearrangement count across the human reference genome.

In some embodiments, sequence construct 126 for each respective reference subject in the plurality of reference subjects is obtained by a whole genome sequencing (WGS) assay. A whole genome sequencing assay refers to a physical assay that generates sequence reads for a whole genome or a substantial portion of the whole genome that can be used to determine large variations such as copy number variations or copy number aberrations. Such a physical assay may employ whole genome sequencing techniques or whole exome sequencing techniques. Sample methods for determining genetic variations relating to copy number variations or copy number aberrations can be found, for example, in U.S. patent application Ser. No. 16/352,739, entitled "Method and System for Selecting, Managing, and Analyzing Data of High Dimensionality," filed Mar. 13, 2019, which is hereby incorporated by reference.

In some embodiments, sequence construct 126 for each respective reference subject in the plurality of reference subjects is obtained by whole genome bisulfite sequencing (WGBS). Whole genome bisulfite sequencing data can be used to determine copy number variations or copy number aberrations because such data include genome sequencing information of a whole genome or a substantial portion of the whole genome. For example, bin counts and variations thereof can be determined similarly as disclosed herein in connection with whole genome sequencing data.

In some such embodiments, the whole genome bisulfite sequence variations identify one or more methylation state vectors in accordance with Example 4 below and as further disclosed in U.S. Patent Application No. 62/642,480, entitled "Methylation Fragment Anomaly Detection," filed Mar. 13, 2018, which is hereby incorporated by reference.

In some embodiments, sequence reads that are used for the identification of the nucleic acid fragments of genotypic data construct 126 are obtained in the manner described in the example assay protocol disclosed in Example 5.

In some embodiments, the sequence reads are pre-processed to correct biases or errors using one or more methods such as normalization, correction of GC biases, and/or correction of biases due to PCR over-amplification.

Any form of sequencing can be used to obtain the sequence reads from the cell-free nucleic acid obtained from a biological sample of a reference subject in order to form sequence construct 126 including, but not limited to, high-throughput sequencing systems such as the Roche 454 platform, the Applied Biosystems SOLID platform, the Helicos True Single Molecule DNA sequencing technology, the sequencing-by-hybridization platform from Affymetrix Inc., the single molecule, real-time (SMRT) technology of Pacific Biosciences, the sequencing-by-synthesis platforms from 454 Life Sciences, Illumina/Solexa and Helicos Biosciences, and the sequencing-by-ligation platform from Applied Biosystems. The ION TORRENT technology from Life technologies and nanopore sequencing also can be used to obtain sequence reads 140 from the cell-free nucleic acid obtained from the biological sample.

In some embodiments, sequencing-by-synthesis and reversible terminator-based sequencing (e.g., Illumina's Genome Analyzer; Genome Analyzer II; HISEQ 2000; HISEQ 2500 (Illumina, San Diego Calif.)) is used to obtain sequence reads from the cell-free nucleic acid obtained from a biological sample of a reference subject in order to form sequence construct 126. In some such embodiments, millions of cell-free nucleic acid (e.g., DNA) fragments are sequenced in parallel. In one example of this type of sequencing technology, a flow cell is used that contains an optically transparent slide with eight individual lanes on the surfaces of which are bound oligonucleotide anchors (e.g., adaptor primers). A flow cell often is a solid support that is configured to retain and/or allow the orderly passage of reagent solutions over bound analytes. In some instances, flow cells are planar in shape, optically transparent, generally in the millimeter or sub-millimeter scale, and often have channels or lanes in which the analyte/reagent interaction occurs. In some embodiments, a cell-free nucleic acid sample can include a signal or tag that facilitates detection. In some such embodiments, the acquisition of sequence reads, and thus the nucleic acid fragments, from the cell-free nucleic acid obtained from the biological sample includes obtaining quantification information of the signal or tag via a variety of techniques such as, for example, flow cytometry, quantitative polymerase chain reaction (qPCR), gel electrophoresis, gene-chip analysis, microarray, mass spectrometry, cytofluorimetric analysis, fluorescence microscopy, confocal laser scanning microscopy, laser scanning cytometry, affinity chromatography, manual batch mode separation, electric field suspension, sequencing, and combination thereof.

In some embodiments, each reference subject is any living or non-living organism, including but not limited to a human (e.g., a male human, female human, fetus, pregnant female, child, or the like), a non-human animal, a plant, a bacterium, a fungus or a protist. In some embodiments, test subject is a mammal, reptile, avian, amphibian, fish, ungulate, ruminant, bovine (e.g., cattle), equine (e.g., horse), caprine and ovine (e.g., sheep, goat), swine (e.g., pig), camelid (e.g., camel, llama, alpaca), monkey, ape (e.g., gorilla, chimpanzee), ursid (e.g., bear), poultry, dog, cat, mouse, rat, fish, dolphin, whale and shark. In some embodiments, the test subject is a male or female of any stage (e.g., a man, a women or a child).

In some embodiments, the plurality of cancer classes is two or more cancer classes selected from the group consisting of bladder cancer, brain cancer, breast cancer, colorectal cancer, endometrial cancer, esophageal cancer, head/neck cancer, kidney cancer, liver cancer, hematological cancer, lung cancer, a lymphoma, leukemia, a melanoma, a lymphoma, ovarian cancer, pancreatic cancer, prostate cancer, rectal cancer, renal cancer, thyroid cancer and uterine cancer.

In some embodiments, the plurality of cancer classes is five or more cancer classes selected from the group consisting of bladder cancer, brain cancer, breast cancer, colorectal cancer, endometrial cancer, esophageal cancer, head/neck cancer, kidney cancer, liver cancer, hematological cancer, lung cancer, a lymphoma, leukemia, a melanoma, a lymphoma, ovarian cancer, pancreatic cancer, prostate cancer, rectal cancer, renal cancer, thyroid cancer and uterine cancer.

In some embodiments, the biological sample or methylation biological sample obtained from the respective reference subject is a plasma sample from the respective reference subject, and the biological sample obtained from the test subject is a plasma sample from the test subject.

In some embodiments, the biological sample or methylation biological sample obtained from the respective reference subject comprises blood, whole blood, white blood cells, plasma, serum, urine, cerebrospinal fluid, fecal, saliva, sweat, tears, pleural fluid, pericardial fluid, or peritoneal fluid of the respective reference subject, and the biological sample obtained from the test subject comprises blood, whole blood, white blood cells, plasma, serum, urine, cerebrospinal fluid, fecal, saliva, sweat, tears, pleural fluid, pericardial fluid, or peritoneal fluid of the test subject.

In some embodiments, the biological sample or methylation biological sample obtained from the respective reference subject is a whole blood sample from the respective reference subject, and the nucleic acids in the biological sample or methylation biological sample obtained from the respective reference subject are genomic DNA.

In some embodiments, the first plurality of reference subjects comprises twenty subjects, and for each respective cancer class in the plurality of cancer classes, the first plurality of reference subjects includes at least two different subjects having the respective cancer class. In some embodiments, the first plurality of reference subjects comprises one hundred subjects, and for each respective cancer class in the plurality of cancer classes, the first plurality of reference subjects includes at least five different subjects in the respective cancer class.

In some embodiments, the first plurality of reference subjects comprises at least 20 subjects, at least 50 subjects, at least 100 subjects, at least 200 subjects, at least 500 subjects, at least 1000 subjects, or at least 2000 subjects. In some embodiments, for each respective cancer class in the plurality of cancer classes, the first plurality of reference subjects includes at least 3 different subjects in the respective cancer class, at least 4 different subjects in the respective cancer class, at least 5 different subjects in the respective cancer class, at least 6 different subjects in the respective cancer class, at least 7 different subjects in the respective cancer class, at least 8 different subjects in the respective cancer class, at least 9 different subjects in the respective cancer class, at least 10 different subjects in the respective cancer class, or at least 20 different subjects in the respective cancer class.

In some embodiments the species is human, and genotypic data construct 126 for the respective reference subject includes genotypic information for 22 autosomal chromosomes.

In some embodiments, the species is human, and genotypic data construct 126 for the respective reference subject includes genotypic information for less than 22 autosomal chromosomes.

Binning. In some embodiments, the plurality of bins comprises ten thousand bins, and the plurality of principal components (e.g., the plurality of features) consists of fewer than one hundred principal components. In some embodiments, the plurality of bins comprises up to 5,000 bins, up to 10,000 bins, up to 20,000 bins, up to 30,000 bins, up to 40,000 bins, up to 50,000 bins, or up to 60,000 bins. In some embodiments, the plurality of principal components consists of fewer than 10, fewer than 50, fewer than 100, fewer than 200, or fewer than 500 principal components.

In some embodiments, all or a portion of the genome (e.g., a set of targeted genomic regions) of the species is represented by a plurality of bins. In such embodiments, each respective bin in the plurality of bins represents a different and non-overlapping portion of the genome of a reference genome for the species.

In some embodiments, each such bin has the same size. In some embodiments, the bins can have different sizes. In some embodiments, a bin is defined by the number of nucleic acid residues within the bin. In some embodiments, a bin is defined by its location and the number of nucleic acids residues within the bin. Any suitable size range can be used to define a bin. For example, a bin can include 10 kb or fewer, 20 kb or fewer, 30 kb or fewer, 40 kb or fewer, 50 kb or fewer, 60 kb or fewer, 70 kb or fewer, 80 kb or fewer, 90 kb or fewer, 100 kb or fewer, 110 kb or fewer, 120 kb or fewer, 130 kb or fewer, 140 kb or fewer, 150 kb or fewer, 160 kb or fewer, 170 kb or fewer, 180 kb or fewer, 190 kb or fewer, 200 kb or fewer, or 250 kb or fewer nucleic acids.

In some embodiments targeted sequencing information of the genome of a species is represented by a plurality of bins. In some embodiments, each respective bin represents a number of nucleic acids residues. For example, a bin for targeted sequencing reads can include 10 kb or fewer, 20 kb or fewer, 30 kb or fewer, 40 kb or fewer, 50 kb or fewer, 60 kb or fewer, 70 kb or fewer, 80 kb or fewer, 90 kb or fewer, 100 kb or fewer, 110 kb or fewer, 120 kb or fewer, 130 kb or fewer, 140 kb or fewer, 150 kb or fewer, 160 kb or fewer, 170 kb or fewer, 180 kb or fewer, 190 kb or fewer, 200 kb or fewer, or 250 kb or fewer nucleic acids. In some embodiments, each respective bin represents a predetermined region of the genome, where the predetermined regions of the genome bins represent desired target regions (e.g., regions known to be associated with a particular disease).

Further in such embodiments, the genotypic information for each respective reference subject in the plurality of reference subjects comprises a first bin count for each respective bin in the plurality of bins, each respective first bin count representative of first genotypic information that has been measured from a biological sample obtained from the respective reference subject and that maps onto the different portions of the reference genome corresponding to the respective bin. For instance, in some such embodiments, the species is human and the plurality of bins is between one thousand bins and fifty thousand bins.

Figure 20:
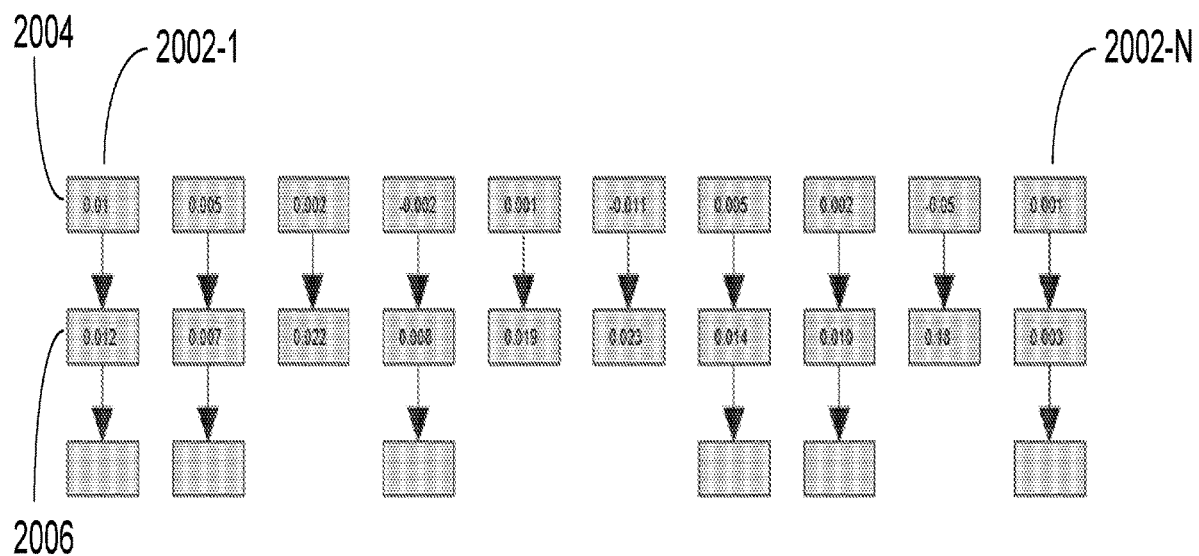
FIG. 20 illustrates a method of binning reference genomes, in accordance with some embodiments of the present disclosure.

In some embodiments, the first bin count representative of first genotypic information is a number of nucleic acid fragments in sequencing information measured from cell-free nucleic acid in the biological sample that maps onto the different portion of the genome of the species represented by the respective bin. In some such embodiments, this first bin count is in the form of B-scores, which are described in U.S. patent application Ser. No. 16/352,739, entitled "Method and System for Selecting, Managing, and Analyzing Data of High Dimensionality," filed Mar. 13, 2019, which is hereby incorporated by reference. Referring to FIG. 20, in the B-score method, there is a nucleic acid fragment count 2002 for each bin 2004 in the plurality of bins. Each bin represents a portion of the genome of the species. For example, in some embodiments, each bin uniquely represents 100 kilobases of the genome of the species. The nucleic acid fragment count reflects the number of nucleic acid fragments obtained from the biological sample of each reference subject in the plurality of reference subjects.

In some embodiments, such nucleic acid fragment counts are pre-processed to correct biases or errors using one or more methods such as normalization, correction of GC biases, and/or correction of biases due to PCR over-amplification. In some embodiments, the sequencing reads that are used to identify nucleic acid fragments are from whole genome sequencing, or targeted sequencing. As disclosed herein, sequencing can include but is not limited to nucleic acid sequencing (e.g., DNA, RNA, or hybrids or mixtures thereof), protein sequencing, sequence-based epigenetic analysis for analyzing protein-nucleic acid interactions (e.g., DNA or RNA methylation analysis, histone modification analysis, or combinations thereof), or protein-protein sequence modification analysis such as acetylation, methylation, ubiquitylation, phosphorylation, sumoylation, or combinations thereof.

Next, a data selection step is performed to select only a subset of bins. For instance, referring to FIG. 20 and as further described in Example 6, in some embodiments an interquartile range 2006 is computed for each respective bin 2002 in the plurality of bins using the nucleic acid fragment count across the plurality of reference subjects for the respective bin. Only the nucleic acid fragment count of those bins that exhibit low variance are retained for use in sequence construct 126. Additional methods for bin selection are disclosed in U.S. patent application Ser. No. 16/352, 739, entitled "Method and System for Selecting, Managing, and Analyzing Data of High Dimensionality," filed Mar. 13, 2019, which is hereby incorporated by reference. For example, a high variability filter can be created to allow one to discard bins corresponding to all genomic regions with bin variations above a threshold value. In other embodiments, a low variability filter can be created to focus subsequent analysis on data with data variations below a threshold. As an illustration, a human haploid reference genome includes over three billion bases that can be divided into about 30,000 regions (or bins). If an experimental value is observed for each bin, for example, a total number of nucleic acid fragments that align to the particular region or bin, each subject can have over 30,000 measurements. After a low or high variability filter is applied, the number of bin measurements corresponding to a subject can be reduced by a significant portion. For example, including but not limited to about 50% or less, about 45% or less, about 40% or less, about 35% or less, about 30% or less, about 25% or less, 20% or less, 15% or less, 10% or less, or 5% or less bins (by removing bins that fail to satisfy the filter). In some embodiments, the number of bin measurements corresponding to a subject can be reduced by 50% or more such as about 55%, 60%, 65%, or 70% or more. For example, a subject that originally has over 30,000 corresponding bin measurements, can have over 30% fewer bin measurements (e.g., about 20,000) after a high or low variability filter is applied.

In some embodiments, besides WGS data, copy number analysis is also applied to targeted sequencing data. In some embodiments, all or a portion of the targeted genomic regions (e.g., genes) in the genome of the species is represented by a plurality of bins. In such embodiments, each respective bin in the plurality of bins represents a different and non-overlapping set of the targeted genomic regions of a reference genome for the species. In some embodiments, each such bin has the same size. In some embodiments, the bins have different sizes. In some embodiments, a bin is defined by the number of targeted regions within the bin. In some embodiments, a bin is defined by its location and/or the number of targeted regions within the bin. Any suitable number of targeted genomic regions can be used to define a bin. In some example, a bin includes 10 or fewer, 20 or fewer, 30 or fewer, 40 or fewer, 50 or fewer, 60 or fewer, 70 or fewer, 80 or fewer, 90 or fewer, 100 or fewer, 200 or fewer, 500 or fewer, 1000 or fewer, 2500 or fewer, 5000 or fewer, 10,000 or fewer, or 50,000 or fewer targeted genes from a panel of target genes.

In some embodiments, copy number analysis is applied to methylation sequencing data such as WGBS or targeted methylation sequencing data. For example, for WGBS data, the reference genome can be binned in a manner similar to that of a WGS analysis: each respective bin in the plurality of bins represents a different and non-overlapping set of a reference genome for the species.

As disclosed herein, data obtained from any sequencing data (e.g., from sequencing using a targeted panel, WGS or WGBS) can be binned in any possible way so long as data from the test samples and data from the reference samples are binned similarly. In some embodiments, each such bin has the same size. In some embodiments, the bins have different sizes.

In some embodiments, the methylation information embedded in the sequencing data are used in conjunction with the somatic copy number analysis as disclosed herein, as illustrated in FIGS. 10 through 13. As illustrated, some cancer patients that were not identified by WGS analysis (copy number changes) can be correctly classified by methylation analysis. Additional methods for determining bin counts for methylation states are disclosed in U.S. Provisional Patent Application No. 62/642,480, entitled "Methylation Fragment Anomaly Detection," filed Mar. 13, 2018, which is hereby incorporated by reference. For example, a methylation state vector is generated for each nucleic acid fragment from a methylation biological sample. The accumulated methylation state vectors will determine the counts for each methylation site in each bin.

In some embodiments, the first bin count representative of first genotypic information is a number of nucleic acid fragments in sequencing information measured from white blood cells in the biological sample that maps onto the different portion (e.g., where the different regions are defined either by numerical position or by targeted locations) of the genome of the species represented by the respective bin.

In some embodiments, the first bin count representative of first genotypic information is a respective first number of nucleic acid fragments that are validated using paired sequence reads in sequencing information measured from cell-free nucleic acid in the biological sample that map onto the different portion of the genome of the species represented by the respective bin, where each paired sequence read of the paired sequence reads maps to a sequence in the portion of the genome of the species that is within a first size range.

In some embodiments, the first bin count representative of first genotypic information is a number of fragments, measured by whole genome bisulfite sequencing of cell-free nucleic acid in the biological sample or methylation biological sample that maps onto the different portion of the genome of the species represented by the respective bin.

In some embodiments, the first bin count representative of first genotypic information is a mean fragment length of the nucleic acid fragments derived from sequencing information measured from cell-free nucleic acid in the biological sample that maps onto the different portions of the genome of the species represented by the respective bin.

In some embodiments, the first bin count representative of first genotypic information is an allelic ratio of nucleic acid fragments measured from cell-free nucleic acid in the biological sample mapping onto the different portion of the genome of the species represented by the respective bin.

In some embodiments, the first bin count representative of first genotypic information is a number of mutations identified in nucleic acid fragments measured from cell-free nucleic acid in the biological sample mapping onto the different portion of the genome of the species represented by the respective bin.

In some embodiments, the first bin count representative of first genotypic information is a number of fragments, measured by targeted genomic sequencing of cell-free nucleic acid in the biological sample that maps onto the different portion of the genome of the species represented by the respective bin.

In some embodiments, the sequencing construct for the respective reference subject further includes a second bin count for each respective bin in the plurality of bins. In some embodiments, each respective second bin count is representative of a number of nucleic acid fragments that are in a second size range that were measured from nucleic acids in the biological sample obtained from the respective reference subject that maps onto the different and non-overlapping portion of the reference genome. In some embodiments, each respective first bin count representative of a number of nucleic acid fragments that are in a first size range that were measured from nucleic acids in the biological sample obtained from the respective reference subject that maps onto the different and non-overlapping portion of the reference genome. In some such embodiments, collectively subjecting the value training set to an unstrained classifier further provides the second bin count of each bin in each respective plurality of bins across the first plurality of reference subjects to the dimensionality reduction method, thereby obtaining the feature set, and the first size range is different than the second size range.

In some embodiments, the sequencing construct for the respective reference subject includes a respective set of bin counts for each respective bin in the plurality of bins, where the respective set of bin counts includes the first bin count, and wherein each respective bin count in the respective set of bin counts is representative of a number of nucleic acid fragments that are in a size range corresponding to the respective bin count that were measured from nucleic acids in the biological sample obtained from the respective reference subject that maps onto the different and non-overlapping portion of the reference genome. In some such embodiments, collectively subjecting the value training set to an unstrained classifier provides the respective set of bin counts of each bin in the plurality of bins across the first plurality of reference subjects to the dimensionality reduction method, thereby obtaining the feature set. In some embodiments, the respective set of bins includes at least three different bin counts, where each bin count in the respective set of bin counts corresponds to a different size range.

Block 208. The method proceeds to collectively subject the first bin count of each bin in the plurality of bins for each reference subject in the first plurality of reference subjects to a dimensionality reduction method thereby obtaining a feature set, where the feature set consists of a number of features that is fewer than the number of bins in the plurality of bins, and where the dimensionality reduction method yields a value training set comprising a value for each feature in the feature set for each reference subject in the first plurality of reference subjects.

In some embodiments, the dimensionality reduction method comprises application of a Gaussian process regression using the cancer class and the respective sequencing construct of each corresponding reference subject in the first plurality of reference subjects, which includes the first bin counts for each bin in the plurality of bins for the corresponding reference subject. In some embodiments, the dimensionality reduction method comprises application of a dimension reduction method using the cancer class and the respective sequencing construct of each corresponding reference subject in the first plurality of reference subjects, which includes the first bin counts for each bin in the plurality of bins for the corresponding reference subject, where the dimension reduction method is a subset selection method (e.g., as disclosed in Hastie, 2001, *The Elements of Statistical Learning*, Springer, New York, pp. 55-57), a discrete method (e.g., as disclosed in Furnival & Wilson, 1974, "Regression by Leaps and Bounds," Technometrics 16 (4), 499-511), forward/backward stepwise selection (e.g., as disclosed in Berk, 1978, "Comparing Subset Regression Procedures," Technometrics 20:1, 1-6), a shrinkage method (e.g., as disclosed in Hastie, 2001, *The Elements of Statistical Learning*, Springer, New York, pp. 59-66), a ridge regression (e.g., as disclosed in Hastie, 2001, *The Elements of Statistical Learning*, Springer, New York, pp. 59-64), a lasso technique (e.g., as disclosed in Hastie, 2001, *The Elements of Statistical Learning*, Springer, New York, pp. 64-65, 69-72, 330-331), a derived input direction method (e.g., principal component regression (PCR), partial least squares (PLS), etc. as disclosed, for example, in Viyayakurma and Schaal, 2000, "Locally Weighted Projection Regression: An O (n) Algorithm for Incremental Real Time Learning in High Dimensional Space, Proc. of Seventeenth International Conference on Machine Learning (ICML2000), pp. 1079-1086), or combinations thereof, to thereby reduce the dimensionality of the data (the first bin count across the plurality of bins) down to a certain number of dimensions (e.g., between ten dimension and one hundred of dimensions, between fifty and five hundred dimensions, between one hundred and one thousand dimensions, or some other suitable number of dimensions). Such dimension reduction advantageously improves the computational efficiency of system 100.

In some embodiments, a first feature is associated with a call made by a B-score classifier described in U.S. patent Publication Ser. No. 16/352,739, entitled "Method and System for Selecting, Managing, and Analyzing Data of High Dimensionality," filed Mar. 13, 2019, which is hereby incorporated by reference. As disclosed herein, in some embodiments B-scores are determined based on whole genome sequencing data, whole genome bisulfite sequencing data, or targeted sequencing data.

In accordance with the B-score method, a first set of nucleic acid fragments of nucleic acid samples from healthy subjects in a reference group of healthy subjects are analyzed for regions of low variability. Accordingly, each nucleic acid fragment in the first set of nucleic acid fragments of nucleic acid samples from each healthy subject are aligned to a region in the reference genome. From this, a training set of nucleic acid fragments from nucleic acid fragments of nucleic acid samples from subjects in a training group is selected. Each nucleic acid fragment in the training set aligns to a region in the regions of low variability in the reference genome identified from the reference set. The training set includes nucleic acid fragments of nucleic acid samples from healthy subjects as well as nucleic acid fragments of nucleic acid samples from diseased subjects who are known to have the cancer. The nucleic acid samples from the training group are of a type that is the same as or similar to that of the nucleic acid samples from the reference group of healthy subjects. From this it is determined, using quantities derived from nucleic acid fragments of the training set, one or more parameters (e.g., the value training set) that reflect differences between nucleic acid fragments of nucleic acid samples from the healthy subjects and nucleic acid fragments of nucleic acid samples from the diseased subjects within the training group. Then, a test set of nucleic acid fragments associated with nucleic acid samples comprising cfDNA fragments from a test subject whose status with respect to cancer is unknown is received, and the likelihood of the test subject being in one or more of a plurality of cancer classes is determined based on the one or more parameters.

In some embodiments, a first feature is associated with a call made by a M-score classifier is described in U.S. Patent Application No. 62/642,480, entitled "Methylation Fragment Anomaly Detection," filed Mar. 13, 2018, which is hereby incorporated by reference.

In some embodiments, a first feature is obtained from any of the disclosed methods or algorithms in U.S. patent application Ser. No. 15/793,830, filed Oct. 25, 2017, and/or International Patent Publication No. PCT/US17/58099, having an International Filing Date of Oct. 24, 2017, each of which is hereby incorporated by reference.

In some embodiments, the method further comprises scaling (e.g., normalizing) the first bin count for each respective bin in the plurality of bins for each respective reference subject in the first plurality of reference subjects by: (i) taking a log transformation of the respective first bin count thereby forming a log transformed first bin count for the respective bin, (ii) subtracting a mean value of the respective log transformed first bin count across the first plurality of reference subjects from the log transformed first bin count of the respective bin thereby forming a first normalized first bin count for the respective bin, and, subsequently (iii) dividing the respective first normalized first bin count for the respective bin by a standard deviation of the first normalized bin first count across the first plurality of reference subjects thereby scaling the first bin count for each respective bin in the plurality of bins for each respective reference subject in the first plurality of reference subjects. In some embodiments, such scaling is performed prior to performing dimension reduction.

In some alternative embodiments, the method further comprises scaling (e.g., normalizing) the individual features of the above-described dimension reduced feature set. In some such embodiments, this is done by: (i) taking a log transformation of a respective feature thereby forming a log transformed first feature value for the first feature, (ii) subtracting a mean value of the respective log transformed first feature value across the first plurality of reference subjects from the log transformed first feature of the respective feature thereby forming a first normalized first feature value for the respective feature, and, subsequently (iii) dividing the respective first normalized first feature value for the respective feature by a standard deviation of the first normalized first feature value across the plurality of reference subjects thereby scaling the first feature value for each respective feature in the feature set for each respective reference subject in the plurality of reference subjects.

In some embodiments, the sequencing construct for the respective reference subject further includes a second bin count for each respective bin in the plurality of bins, with each respective second bin count being representative of a number of nucleic acid fragments that are in a second size range that were measured from nucleic acids in the biological sample obtained from the respective reference subject that maps onto the different and non-overlapping portion of the reference genome. In some embodiments, each respective first bin count is representative of a number of nucleic acid fragments that are in a first size range that were measured from nucleic acids in the biological sample obtained from the respective reference subject that maps onto the different and non-overlapping portion of the reference genome. By way of example, in some embodiments the first size range represents nucleic acid fragments that are between 1000 bases and 10,000 bases whereas the second size range represents nucleic acid fragments that are larger than 10,000 bases. The exact size of the first size range and the second size range is application dependent. For instance, it depends on the type of sequencing method that is used to measure the sequencing reads and more specifically the average nucleic acid fragment length produced by the sequencing method. Moreover, in some embodiments the first size range and the second size range are dynamically determined with a given training set in a way that is optimal for the dataset. For instance, the first size range and the second size range is optimized in some embodiments so that the number of nucleic acid fragments across the training set that collectively fall in the first size range across the bins is approximately equal to the number sequencing reads across the training set that collectively fall into the second size range across the bins.

In some embodiments, collectively subjecting the first bin count of each bin in the plurality of bins to a dimensionality reduction method further provides that a second bin count of each bin in each respective plurality of bins for each reference subject in the first plurality of reference subjects is also subjected to the dimensionality reduction method to obtaining the feature set. In some embodiments, such dimension reduction is independently performed. That is, the first bin count of each bin in the plurality of bins is subject to a first dimensionality reduction method to obtain a first set of dimension reduction components and the second bin count of each bin in the plurality of bins is subject to a second dimensionality reduction method to obtain a second set of dimension reduction components, where the first dimension reduction method is the same or different than the second dimensionality reduction method. In other embodiments, such dimension reduction is jointly performed. That is, the first and second bin count of each bin in the plurality of bins is subject to a single dimensionality reduction method to obtain a set of dimension reduction components.

In some embodiments, as discussed above the first size range is different than the second size range. In other embodiments, the first size range is a subset of the second size range. In still other embodiments, the first size range overlaps the second size range.

In some embodiments, the sequencing construct for the respective reference subject includes a respective set of bin counts for each respective bin in the plurality of bins. In some embodiments, the respective set of bin counts includes the first bin count, and each respective bin count in the respective set of bin counts is representative of a number of nucleic acid fragments that are in a size range corresponding to the respective bin count that were measured from nucleic acids in the biological sample obtained from the respective reference subject that maps onto the different and non-overlapping portion of the reference genome.

In some embodiments, the step of collectively subjecting the first bin count of each bin in the plurality of bins to a dimensionality reduction method provides the respective set of bin counts of each bin in the plurality of bins for each reference subject in the first plurality of reference subjects to the dimensionality reduction method thereby obtaining the feature set. In some embodiments, such dimension reduction is independently performed. That is, the first bin count of each bin in the plurality of bins is subject to a first dimensionality reduction method to obtain a first set of dimension reduction components, the second bin count of each bin in the plurality of bins is subject to a second dimensionality reduction method to obtain a second set of dimension reduction components, and so forth where the first dimension reduction method is the same or different than the second dimensionality reduction method, and so forth In other embodiments, such dimension reduction is jointly performed. That is, the respective set of bin counts bin counts of each bin in the plurality of bins is subject to a single dimensionality reduction method to obtain a set of dimension reduction components.

In some embodiments, the respective set of bins includes at least three different bin counts, and each bin count in the respective set of bin counts corresponds to a different size range. In some embodiments, the respective set of bins includes at least 4, at least 5, at least 6, at least 7, at least 8, at least 9, at least 10, at least 15, at least 20, or at least 50 different bin counts. The number of bin counts for each respective set of bins will be greater than zero. In some such embodiments, each respective bin count is representative of a number of nucleic acid fragments that are in a size range corresponding to the bin count that were measured from nucleic acids in the biological sample obtained from the respective reference subject that maps onto the different and non-overlapping portion of the reference genome. The exact size of each size range is application dependent. For instance, it depends on the type of sequencing method that is used to measure the sequencing reads and more specifically the average nucleic acid fragment length produced by the sequencing method. Moreover, in some embodiments size ranges are dynamically determined with a given training set in a way that is optimal for the dataset. For instance, in some embodiments, each size range is optimized so that the number of nucleic acid fragments across the training set that collectively fall in each respective size range across the bins is approximately equal.

Block 210. The value training set is used as collective input to an untrained first classifier, in conjunction with the cancer class of each respective reference subject in the first plurality of reference subjects as ground truth, to train the untrained first classifier on cancer class thereby obtaining a trained first classifier.

In some embodiments, the untrained first classifier is a multinomial classifier that provides a plurality of likelihoods responsive to the nucleic acid fragments obtained from cell-free nucleic acids from the test subject, where each respective likelihood in the plurality of likelihoods is a likelihood that the test subject has a corresponding cancer class in the plurality of cancer classes.

In some embodiments, the test subject is deemed to have either a first cancer class or a second cancer class in the plurality of cancer classes, the first cancer class is the cancer class having the highest likelihood in the plurality of likelihoods, and the second cancer class is the cancer class having the second highest likelihood in the plurality of likelihoods.

In some embodiments, the test subject is deemed to have either a first cancer class, a second cancer class, or a third cancer class in the plurality of cancer classes. In such embodiments, the first cancer class is the cancer class having the highest likelihood in the plurality of likelihoods, the second cancer class is the cancer class having the second highest likelihood in the plurality of likelihoods, and the third cancer class is the cancer class having the third highest likelihood in the plurality of likelihoods.

In some embodiments, the untrained first classifier is based on a multinomial logistic regression algorithm. In some embodiments, the untrained first classifier is based on a neural network algorithm, a support vector machine algorithm, a Naive Bayes algorithm, a nearest-neighbor algorithm, a boosted trees algorithm, a random forest algorithm, or a decision tree algorithm.

Logistic regression algorithms that can serve as the untrained first classifier for the instant methods are disclosed in Agresti, An *Introduction to Categorical Data Analysis,* 1996, Chapter 5, pp. 103-144, John Wiley & Son, New York, which is hereby incorporated by reference.

Neural network algorithms, including convolutional neural network algorithms, that can serve as the untrained classifier for the instant methods are disclosed in See, Vincent et al., 2010, "Stacked denoising autoencoders: Learning useful representations in a deep network with a local denoising criterion," J Mach Learn Res 11, pp. 3371-3408; Larochelle et al., 2009, "Exploring strategies for training deep neural networks," J Mach Learn Res 10, pp. 1-40; and Hassoun, 1995, Fundamentals of Artificial Neural Networks, Massachusetts Institute of Technology, each of which is hereby incorporated by reference.

SVM algorithms that can serve as the untrained classifier for the instant methods are described in Cristianini and Shawe-Taylor, 2000, "An Introduction to Support Vector Machines," Cambridge University Press, Cambridge; Boser et al., 1992, "A training algorithm for optimal margin classifiers," in Proceedings of the 5th Annual ACM Workshop on Computational Learning Theory, ACM Press, Pittsburgh, Pa., pp. 142-152; Vapnik, 1998, *Statistical Learning Theory*, Wiley, New York; Mount, 2001, *Bioinformatics: sequence and genome analysis*, Cold Spring Harbor Laboratory Press, Cold Spring Harbor, N.Y.; Duda, *Pattern Classification*, Second Edition, 2001, John Wiley & Sons, Inc., pp. 259, 262-265; and Hastie, 2001, *The Elements of Statistical Learning*, Springer, New York; and Furey et al., 2000, *Bioinformatics* 16, 906-914, each of which is hereby incorporated by reference in its entirety. When used for classification, SVMs separate a given set of binary labeled data training set with a hyper-plane that is maximally distant from the labeled data. For cases in which no linear separation is possible, SVMs can work in combination with the technique of 'kernels', which automatically realizes a non-linear mapping to a feature space. The hyper-plane found by the SVM in feature space corresponds to a non-linear decision boundary in the input space.

Decision trees that can serve as the untrained classifier for the instant methods are described generally by Duda, 2001, *Pattern Classification*, John Wiley & Sons, Inc., New York, pp. 395-396, which is hereby incorporated by reference. Tree-based methods partition the feature space into a set of rectangles, and then fit a model (like a constant) in each one. In some embodiments, the decision tree is random forest regression. One specific algorithm that can serve as the classifier for the instant methods is a classification and regression tree (CART). Other specific decision tree algorithms that can serve as the classifier for the instant methods include, but are not limited to, ID3, C4.5, MART, and Random Forests. CART, ID3, and C4.5 are described in Duda, 2001, *Pattern Classification*, John Wiley & Sons, Inc., New York, pp. 396-408 and pp. 411-412, which is hereby incorporated by reference. CART, MART, and C4.5 are described in Hastie et al., 2001, *The Elements of Statistical Learning*, Springer-Verlag, New York, Chapter 9, which is hereby incorporated by reference in its entirety. Random Forests are described in Breiman, 1999, "Random Forests-Random Features," Technical Report 567, Statistics Department, U.C. Berkeley, September 1999, which is hereby incorporated by reference in its entirety.

Figure 4:
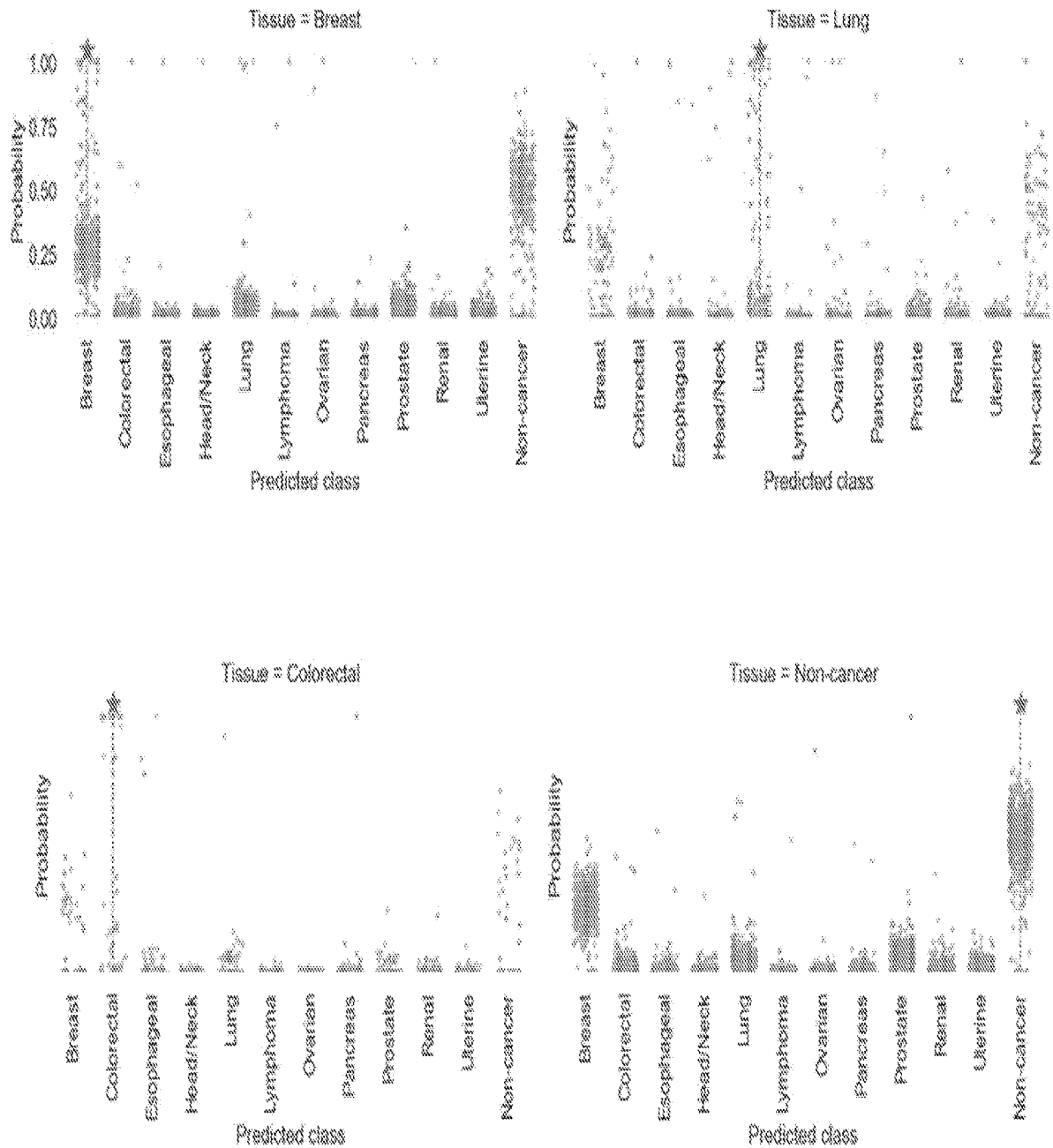
FIG. 4 illustrates the use of whole genome sequencing data to predict the probability of cancer tissue type for each subject in accordance with some embodiments of the present disclosure.

Block 212. The trained first classifier is used to classify the test subject to a cancer class in the plurality of cancer classes using nucleic acid fragments of nucleic acids in a biological sample obtained from the test subject. FIG. 4 displays an example of a trained classifier that has calculated probabilities (e.g., classified) for subjects by cancer class.

In some embodiments, using the trained first classifier combines a first call on cancer class made by the trained first classifier for the test subject with a second call made by a trained second classifier, the trained second classifier is trained using a respective methylation pattern measured in a respective reference methylation biological sample from each reference subject in a second plurality of reference subjects, and input to the second trained classifier for the second call comprises a methylation pattern measured in a methylation biological sample obtained from the test subject. In some embodiments, the first trained classifier comprises a plurality of component classifiers formed by resampling the feature training set a plurality of times. In some embodiments, the resampling comprises an arcing technique (e.g., bagging or boosting the feature training set a plurality of times thereby forming the plurality of component classifiers). In some embodiment, the resampling comprises a bootstrap technique.

In some embodiments, the bootstrap technique comprises (i) for each respective iteration in a plurality of iterations, forming a corresponding trained first component classifier by a procedure that comprises: (a) omitting from the feature training set a value for each feature in the feature set for each reference subject in a different portion of the first plurality of reference subjects, and (b) inputting the remaining portion of the feature training set as collective input to a respective untrained first component classifier, in conjunction with the cancer class of each respective reference subject in the first plurality of reference subjects represented by the remaining portion of the feature training set as ground truth, to train the respective untrained first component classifier on cancer class thereby obtaining a respective trained first component classifier. This, thus, forms a plurality of trained first component classifiers. In some embodiments, the bootstrap technique further comprises (ii) estimating a performance of the first trained classifier as an average performance of the plurality of trained first component classifiers.

In some embodiments, each component classifier in the plurality of component classifiers provides a single vote to the determination of the classification of the test subject to the cancer class in the plurality of cancer classes using nucleic acid fragments of cell-free nucleic acids in the biological sample or methylation biological sample obtained from the test subject.

In some embodiments, the methylation biological sample comprises cell-free nucleic acids. In some embodiments, the reference methylation biological sample comprises cell-free nucleic acids. In some embodiments, the methylation biological sample is the same as the reference methylation biological sample.

In some embodiments, the test subject is deemed to have a first cancer class in the plurality of cancer classes when both the first call and the second call identify the test subject as having the same cancer class in the plurality of cancer classes. In some embodiments, the test subject is deemed to have a first cancer class in the plurality of cancer classes when both the first call and the second call identify the test subject as having the same type of cancer. In some embodiments, the test subject is deemed to have a first cancer class in the plurality of cancer classes when both the first call and the second call identify the test subject as having the same stage and the same type of cancer.

In some embodiments, the test subject is deemed to have a first cancer class in the plurality of cancer classes when (i) the trained first classifier calls the first cancer class with a higher probability than all other cancer classes in the plurality of cancer classes and (ii) the second call identifies the test subject as having the first cancer class.

In some embodiments, the test subject is deemed to have a first cancer class in the plurality of cancer classes when (i) the first trained classifier calls the first cancer class with a call that is among the top two cancer classes in the plurality of cancer classes in terms of probability and (ii) the second call identifies the test subject as having the first cancer class. In some embodiments, the test subject is deemed to have a first cancer class in the plurality of cancer classes when (i) the first trained classifier calls the first cancer class with a call that is among the top three cancer classes in the plurality of cancer classes in terms of probability and (ii) the second call identifies the test subject as having the first cancer class. In some embodiments, the test subject is deemed to have a first cancer class in the plurality of cancer classes when (i) the first trained classifier calls the first cancer class with a call that is among the top four cancer classes in the plurality of cancer classes in terms of probability and (ii) the second call identifies the test subject as having the first cancer class.

In some embodiments, the test subject is deemed to have a first cancer class in the plurality of cancer classes when (i) the first trained classifier calls the first cancer class with a higher probability than all other cancer classes in the plurality of cancer classes and (ii) the second trained classifier calls the first cancer class with a higher probability than all other cancer classes in the plurality of cancer classes.

In some embodiments, the test subject is deemed to have a first cancer class in the plurality of cancer classes when (i) the first trained classifier calls the first cancer class with a call that is among the top two cancer classes in the plurality of cancer classes in terms of probability and (ii) the second trained classifier calls the first cancer class with a call that is among the top two cancer classes in the plurality of cancer classes in terms of probability.

In some embodiments, the first plurality of reference subjects and the second plurality of reference subjects are the same plurality of subjects.

In some embodiments, the second plurality of reference subjects comprises a subset of the first plurality of reference subjects. In some embodiments, the second plurality of reference subjects is completely distinct from (e.g., does not overlap with) the first plurality of reference subjects.

In some embodiments, a cancer class comprises a cancer type (e.g., a reference subject has a specific cancer type and is not in the cancer class of "non-cancer").

In some embodiments, as further described in Example 2 below, each reference subject in the first plurality of reference subjects has breast cancer, colorectal cancer, esophageal cancer, head/neck cancer, lung cancer, a lymphoma, ovarian cancer, pancreatic cancer, prostate cancer, renal cancer, or uterine cancer. In some such embodiments, the obtaining of a cancer type and sequencing construct for each reference subject in the plurality of subjects further comprises, for each respective reference subject in the first plurality of reference subjects, predicting a stage of the cancer type of the respective reference subject. In some embodiments, the using the training set as a collective input to an untrained classifier further uses the stage of the cancer type of each respective reference subject in the first plurality of reference subjects as ground truth, to train the untrained first classifier on cancer type thereby obtaining the trained first classifier. Correspondingly, in some embodiments, the trained first classifier classifies a test subject with respect to the cancer type in a plurality of cancer types as well as a cancer type stage using nucleic acid fragments obtained from cell-free nucleic acids in the biological sample obtained from the test subject.

In some embodiments, each reference subject in the first plurality of reference subjects has a cancer in an enumerated set of cancer types. In some embodiments this enumerated set of cancer types is two or more, three or more, four or more, five or more, six or more, seven or more, or eight or more of the group consisting of bladder cancer, brain cancer, breast cancer, colorectal cancer, endometrial cancer, esophageal cancer, head/neck cancer, kidney cancer, liver cancer, hematological cancer, lung cancer, a lymphoma, leukemia, a melanoma, a lymphoma, ovarian cancer, pancreatic cancer, prostate cancer, rectal cancer, renal cancer, thyroid cancer and uterine cancer. Additionally, in some embodiments the set of cancer types includes other cancer types. In still other embodiments, the set of cancer types further in broken down into cancer stages. In such instances, for example, stage 3 breast cancer and stage 4 breast cancer would be considered two different cancer types. Thus, in some such embodiments, the obtaining of a cancer type and sequencing construct for each reference subject in the plurality of subjects further comprises, for each respective reference subject in the first plurality of reference subjects, predicting a stage of the cancer type of the respective reference subject. In some embodiments, the using the training set as a collective input to an untrained classifier further uses the stage of the cancer type of each respective reference subject in the first plurality of reference subjects as ground truth, to train the untrained first classifier on cancer type thereby obtaining the trained first classifier. Correspondingly, in some embodiments, the trained first classifier classifies a test subject with respect to the cancer type in a plurality of cancer types as well as a cancer type stage using nucleic acid fragments obtained from cell-free nucleic acids in the biological sample obtained from the test subject.

In some embodiments, the obtaining of a cancer class and sequencing construct for each reference subject in the plurality of subjects further comprises, for each respective reference subject in the first plurality of reference subjects, an indication of whether a predetermined genetic marker is absent or present in the respective reference subject. In some embodiments, using the value training set as a collective input to an untrained classifier further uses the indication of whether the predetermined genetic marker is absent or present in each respective reference subject in the first plurality of reference subjects as ground truth, to train the untrained first classifier on cancer class and cancer aggressiveness thereby obtaining the trained first classifier. In some embodiments, using the first trained classifier uses the trained first classifier to classify the test subject to the cancer class in the plurality of cancer classes and an aggressiveness of the cancer class using (i) nucleic acid fragments of cell-free nucleic acids in the biological sample or methylation biological sample obtained from the test subject and (ii) an indication of whether the predetermined genetic marker is absent or present in the test subject. In some embodiments the aggressiveness of a cancer is quantified by a 3-year relative survival rate, a 5-year relative survival rate, or a 10-year relative survival rate. Thus, a cancer that has a lower 3-year relative survival rate will be deemed to be a more aggressive cancer than a cancer that has a higher 3-year relative survival rate.

In some embodiments, the (predetermined) genetic marker is a single nucleotide variant associated with a predetermined genomic location, an insertion mutation associated with predetermined genomic location, a deletion mutation associated with a predetermined genomic location, a somatic copy number alteration, a nucleic acid rearrangement associated with a predetermined genomic locus, or an aberrant methylation pattern associated with a predetermined genomic location. In some such embodiments, this first feature is identified using any of the methods disclosed in U.S. Patent Application No. 62/658,479, entitled "Systems and Methods for Classifying Subjects Using Frequencies of Variants in Cell-Free Nucleic Acid," filed Apr. 16, 2018, which is hereby incorporated by reference. In some embodiments, more than one genetic marker is used. In some embodiments, two or more genetic markers are independently used, three or more genetic markers are independently used, four or more genetic markers are independently used, or five or more genetic markers are independently used. As a further example of genetic markers, in the case where one of the cancers under consideration is colorectal cancer, the genetic markers that may be used in some embodiments of the present disclosure are described in Walther, 2009, "Genetic prognostic and predictive markers in colorectal cancer," Nature Reviews Cancer 9, 489-499, which is hereby incorporated by reference. As a further example of genetic markers, in the case where one of the cancers under consideration is acute lymphoblastic leukemia, the genetic markers that may be used in some embodiments of the present disclosure are described in Rubnitz, 1997, "TEL gene rearrangement in acute lymphoblastic leukemia: a new genetic marker with prognostic significance," Journal of Clinical Oncology 15 (3), 1150-1157, which is hereby incorporated by reference.

In some embodiments, a different set of genetic markers is used for each cancer class in the set of cancer classes. For instance, in some embodiments, a first cancer class is precursor B Lymphoblastic Leukemia and the set of genetic markers for the first cancer class are as set forth in the Cancer Gene Markers Database on the Internet at cgmd.in, while a second cancer class is precursor T Lymphoblastic Leukemia and the set of genetic markers for the second cancer class are likewise set forth in the Cancer Gene Markers Database on the Internet at cgmd.in. See also Pradeepkiran et al., 2015, "CGMD: An integrated database of cancer genes and markers," Nature 5:12035, which is hereby incorporated by reference. In still further embodiments, the training of the classifier, in addition to the binned and normalized nucleic acid fragment counts, uses a different set of genetic markers for two or more stages of one or more cancer classes in the set of cancer classes to train the classifier. In such embodiments, the classifier training may further use more than one nucleic acid fragment count for each bin of each training subject, where such separate bin counts represent different nucleic acid fragment size counts as discussed above.

In some embodiments, a first call on cancer class made by the trained first classifier for the test subject is combined with a second call made by a trained second classifier. This is further disclosed in Example 3 and FIGS. 9A, 9B, 9C, and 24.

In some embodiments, the trained second classifier is trained using a respective methylation pattern measured in cell-free nucleic acids obtained from a respective methylation biological sample from each reference subject in a second plurality of reference subjects. In some embodiments, input to the second trained classifier for the second call comprises a methylation pattern measured in cell-free nucleic acids obtained from the test subject. Example 3 also discloses the combination of whole genome sequencing classifiers with methylation-trained classifiers (see FIGS. 10A, 10B, 10C, 11, 12, 13A, 13B, and 13C).

In some embodiments, the trained first classifier is trained on a specific fraction of the plurality of reference subjects. As described in Example 3 and FIG. 14, the accuracy of the trained first classifier may, in some embodiments, depend on the fraction of the plurality of reference subjects used in training the classifier.

In some embodiments, the method further comprises administering a treatment to a test subject based upon the cancer class of the test subject determined by the first trained classifier. In other words, the treatment is a treatment that is a known treatment for the cancer class the first trained classifier determines the test subject has. For instance, knowing the cancer class of the test subject provides a basis for determining which treatment regimen to provide the test subject using resourses such as those provided by the American Society of Clinical Oncology (ASCO, the Internet at www.asco.org/practice-guidelines/quality-guidelines/guidelines), the National Cancer Institute (www.cancer.gov), and related institutions.

Figure 3:
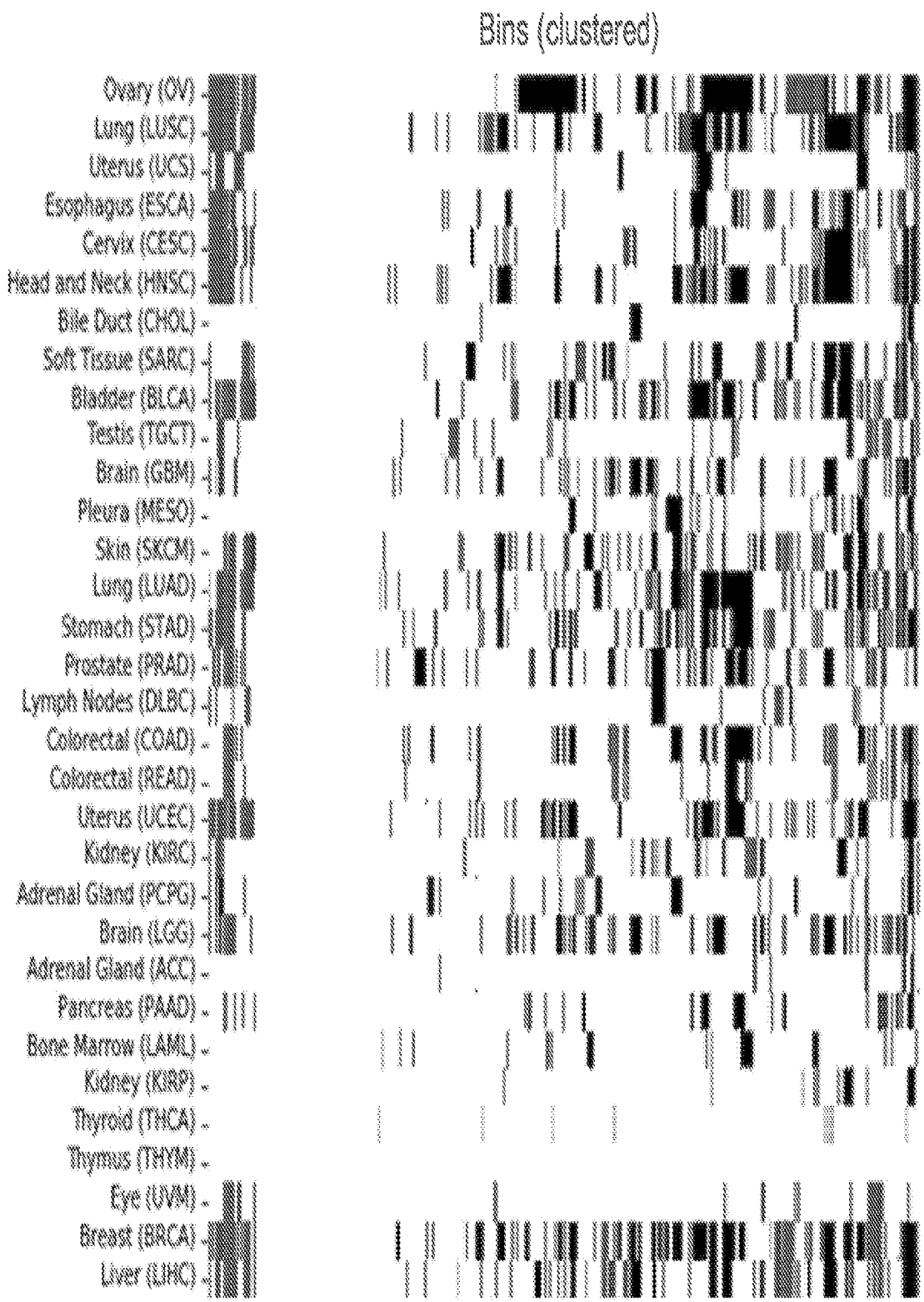
FIG. 3 illustrates the association of various cancers with distinct genomic signatures based on whole genome sequencing data, which is here represented by the clustered bins, where each bin corresponds to a particular region of the genome in accordance with some embodiments of the present disclosure.

Example 1—Different cancer classes exhibit patterns in cell-free whole genome sequencing data. FIGS. 3 and 4 disclose the usefulness of whole genome sequencing data for classifying subjects to a cancer class, according to an embodiment in accordance with the present disclosure. For whole genome sequencing data to be useful for classifying cancer classes, the data must convey information that is distinct to each cancer class. With FIG. 3, differences between cancer classes are disclosed and with FIG. 4, classifiers are trained on this data and used to predict cancer class for a plurality of test subjects. Thus, as discussed below, FIGS. 3 and 4 show that whole genome sequencing provides sufficient information to distinguish cancer class.

FIG. 3 displays an example of genomic signatures distinct to different cancer classes. Whole genome sequencing data for each respective cancer class is displayed. The x-axis represents the reference genome. The sequencing data have been clustered to reveal patterns of the presence of amplifications and deletions along the genome. After demonstrating that different cancer classes (e.g., cancers originating in different tissues) display distinct genomic patterns, it is reasonable to train a multinomial classifier to predict the probability that a subject has each respective cancer class.

FIG. 4 displays example predictions from a trained classifier for subjects with known cancer classes (e.g. 'Breast,' 'Lung,' and 'Colorectal'). Each panel displays the results for a respective cancer class. Each point represents the probability that an individual subject has each of the cancers listed. For each subject, the probabilities calculated for all cancer classes would sum to 1. In each panel, subjects with the known cancer class were analyzed by the trained classifier. The 'correct' cancer class is delineated in each panel with a star. In particular, for subjects with breast cancer, the trained classifier had a high accuracy for predicting the correct cancer class. Note, in all panels the probability for non-cancer appears to be elevated. This may be due to the fact that both healthy and diseased subjects a substantial portion of the subjects' cell-free DNA likely derives from healthy cells.

Figure 5:
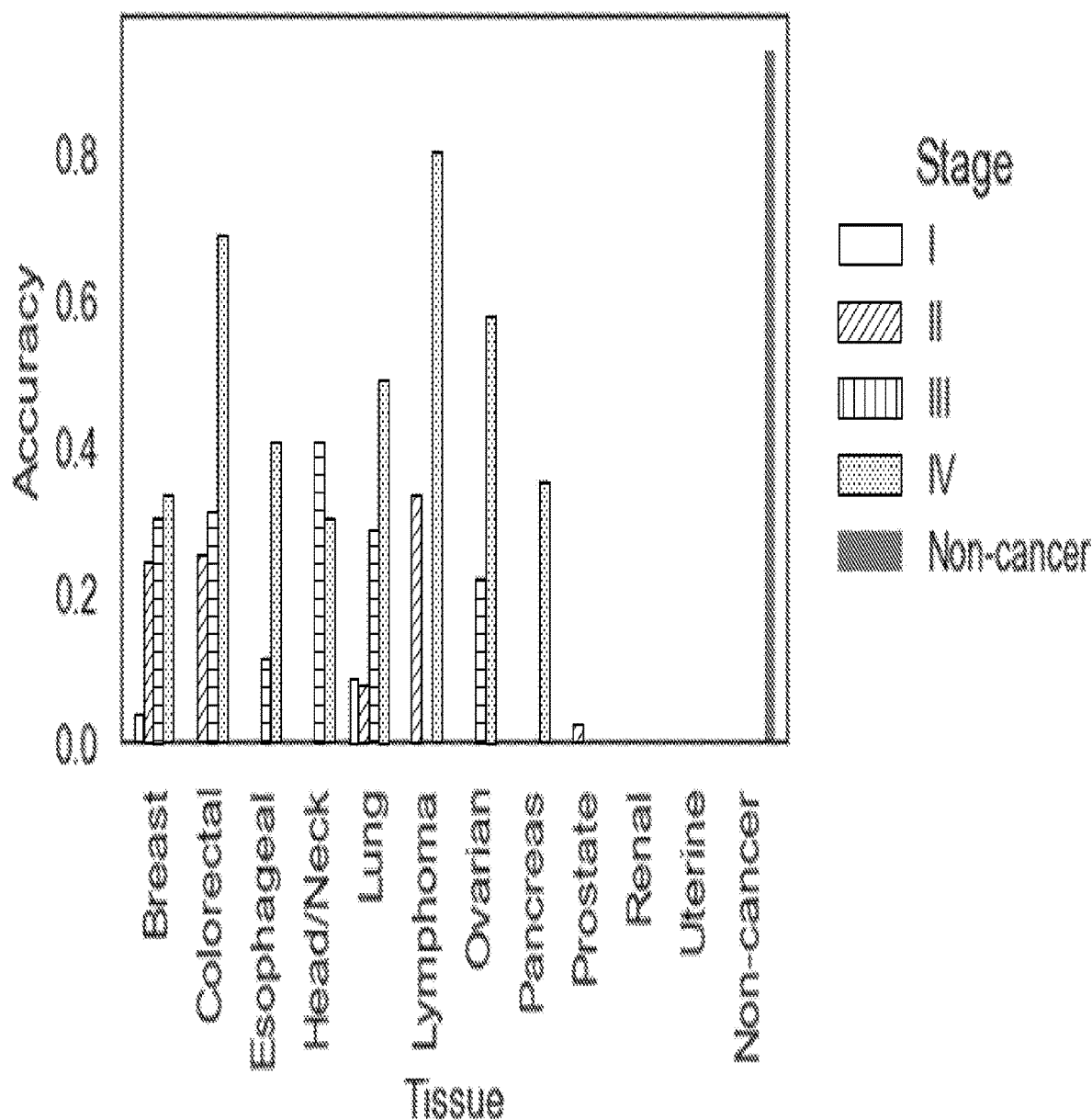
FIG. 5 illustrates bar graphs that show that the accuracy of predicting tissue type based on whole genome sequencing data increases with the stage of each cancer in accordance with some embodiments of the present disclosure.
Figure 7:
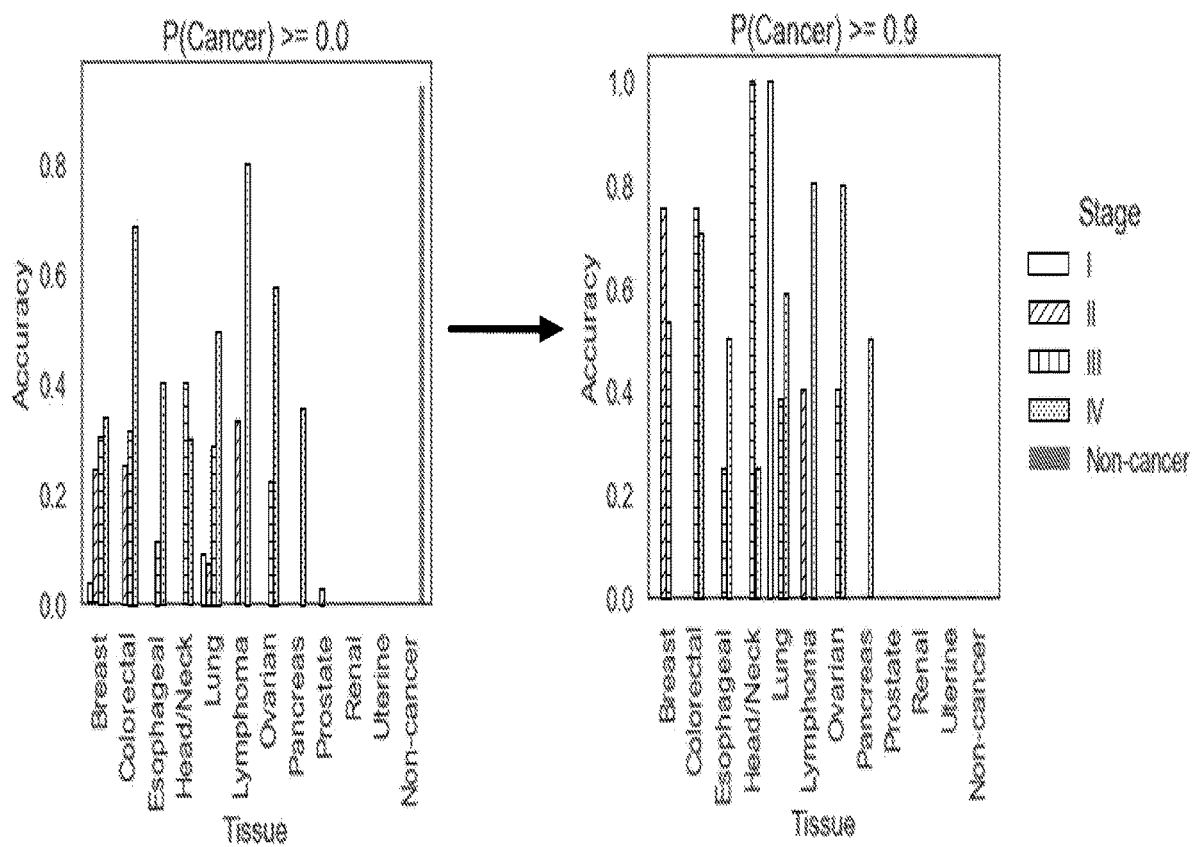
FIG. 7 illustrates bar graphs that show that the accuracy of predicting tissue type based on whole genome sequencing data increases both with the stage of each cancer and with the probability that each subject has some type of cancer in accordance with some embodiments of the present disclosure.
Figure 9A:
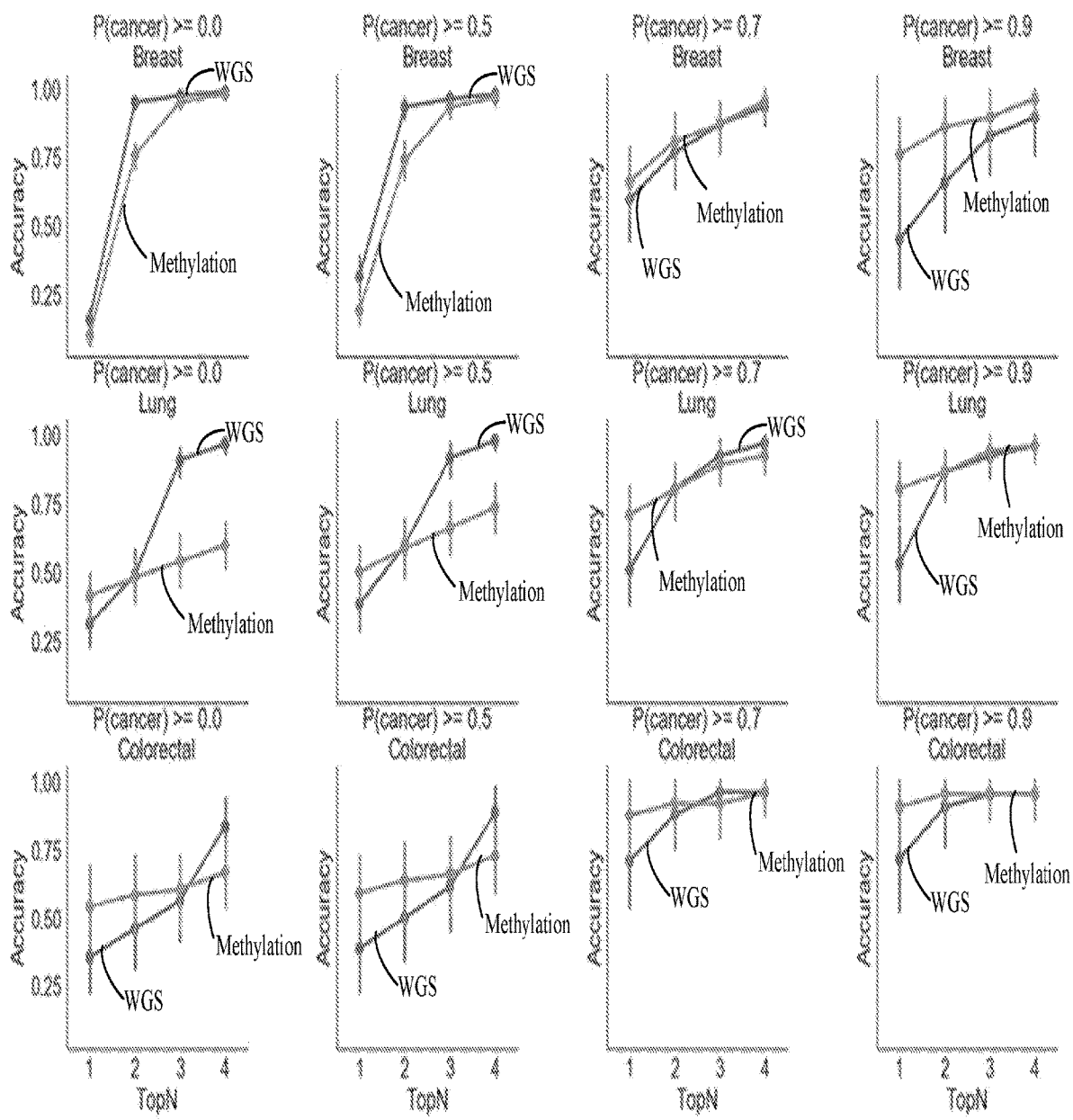
FIGS. 9A, 9B, and 9C collectively illustrate the probability that the accurate cancer class is among the top N predictions based either on methylation data or on whole genome sequencing data in accordance with some embodiments of the present disclosure.
Figure 9B:
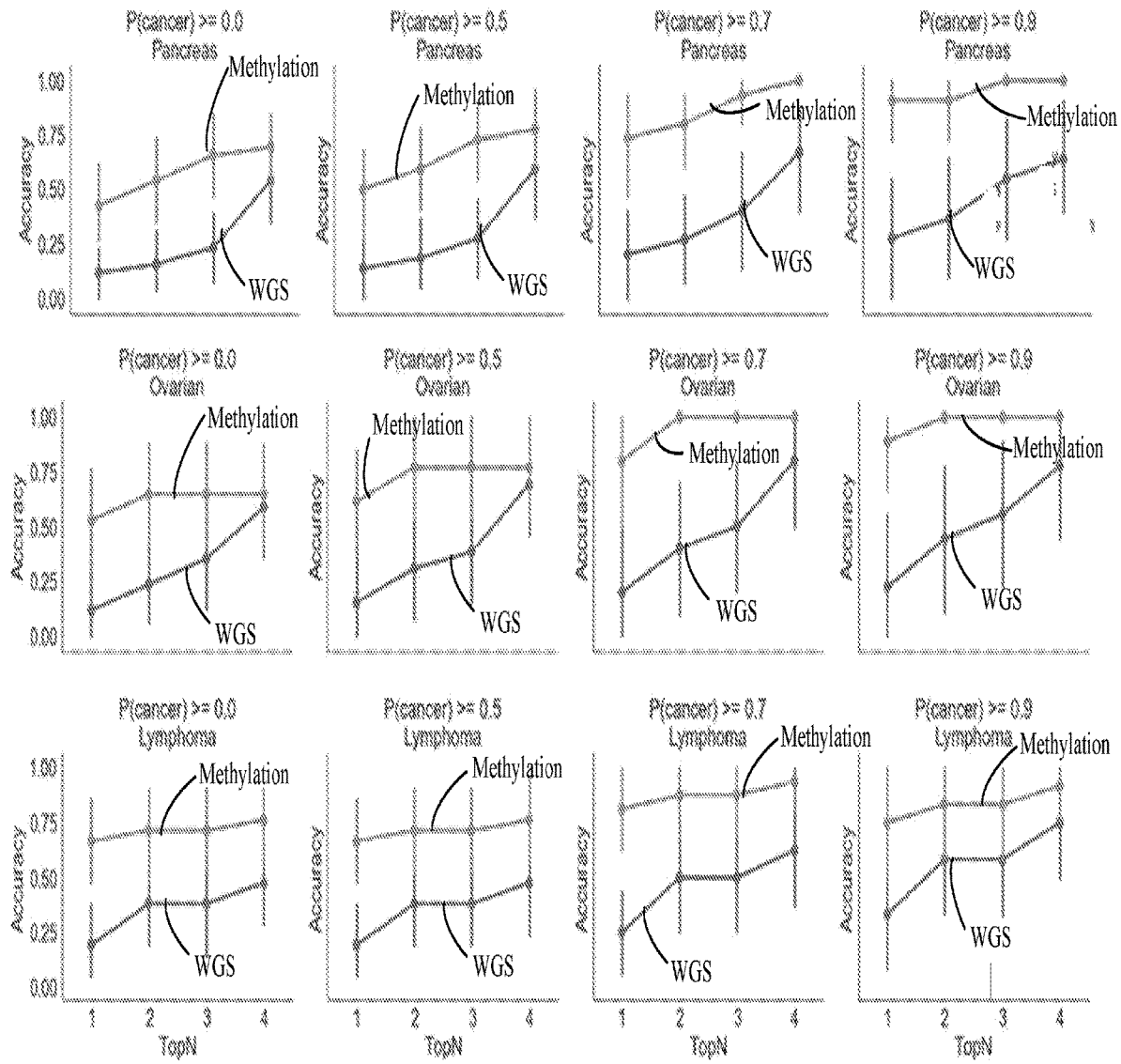
Figure 9C:
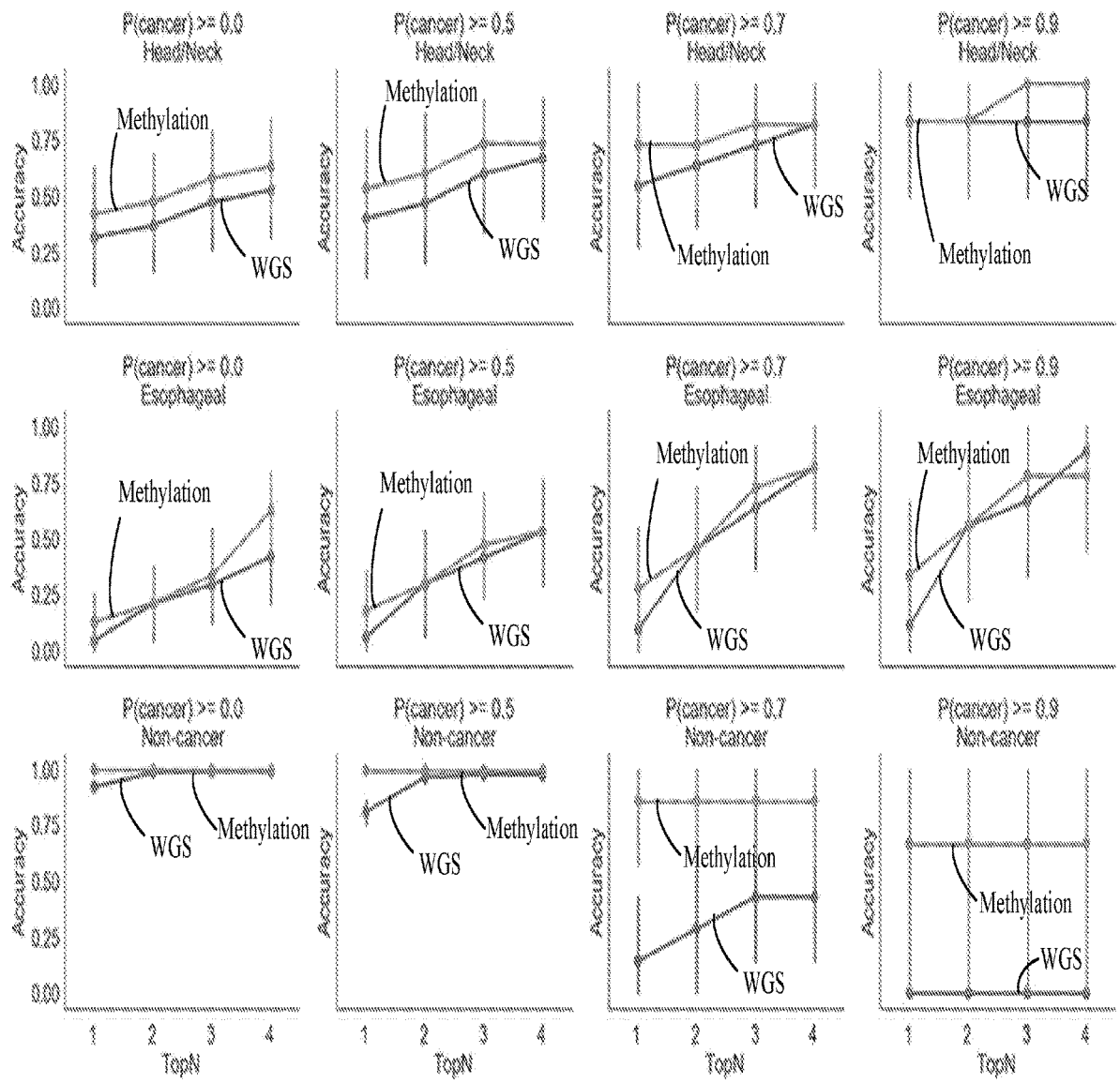

Example 2—Accuracy of classifiers improves with increasing cancer stage. The accuracy of the classification could potentially be improved by considering additional factors beyond whole genome sequencing. When a subject has been already classified as having a cancer type, one such factor that may further contribute to classification accuracy is cancer stage. When subjects are considered based on cancer stage, e.g. as displayed in FIG. 5, the accuracy of a trained classifier in predicting the 'correct' cancer type for each subject, generally increases as a function of the known stage of cancer for each subject. As shown in FIG. 6, this data depends on a limited number of subjects with known cancer type who have undergone whole genome sequencing. This suggests that increasing sample size could further improve the classification accuracy. The accuracy of the trained classifier predictions can also further be improved, as shown in FIG. 7, by limiting the subjects included in the example to those with a high probability of cancer (e.g. >=0.9). The accuracy based on removing the non-cancer population from the sample pool improves. However, a larger sample size may improve the results. The number of subjects included in each category is tabulated in FIG. 8. This adds another dimension (e.g., another factor) to the classification method.

Example 3—Combining whole genome sequencing classifiers with methylation classifiers. Based on the data shown in Example 2, classifiers trained on whole genome sequencing data alone can provide accurate prediction information for many different cancer classes. However, whole genome sequencing has great potential when used in combination with other information. For example, in FIGS. 9A, 9B, and 9C, a comparison of the accuracy of a classifier trained on methylation data and a classifier trained on whole genome sequencing is illustrated. Each column of the four column of each graph represents data from subjects with different probabilities of having cancer (e.g., the probability of having any class of cancer; e.g. "P (cancer)>=0.0, P (cancer)>=0.5, P (cancer)>=0.7, and P (cancer)>=0.9). For each cancer, the accuracy represents how well each trained classifier performed (e.g., how many subjects with cancer were correctly classified). Each classifier provides probabilities for each subject for a plurality of cancer classes (see Table 1 below). The top N indicates the top number (e.g., N) of cancer classes (e.g., the N cancer classes ordered by the probability of the subject having each cancer class), as predicted by the classifier. In some cases, a classifier trained on methylation data is more accurate (e.g., breast cancer, where the subjects have a probability of 0.9 or greater of having cancer). In some cases, a classifier trained on whole genome sequencing data is more accurate (e.g., lung cancer, where the subjects have a probability of 0.5 or greater of having cancer). This demonstrates that combining whole genome sequencing information with information from other sources, such as methylation data, has the possibility of adding value for determining the cancer class of subjects over above using just one single type of sequencing information alone.

TABLE 1

TopN predictions-each cancer class with a corresponding predicted probability

| Cancer Class | Class Probability |
|---|---|
| Non-cancer | 0.61 |
| Breast | 0.31 |
| Lung | 0.03 |
| Other | 0.01 |
| Colorectal | 0.01 |
| Head/Neck | 0.01 |
| Esophageal | 0.01 |
| Ovarian | 0.00 |
| Pancreas | 0.00 |
| Hepatobillary | 0.00 |
| Lymphoma | 0.00 |

Figure 10A:
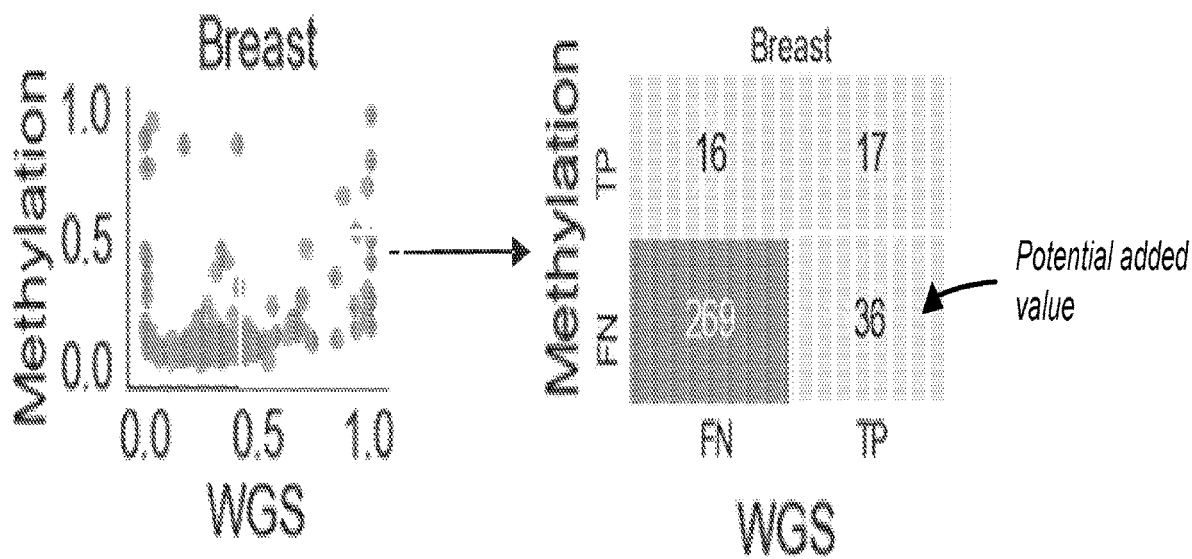
FIGS. 10A and 10B collectively illustrate the predictive capability of methylation data combined with whole genome sequencing data for different stages of breast cancer in accordance with some embodiments of the present disclosure.
Figure 10B:
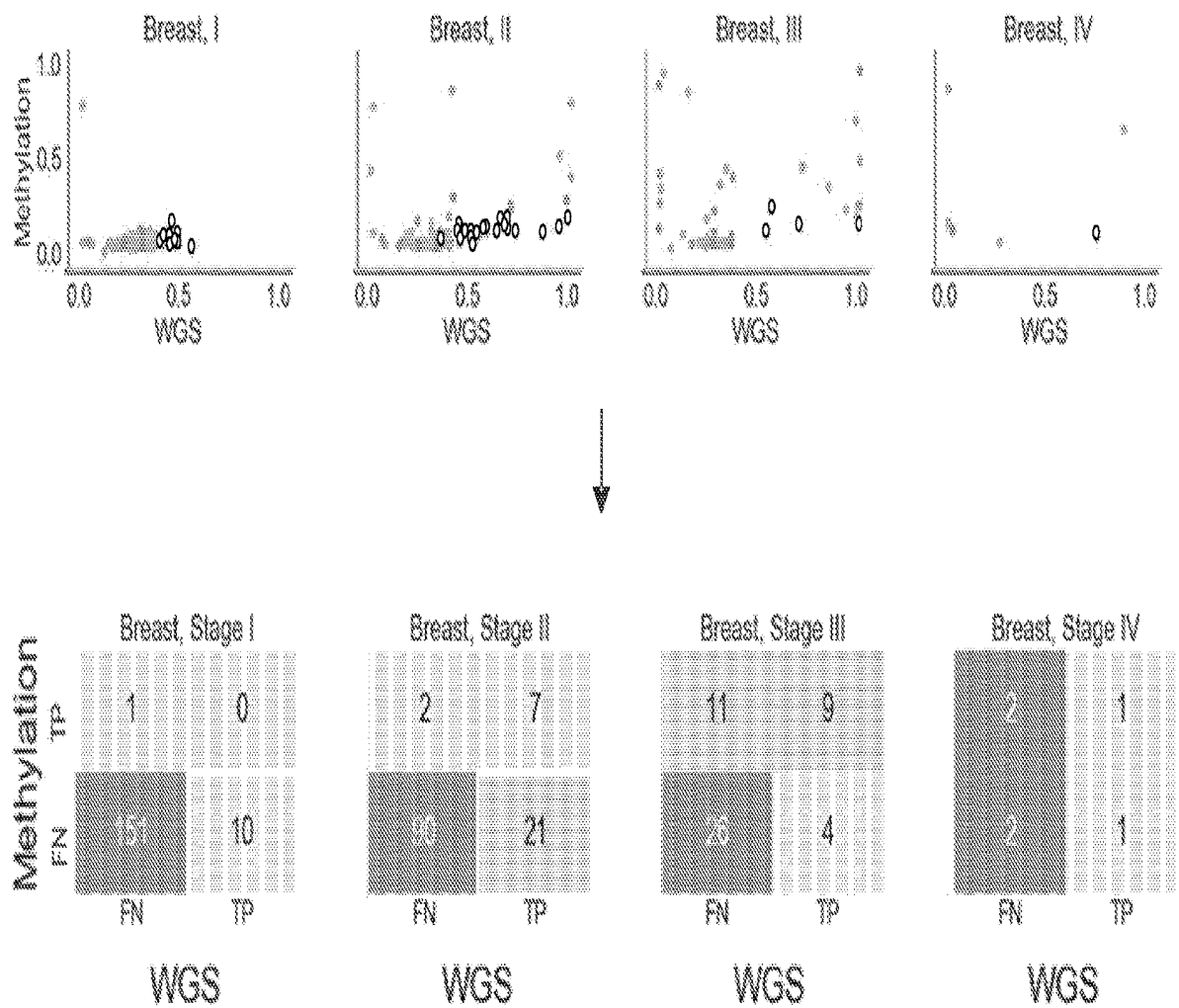

FIGS. 10A and 10B collectively illustrate the added value provided by using whole genome sequencing-trained classifiers alongside methylation-trained classifiers. Only subjects with breast cancer are analyzed here. On the x-axis, the accuracy of a whole genome sequencing-trained classifier is shown, while the y-axis represents the accuracy of a methylation-trained classifier. The grid corresponding to the graph in FIG. 10A breaks out the number of true positive and false negatives predicted by the classifier. Both types of classifiers produce a high number of false negative results (FN), demonstrating that even more work is needed to improve the true negative rate of these classifiers. However, given the importance of diagnosing cancer early to survival rates of subjects, every true positive prediction adds significant value to a diagnostics or screening pipeline. FIG. 10B further breaks down the breast cancer subjects by stage of breast cancer. The most added value for whole genome sequencing is in stage I and stage II for breast cancer; this is the same pattern as displayed by other data presented here (e.g., as with the breast cancer top N data shown in FIG. 10A) and appears to be specific to breast cancer.

Figure 11:
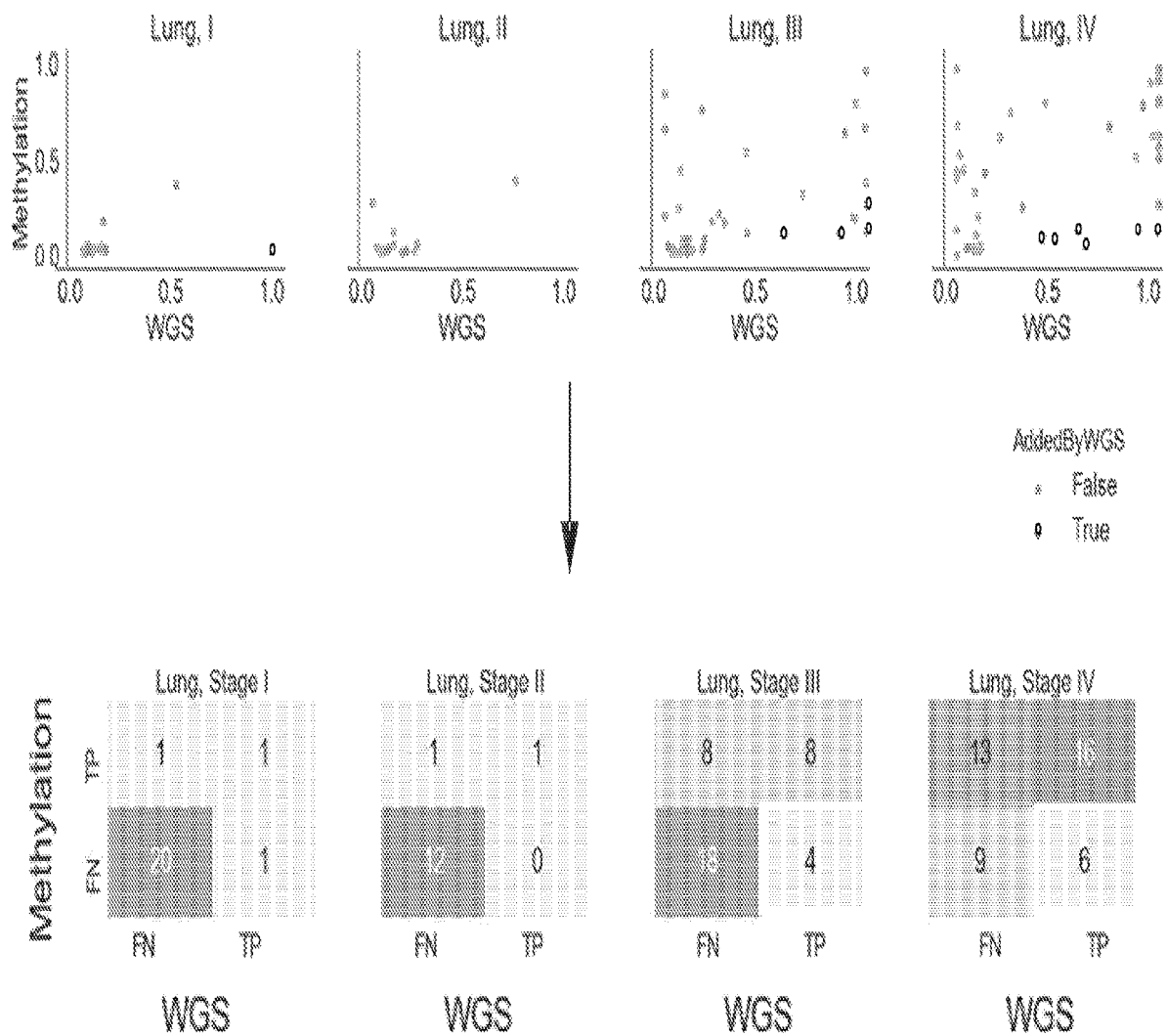
FIG. 11 illustrates the predictive capability of methylation data combined with whole genome sequencing data for different stages of lung cancer in accordance with some embodiments of the present disclosure.

FIG. 11 shows similar data as FIGS. 10A and 10B, but for lung cancer. However, here whole genome sequencing data adds the most value at stage III and stage IV for lung cancer.

Figure 12:
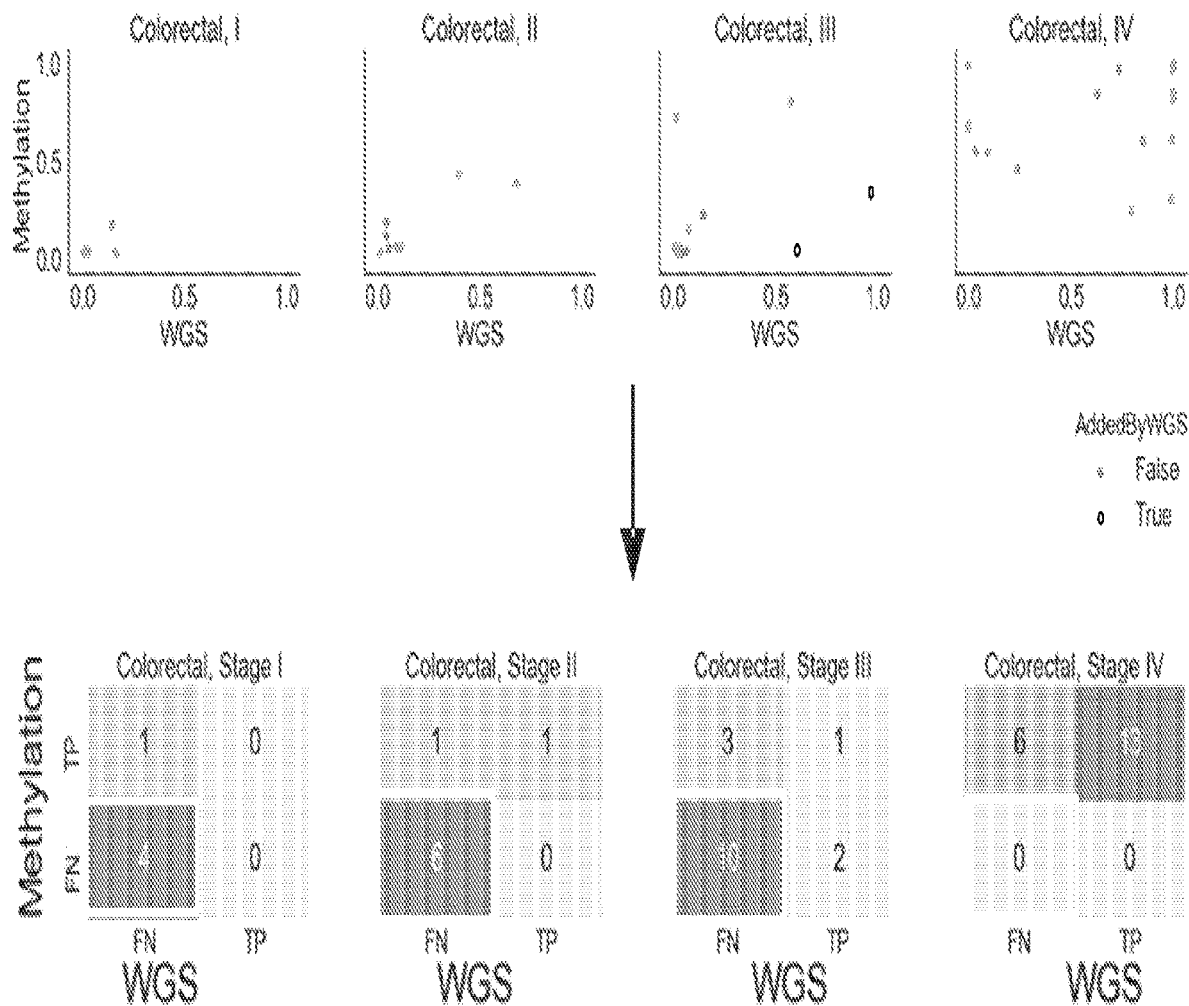
FIG. 12 illustrates the predictive capability of methylation data combined with whole genome sequencing data for different stages of colorectal cancer in accordance with some embodiments of the present disclosure.
Figure 13A:
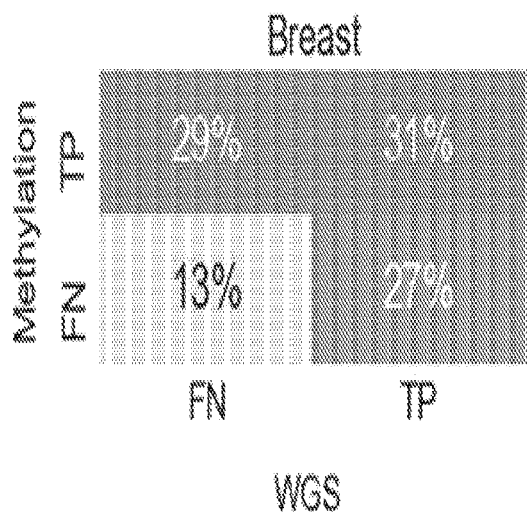
FIGS. 13A, 13B, and 13C collectively illustrate and example of the predictive capability of methylation data combined with whole genome sequencing data when there is a known probability that the subjects have cancer of the given type in accordance with some embodiments of the present disclosure.
Figure 13B:
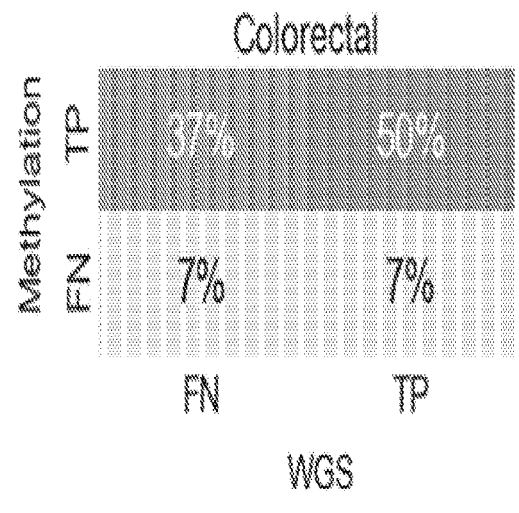
Figure 13C:
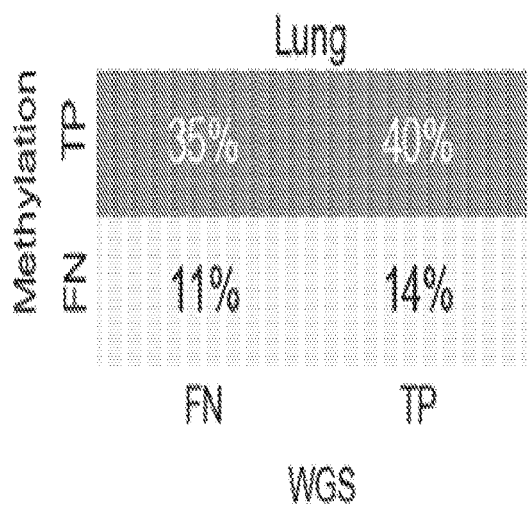

FIG. 12 shows similar data as FIGS. 10A, 10B, and 11, but for colorectal cancer. With colorectal cancer, the sample size needs to be increased to determine the full impact of either methylation- or whole genome sequencing-based classifiers. However, both types of classifiers have high sensitivity (e.g., true positives) for stage IV colorectal cancer subjects. FIGS. 13A, 13B, and 13C collectively summarize the information contained in the previous figures for breast, lung, and colorectal cancer, showing percentages instead of whole numbers. For all three examples here, using both types of sequencing data improves the sensitivity of the classification.

Figure 14:
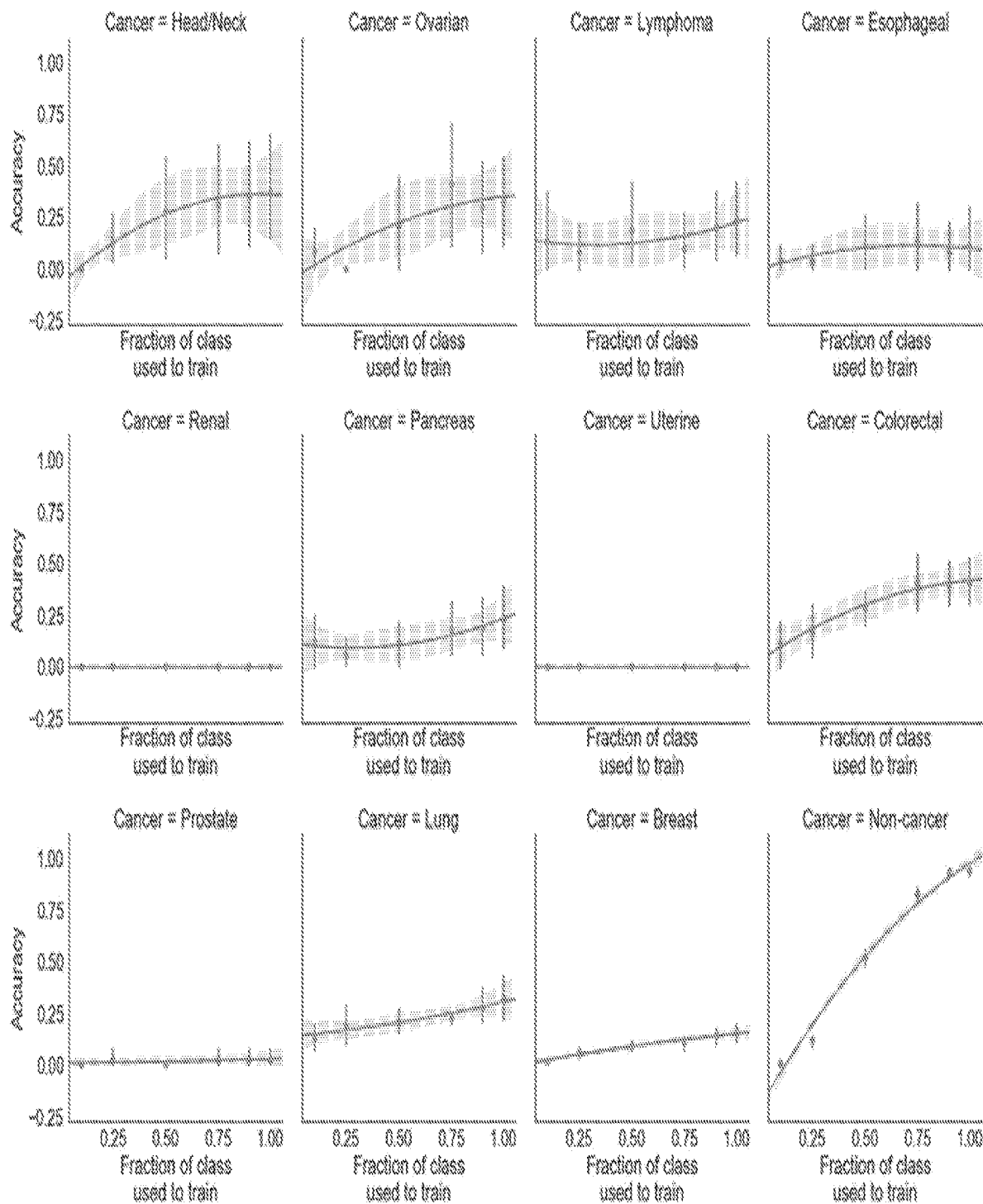
FIG. 14 illustrates the effect of sample size on classifier performance in accordance with some embodiments of the present disclosure.

A further consideration in training models of any kind, is the amount of training data that is required to provide a classifier with acceptable accuracy. FIG. 14 discloses the accuracy of a plurality of classifiers, based on the fraction of each class (e.g., the fraction of subjects in a particular category) that was used to train each classifier. For most cancer classes, the accuracy increases, as expected, with the fraction of the class that was used to train the classifier (e.g., head and neck cancer, ovarian cancer and colorectal cancer). However, some cancers may have more complex genomic patterns or are otherwise difficult to classify. For example, classifiers trained on renal cancer, uterine cancer, prostate cancer, and breast cancer subjects do not show improvement in accuracy with an increase in the fraction of each class used for training.

Figure 24:
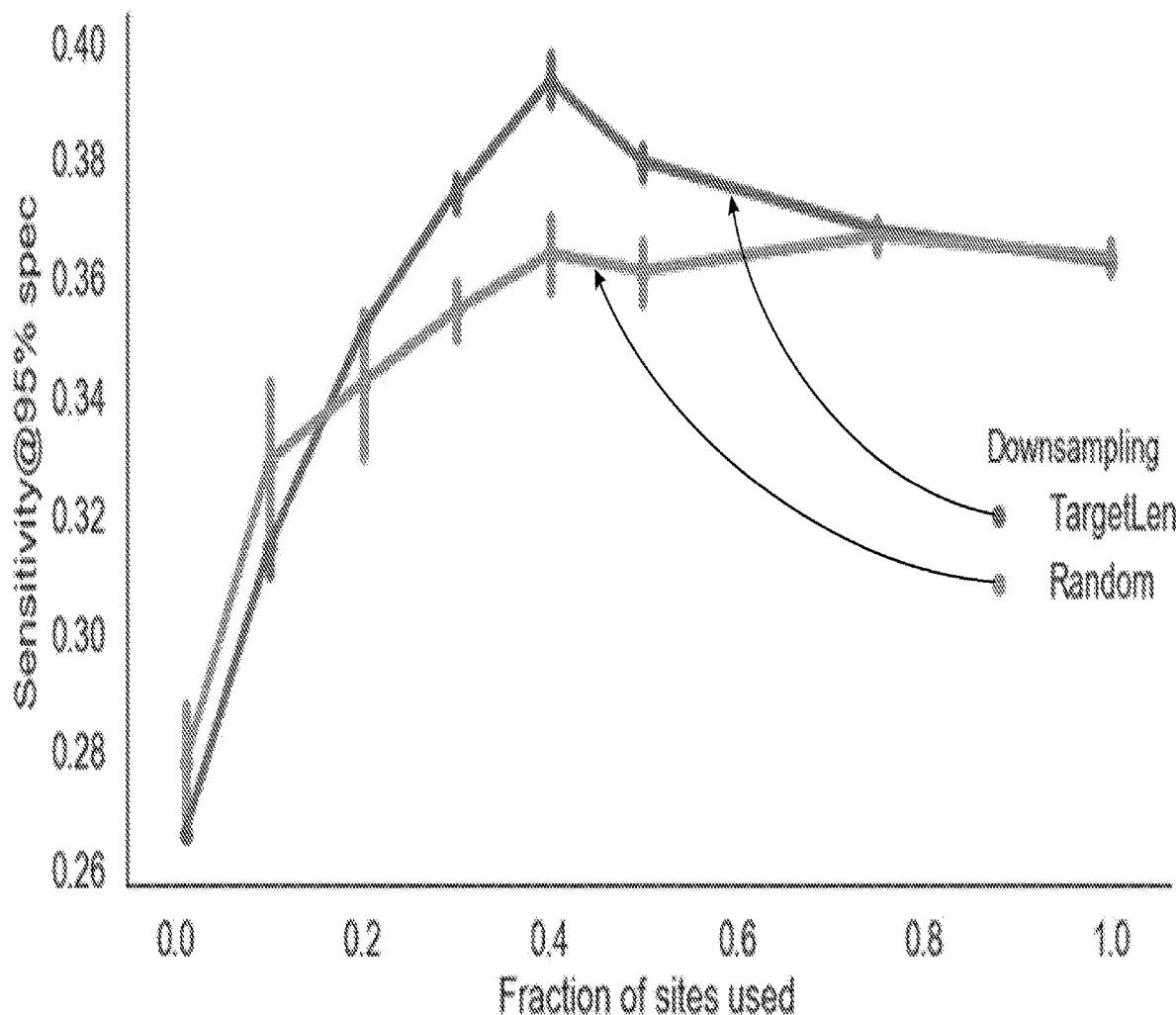
FIG. 24 illustrates comparison of sensitivity performance between targeted sequencing data and random whole genome sequencing data in accordance with some embodiments of the present disclosure.

Targeted sequencing data are also useful for classification. FIG. 24 illustrates classification accuracy based on sequencing data generated using a targeted panel including about 500 genes. In this example, probes targeting full length genes were used in the panel. For the curve labeled "random," gene targets were randomly added and their cumulative impact on classification performance (as measured by sensitivity values at 95 specificity) was evaluated. Data showed a general improvement of classification performance until about 80% of the target genes are included. For the curve labeled "TargetLen," gene targets were sequentially added based on their respective lengths, and their cumulative impact on classification performance (as measured by sensitivity values at 95 specificity) was evaluated. For example, the longest gene was included first in the analysis before the next longest gene, and etc. Data revealed continued improvement of classification performance until about the top 40% longest genes are included. Afterwards, subsequent inclusion of shorter genes seemed to provide no further advantages. Overall, the classification performance using targeted data is comparable with classification from WGS data.

Figure 15A:
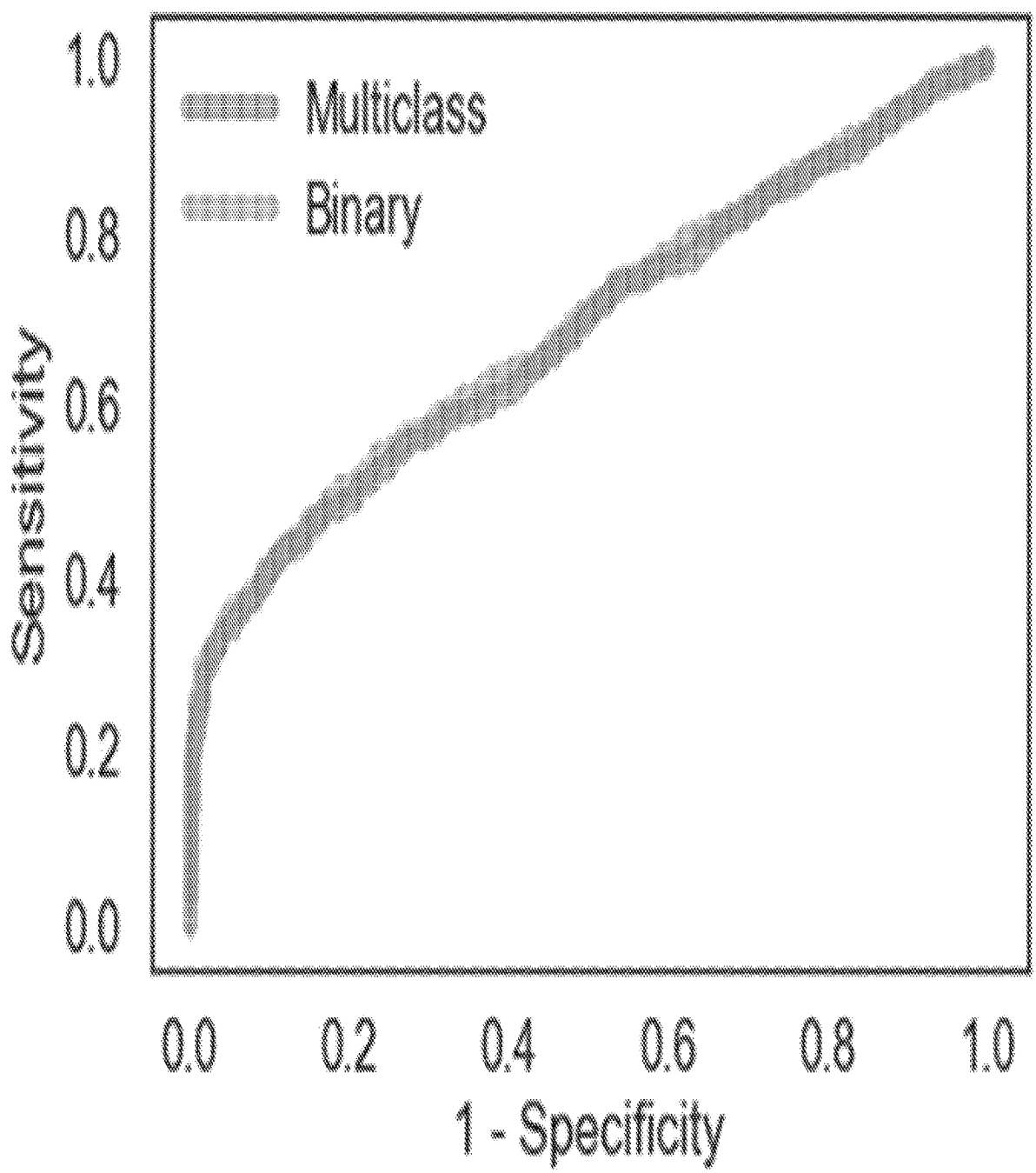
FIGS. 15A and 15B collectively illustrate that multiclass and binary training are comparable in binary classification performance in accordance with some embodiments of the present disclosure.
Figure 15B:
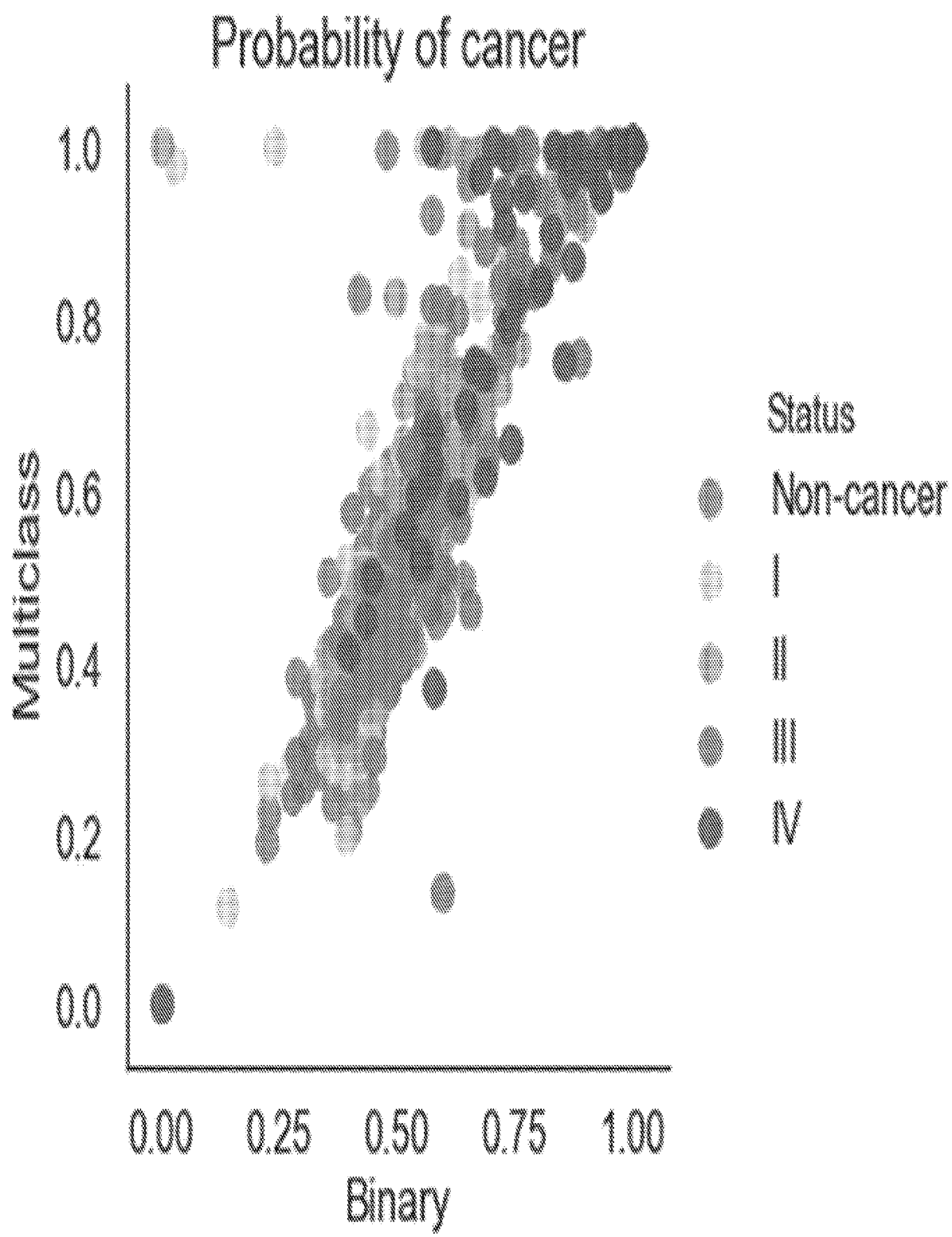
Figure 16A:
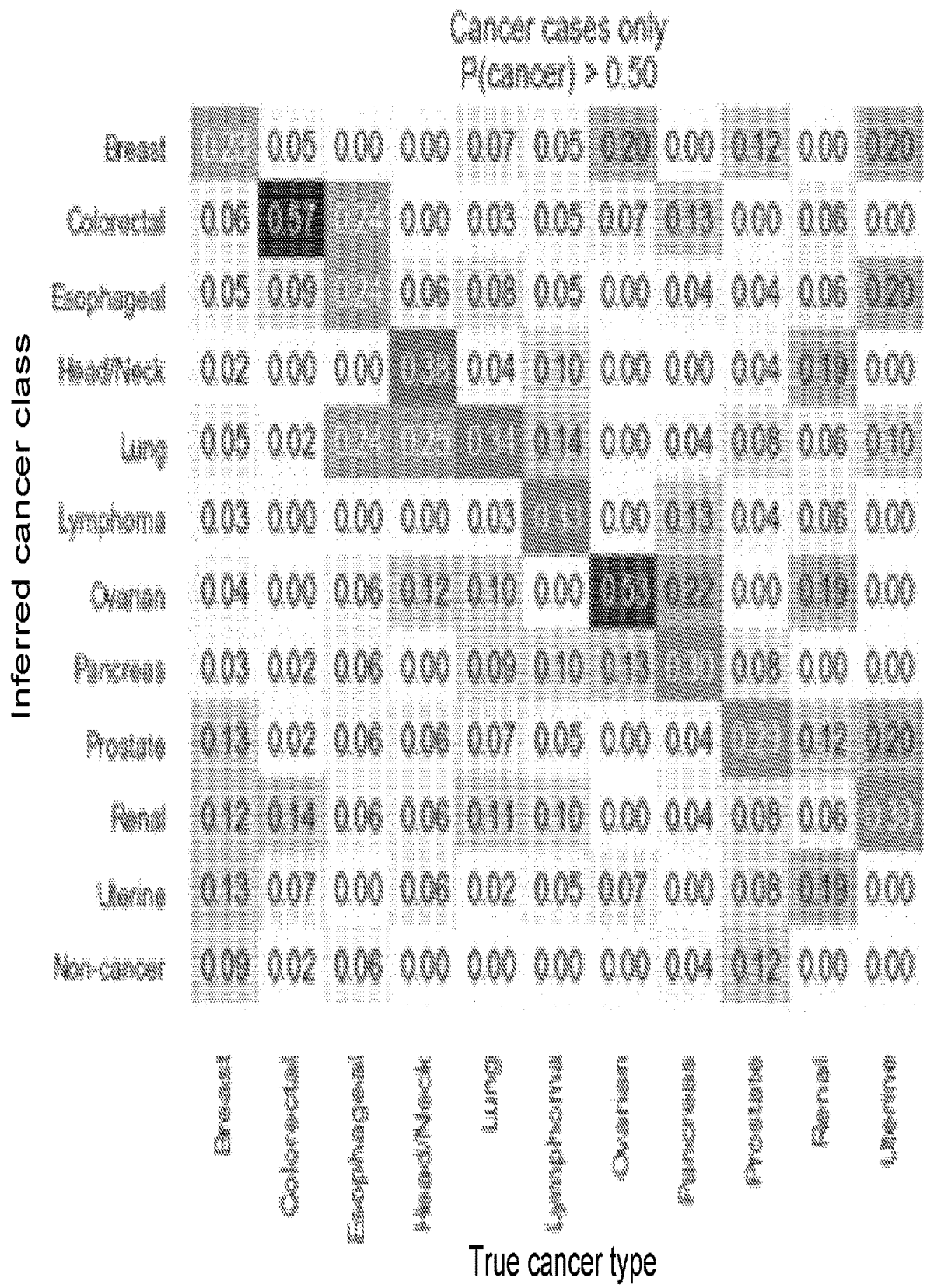
FIGS. 16A, 16B and 16C collectively illustrate the probability of the inferred cancer class compared with the known cancer type, given a known probability of each subject having cancer in accordance with some embodiments of the present disclosure.
Figure 16B:
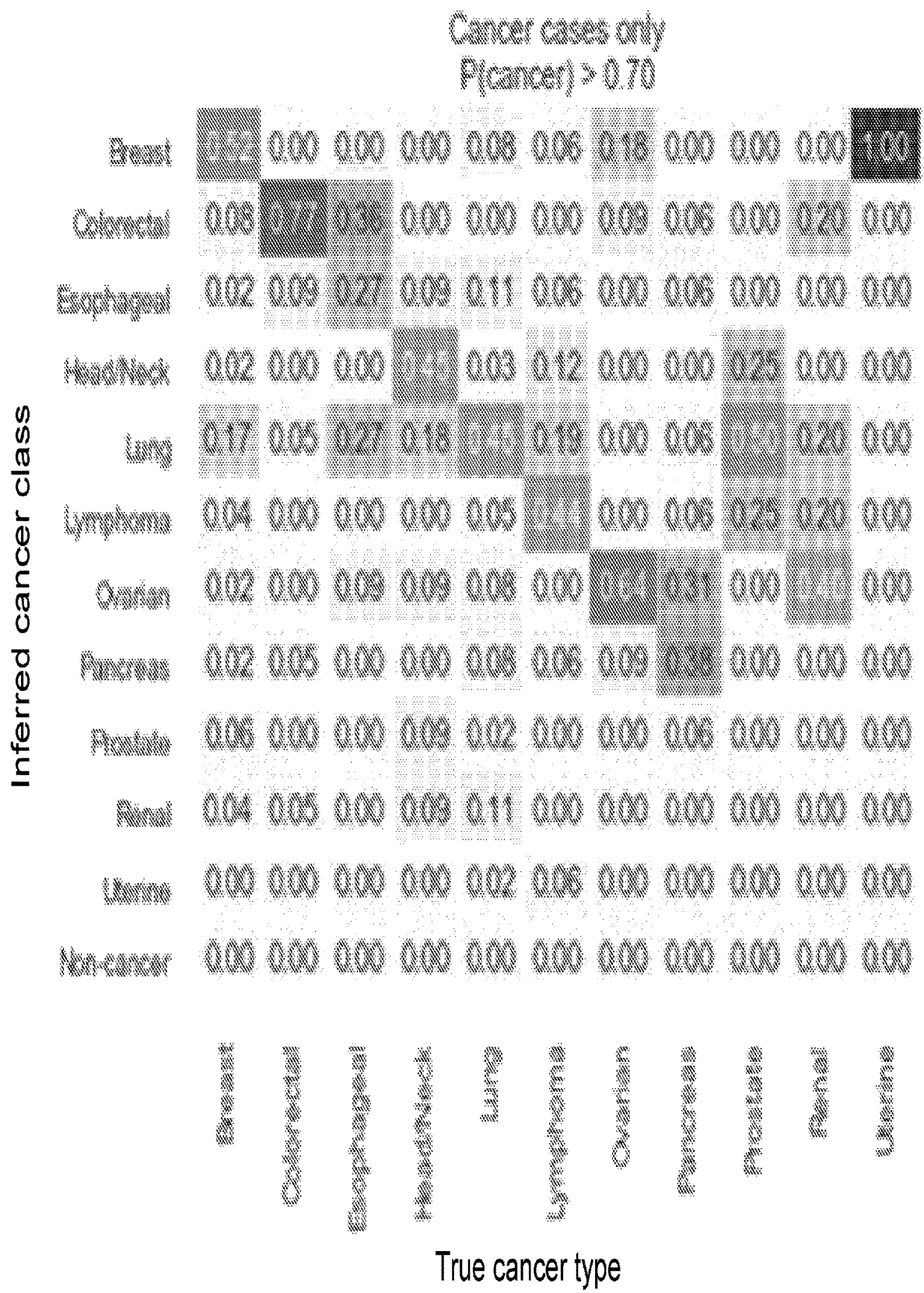
Figure 16C:
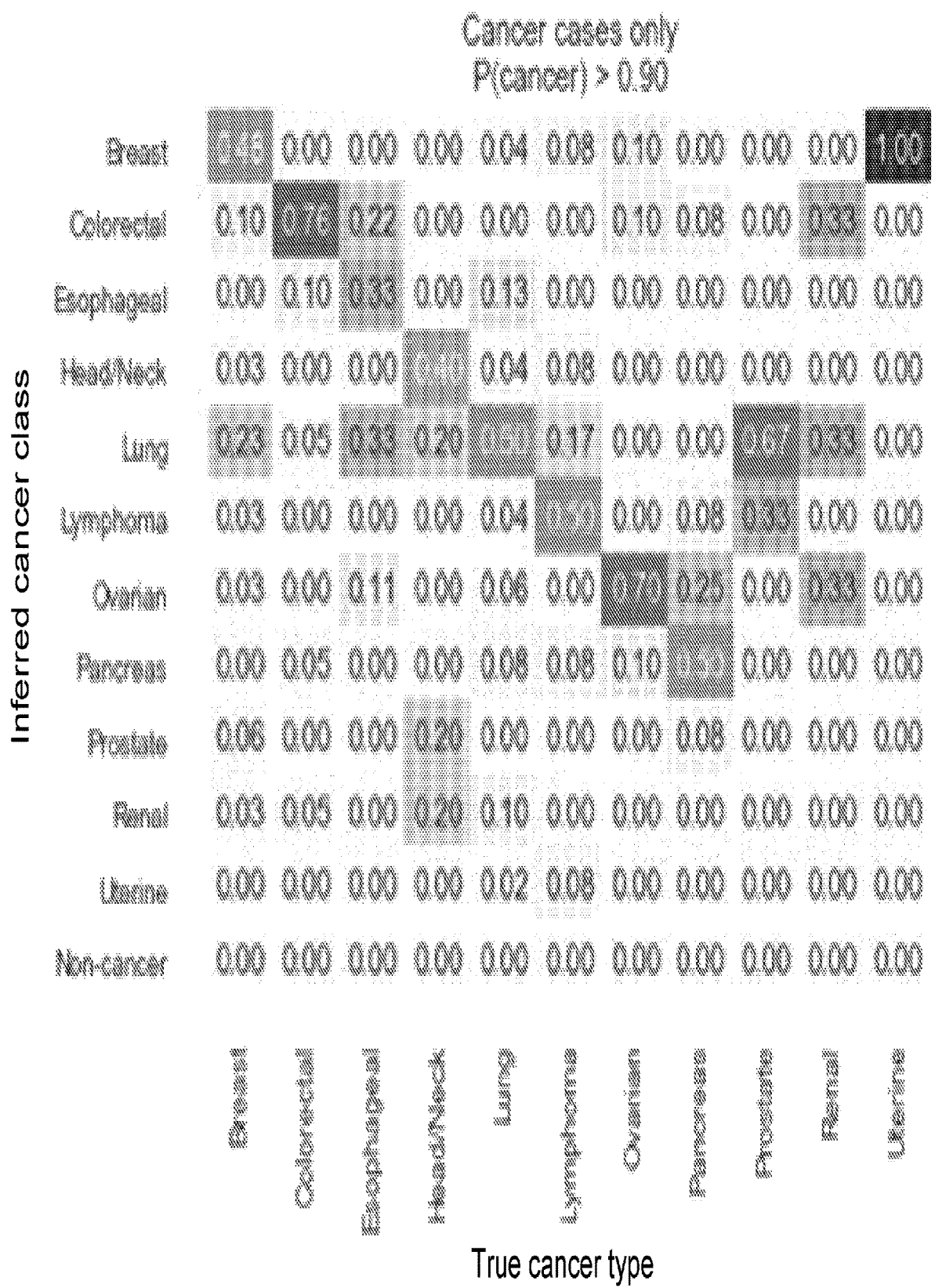

FIGS. 15A and 15B compare multiclass and binary classifiers. With the current training subjects, there is no distinct difference between these different classifier classes. FIGS. 16A, 16B, and 16C collectively summarize the probabilities predicted by the disclosed trained classifiers for each cancer class in the plurality of cancer classes and compares these predictions to the known cancer type in the plurality of cancer types.

In conclusion, even with a limited pool of training subjects for each cancer class, trained classifiers based on a combination of methylation data and whole genome sequencing data have improved accuracy in regards to classifying subjects to cancer class.

Figure 17:
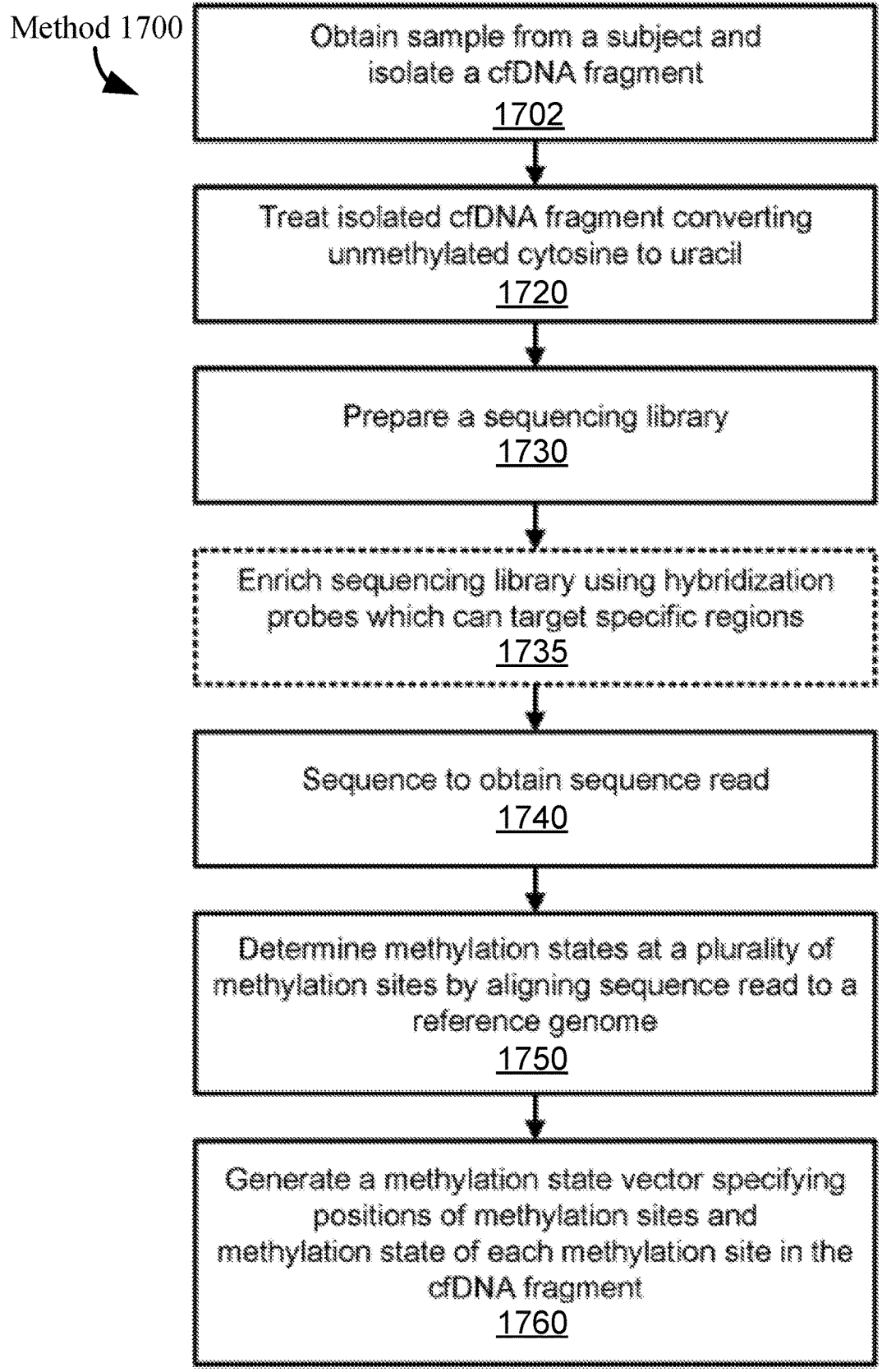
FIG. 17 illustrates an example flowchart of a method for obtaining a methylation information for the purposes of screening for a cancer condition in a test subject in accordance with some embodiments of the present disclosure.

Example 4—Generation of Methylation State Vector. FIG. 17 is a flowchart describing a process 1700 of sequencing a fragment of cfDNA to obtain a methylation state vector, according to an embodiment in accordance with the present disclosure.

Referring to step 1702, the cfDNA fragments are obtained from the biological sample (e.g., as discussed above in conjunction with FIG. 2). Referring to step 1720, the cfDNA fragments are treated to convert unmethylated cytosines to uracils. In one embodiment, the DNA is subjected to a bisulfite treatment that converts the unmethylated cytosines of the fragment of cfDNA to uracils without converting the methylated cytosines. For example, a commercial kit such as the EZ DNA Methylation™—Gold, EZ DNA Methylation™—Direct or an EZ DNA Methylation™—Lightning kit (available from Zymo Research Corp (Irvine, CA)) is used for the bisulfite conversion in some embodiments. In other embodiments, the conversion of unmethylated cytosines to uracils is accomplished using an enzymatic reaction. For example, the conversion can use a commercially available kit for conversion of unmethylated cytosines to uracils, such as APOBEC-Seq (NEBiolabs, Ipswich, MA).

From the converted cfDNA fragments, a sequencing library is prepared (step 1730). Optionally, the sequencing library is enriched 1735 for cfDNA fragments, or genomic regions, that are informative for cancer status using a plurality of hybridization probes. The hybridization probes are short oligonucleotides capable of hybridizing to particularly specified cfDNA fragments, or targeted regions, and enriching for those fragments or regions for subsequent sequencing and analysis. Hybridization probes may be used to perform a targeted, high-depth analysis of a set of specified CpG sites of interest to the researcher. Once prepared, the sequencing library or a portion thereof can be sequenced to obtain a plurality of sequence reads (1740). The sequence reads may be in a computer-readable, digital format for processing and interpretation by computer software From the sequence reads, a location and methylation state for each of CpG site is determined based on an alignment of the sequence reads to a reference genome (1750). A methylation state vector for each fragment specifying a location of the fragment in the reference genome (e.g., as specified by the position of the first CpG site in each fragment, or another similar metric), a number of CpG sites in the fragment, and the methylation state of each CpG site in the fragment (1760).

Figure 18:
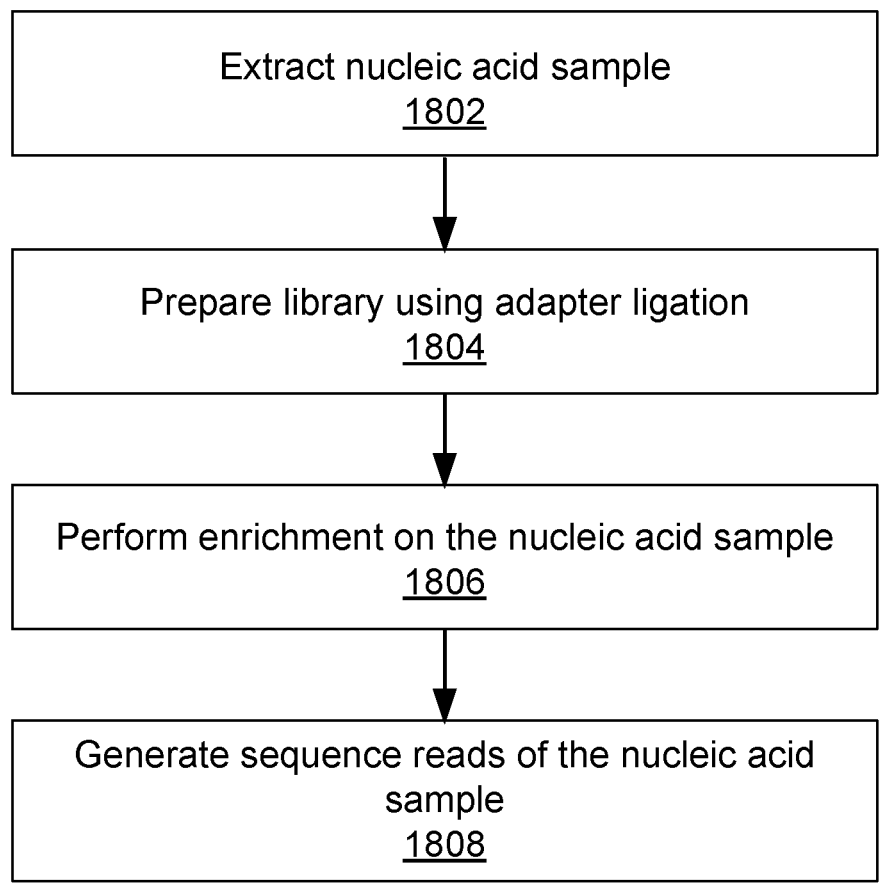
FIG. 18 illustrates a flowchart of a method for preparing a nucleic acid sample for sequencing in accordance with some embodiments of the present disclosure.

Example 5—Obtaining a Plurality of Sequence Reads. FIG. 18 is a flowchart of method 1800 for preparing a nucleic acid sample for sequencing according to one embodiment. The method 1800 includes, but is not limited to, the following steps. For example, any step of method 1800 may comprise a quantitation sub-step for quality control or other laboratory assay procedures known to one skilled in the art.

In block 1802, a nucleic acid sample (DNA or RNA) is extracted from a subject. The sample may be any subset of the human genome, including the whole genome. The sample may be extracted from a subject known to have or suspected of having cancer. The sample may include blood, plasma, serum, urine, fecal, saliva, other types of bodily fluids, or any combination thereof. In some embodiments, methods for drawing a blood sample (e.g., syringe or finger prick) may be less invasive than procedures for obtaining a tissue biopsy, which may require surgery. The extracted sample may comprise cfDNA and/or ctDNA. For healthy individuals, the human body may naturally clear out cfDNA and other cellular debris. If a subject has a cancer or disease, ctDNA in an extracted sample may be present at a detectable level for diagnosis.

In block 1804, a sequencing library is prepared. During library preparation, unique molecular identifiers (UMI) are added to the nucleic acid molecules (e.g., DNA molecules) through adapter ligation. The UMIs are short nucleic acid sequences (e.g., 4-10 base pairs) that are added to ends of DNA fragments during adapter ligation. In some embodiments, UMIs are degenerate base pairs that serve as a unique tag that can be used to identify sequence reads originating from a specific DNA fragment. During PCR amplification following adapter ligation, the UMIs are replicated along with the attached DNA fragment. This provides a way to identify sequence reads that came from the same original fragment in downstream analysis.

In block 1806, targeted DNA sequences are enriched from the library. During enrichment, hybridization probes (also referred to herein as "probes") are used to target, and pull down, nucleic acid fragments informative for the presence or absence of cancer (or disease), cancer status, or a cancer classification (e.g., cancer class or tissue of origin). For a given workflow, the probes may be designed to anneal (or hybridize) to a target (complementary) strand of DNA. The target strand may be the "positive" strand (e.g., the strand transcribed into mRNA, and subsequently translated into a protein) or the complementary "negative" strand. The probes may range in length from 10s, 100s, or 1000s of base pairs. In one embodiment, the probes are designed based on a gene panel to analyze particular mutations or target regions of the genome (e.g., of the human or another organism) that are suspected to correspond to certain cancers or other types of diseases. Moreover, the probes may cover overlapping portions of a target region. In block 1808, these probes are used to general sequence reads of the nucleic acid sample.

Figure 19:
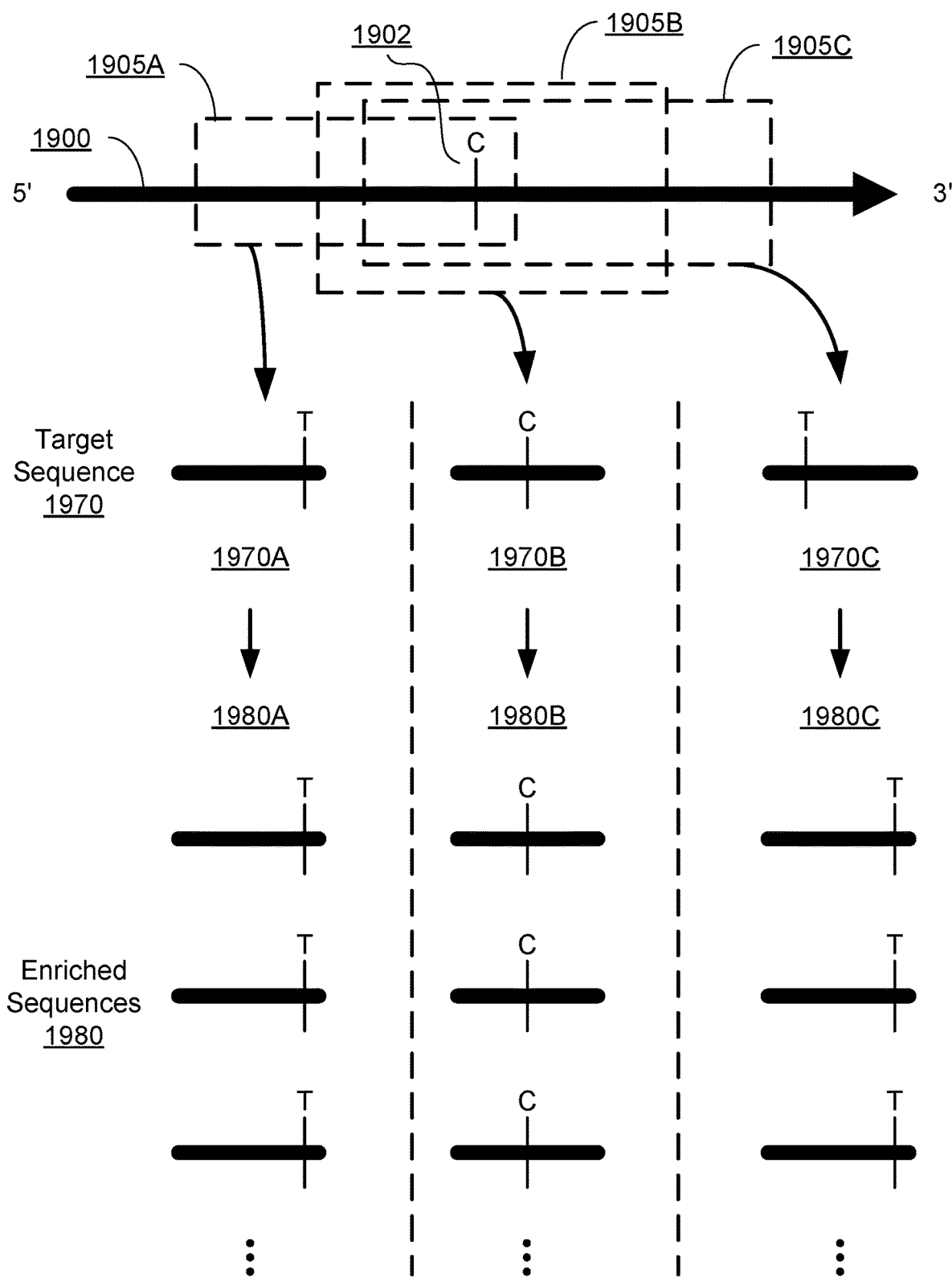
FIG. 19 is a graphical representation of the process for obtaining sequence reads in accordance with some embodiments of the present disclosure.

FIG. 19 is a graphical representation of the process for obtaining sequence reads according to one embodiment. FIG. 19 depicts one example of a nucleic acid segment 1900 from the sample. Here, the nucleic acid segment 1900 can be a single-stranded nucleic acid segment, such as a single stranded. In some embodiments, the nucleic acid segment 1900 is a double-stranded cfDNA segment. The illustrated example depicts three regions 1905A, 1905B, and 1905C of the nucleic acid segment that can be targeted by different probes. Specifically, each of the three regions 1905A, 1905B, and 1905C includes an overlapping position on the nucleic acid segment 1900. An example overlapping position is depicted in FIG. 19 as the cytosine ("C") nucleotide base 1902. The cytosine nucleotide base 1902 is located near a first edge of region 1905A, at the center of region 1905B, and near a second edge of region 1905C.

In some embodiments, one or more (or all) of the probes are designed based on a gene panel to analyze particular mutations or target regions of the genome (e.g., of the human or another organism) that are suspected to correspond to certain cancers or other types of diseases. By using a targeted gene panel rather than sequencing all expressed genes of a genome, also known as "whole exome sequencing," the method 1900 may be used to increase sequencing depth of the target regions, where depth refers to the count of the number of times a given target sequence within the sample has been sequenced. Increasing sequencing depth reduces required input amounts of the nucleic acid sample.

Hybridization of the nucleic acid sample 1900 using one or more probes results in an understanding of a target sequence 1970. As shown in FIG. 19, the target sequence 1970 is the nucleotide base sequence of the region 1905 that is targeted by a hybridization probe. The target sequence 1970 can also be referred to as a hybridized nucleic acid fragment. For example, target sequence 1970A corresponds to region 1905A targeted by a first hybridization probe, target sequence 1970B corresponds to region 1905B targeted by a second hybridization probe, and target sequence 1970C corresponds to region 1905C targeted by a third hybridization probe. Given that the cytosine nucleotide base 1902 is located at different locations within each region 1905A-C targeted by a hybridization probe, each target sequence 1970 includes a nucleotide base that corresponds to the cytosine nucleotide base 1902 at a particular location on the target sequence 1970.

After a hybridization step, the hybridized nucleic acid fragments are captured and may also be amplified using PCR. For example, the target sequences 1970 can be enriched to obtain enriched sequences 1980 that can be subsequently sequenced. In some embodiments, each enriched sequence 1980 is replicated from a target sequence 1970. Enriched sequences 1980A and 1980C that are amplified from target sequences 1970A and 1970C, respectively, also include the thymine nucleotide base located near the edge of each sequence read 1980A or 1980C. As used hereafter, the mutated nucleotide base (e.g., thymine nucleotide base) in the enriched sequence 1980 that is mutated in relation to the reference allele (e.g., cytosine nucleotide base 1902) is considered as the alternative allele. Additionally, each enriched sequence 1980B amplified from target sequence 1970B includes the cytosine nucleotide base located near or at the center of each enriched sequence 1980B.

In block 1808, sequence reads are generated from the enriched DNA sequences, e.g., enriched sequences 1980 shown in FIG. 19. Sequencing data may be acquired from the enriched DNA sequences by known means in the art. For example, the method 1900 may include next generation sequencing (NGS) techniques including synthesis technology (Illumina), pyrosequencing (454 Life Sciences), ion semiconductor technology (Ion Torrent sequencing), single-molecule real-time sequencing (Pacific Biosciences), sequencing by ligation (SOLID sequencing), nanopore sequencing (Oxford Nanopore Technologies), or paired-end sequencing. In some embodiments, massively parallel sequencing is performed using sequencing-by-synthesis with reversible dye terminators.

In some embodiments, the sequence reads may be aligned to a reference genome using known methods in the art to determine alignment position information. The alignment position information may indicate a beginning position and an end position of a region in the reference genome that corresponds to a beginning nucleotide base and end nucleotide base of a given sequence read. Alignment position information may also include sequence read length, which can be determined from the beginning position and end position. A region in the reference genome may be associated with a gene or a segment of a gene.

In various embodiments, a sequence read is comprised of a read pair denoted as $R_1$ and $R_2$. For example, the first read $R_1$ may be sequenced from a first end of a nucleic acid fragment whereas the second read $R_2$ may be sequenced from the second end of the nucleic acid fragment. Therefore, nucleotide base pairs of the first read $R_1$ and second read $R_2$ may be aligned consistently (e.g., in opposite orientations) with nucleotide bases of the reference genome. Alignment position information derived from the read pair $R_1$ and $R_2$ may include a beginning position in the reference genome that corresponds to an end of a first read (e.g., $R_1$) and an end position in the reference genome that corresponds to an end of a second read (e.g., $R_2$). In other words, the beginning position and end position in the reference genome represent the likely location within the reference genome to which the nucleic acid fragment corresponds. An output file having SAM (sequence alignment map) format or BAM (binary) format may be generated and output for further analysis such as variant calling described above in conjunction with FIG. 2.

Example 6—Cell-Free Genome Atlas Study (CCGA) Cohort. Subjects from the CCGA [NCT02889978] were used as reference subjects for a convolutional neural network classifier described in U.S. Provisional Application No. 62/679,746. CCGA is a prospective, multi-center, observational cfDNA-based early cancer detection study that has enrolled about 15,000 demographically-balanced participants at over 140 sites. Blood was collected from subjects with newly diagnosed therapy-naive cancer (C, case) and participants without a diagnosis of cancer (noncancer [NC], control) as defined at enrollment. This preplanned substudy included 878 cases, 580 controls, and 169 assay controls (n=1627) across twenty tumor types and all clinical stages.

All samples were analyzed by: 1) paired cfDNA and white blood cell (WBC)-targeted sequencing (60,000X, 507 gene panel); a joint caller removed WBC-derived somatic variants and residual technical noise; 2) paired cfDNA and WBC whole-genome sequencing (WGS; 35X); a novel machine learning algorithm generated cancer-related signal scores; joint analysis identified shared events; and 3) cfDNA whole-genome bisulfite sequencing (WGBS; 34X); normalized scores were generated using abnormally methylated fragments. In the targeted assay, non-tumor WBC-matched cfDNA somatic variants (SNVs/indels) accounted for 76% of all variants in non-cancer (NC) patients and 65% in cancer (C) patients. Consistent with somatic mosaicism (e.g., clonal hematopoiesis), WBC-matched variants increased with age; several were non-canonical loss-of-function mutations not previously reported. After WBC variant removal, canonical driver somatic variants were highly specific to C (e.g., in EGFR and PIK3CA, 0 NC had variants vs 11 and 30, respectively, of C). Similarly, of 8 NC with somatic copy number alterations (SCNAs) detected with WGS, four were derived from WBCs. WGBS data of the CCGA reveals informative hyper- and hypo-fragment level CpGs (1:2 ratio); a subset of which was used to calculate methylation scores. A consistent "cancer-like" signal was observed in <1% of NC participants across all assays (representing potential undiagnosed cancers). An increasing trend was observed in NC vs stages I-III vs stage IV (nonsynonymous SNVs/indels per Mb [Mean±SD] NC: 1.01±0.86, stages I-III: 2.43±3.98; stage IV: 6.45±6.79; WGS score NC: 0.00±0.08, I-III: 0.27±0.98; IV: 1.95±2.33; methylation score NC: 0±0.50; I-III: 1.02±1.77; IV: 3.94±1.70). These data demonstrate the feasibility of achieving>99% specificity for invasive cancer, and support the promise of cfDNA assay for early cancer detection.

Example 7: Comparison of Copy Number Aberrations for WGBS and WGS

Samples collected largely as described in Example 6, were analyzed to determine whether somatic copy number aberrations (SCNA) were detected at comparable rates in both WGBS and WGS data. Blood was collected from patients, and the WGBS analysis was performed on plasma from the same visit but from separate blood vials than those used for the WGS analysis. Table 2 summarizes some metrics used to compare SCNA detection from WGBS and WGS data. The entire set of WGBS patients comprised 1187 samples, of which 1179 samples had sufficient coverage to be evaluated. The entire set of WGS patients comprised 1897, of which 1742 sufficient coverage to be evaluated. The calculations were performed for 1167 patients who had sufficient coverage of both WGBS and WGS data (e.g., the joint evaluable set). The WGBS and WGS data sets exhibited an average 38X±8.1 and 37X±5.8 coverage, respectively. The bin size used for analysis was 100 kb for both data sets; however, WGBS analysis contained 1.25% fewer 100 kb bins (24,812) compared with WGS (25,128). The mean average pairwise differences (MAPD) for each data set are also similar, 0.0075±0.0014 and 0.0082±0.018 respectively.

TABLE 2

Performance metrics (median ± SD)

| | WGBS | WGS |
|---|---|---|
| Evaluable (Y/N) | 1179/8 | 1742/155 |
| Joint evaluable | 1167 | |
| Mean Coverage (X) | 38.0 ± 8.1 | 37.0 ± 5.8 |
| final MAPD | 0.0075 ± 0.0014 | 0.0082 ± 0.018 |
| Z-score | 3.84 ± 46 | 3.28 ± 33 |
| B-score | 0.59 ± 0.16 | 0.58 ± 0.16 |
| Mean Length (bp) | 161 ± 4.2 | 172 ± 7.8 |
| Sensitivity at 95% Specificity | 0.340 ± 0.23 | 0.342 ± 0.23 |

Figure 21A:
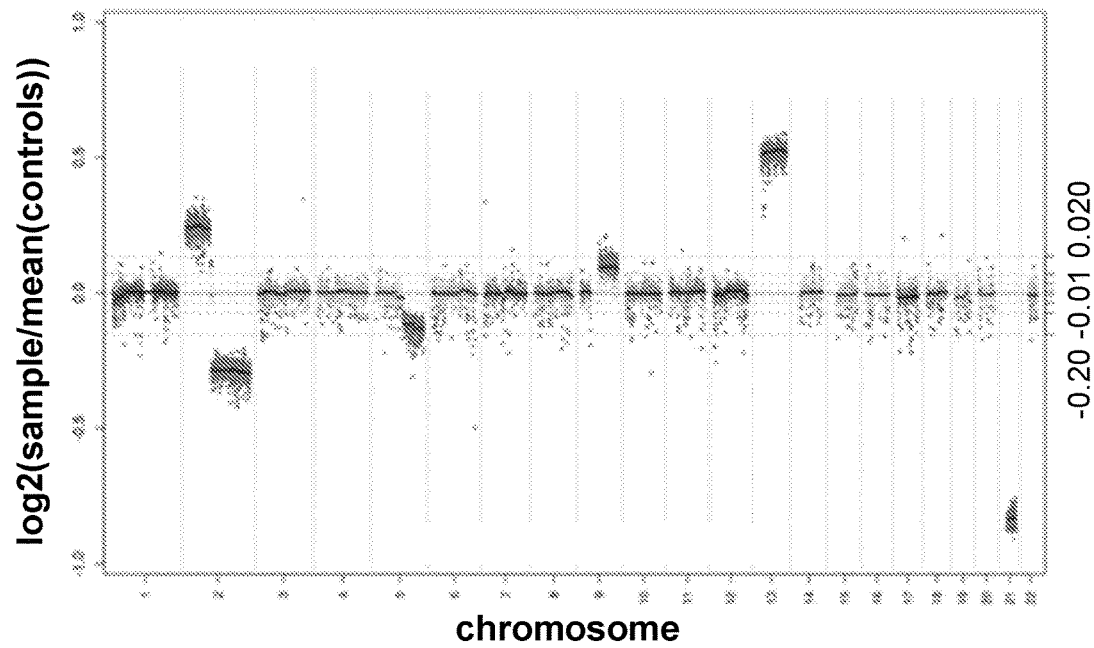
FIGS. 21A and 21B collectively illustrate an example of somatic copy number aberration detections in accordance with some embodiments of the present disclosure.
Figure 21B:
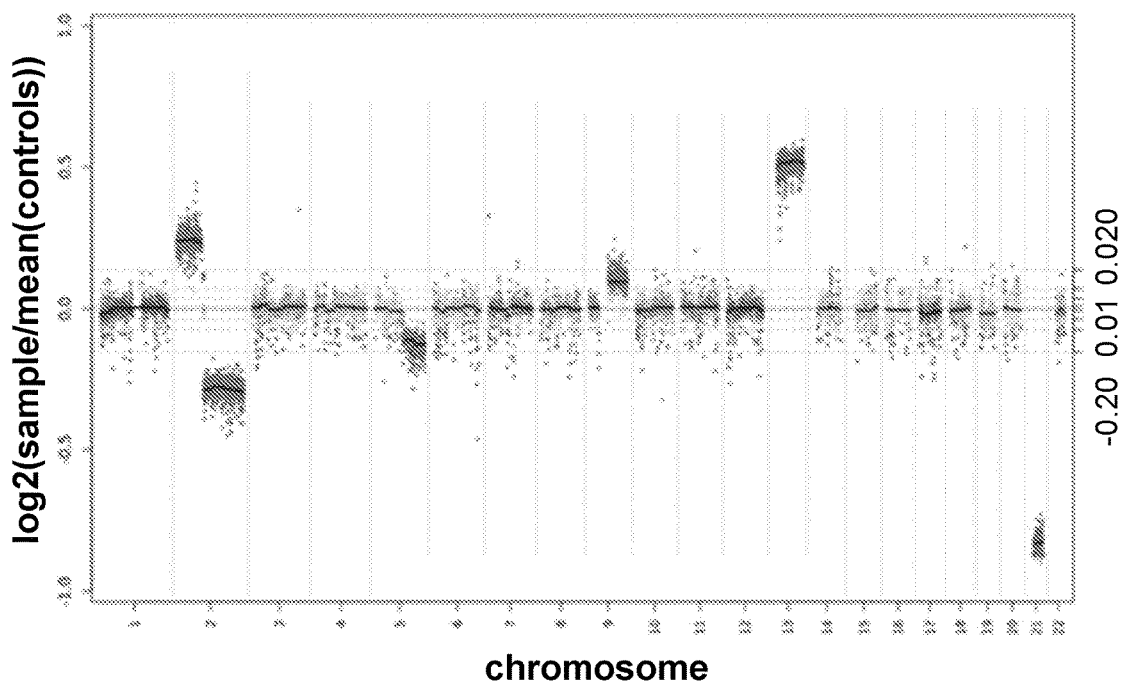

FIGS. 21A and 21B illustrate that SCNAs are detected similarly in WGBS and WGS data, respectively. These figures display SCNA plots for an individual patient (e.g., for a 44 year old female patient having Stage IV Cervical Cancer). The overall pattern of the SCNA plots is similar, with both data sets showing elevated SCNA counts for portions of chromosomes 2, 5, 9, 13, and 21. The location of each point in the y-axis represents the proportion of ctDNA in the patient showing gain or loss of one SCNA copy, where the x-axis represents positions in each respective chromosome. The mean absolute deviation for each data set was 0.027 and 0.029, respectively.

Both Z-score and B-score calculations further reinforce the similarity between these datasets. The mean base pair lengths of the SCNAs detected in WGBS vs. WGS (161±4.2 vs 172±7.8) are not significantly different but do hint that there might be some subtle differences in the sequences detected.

Figure 22:
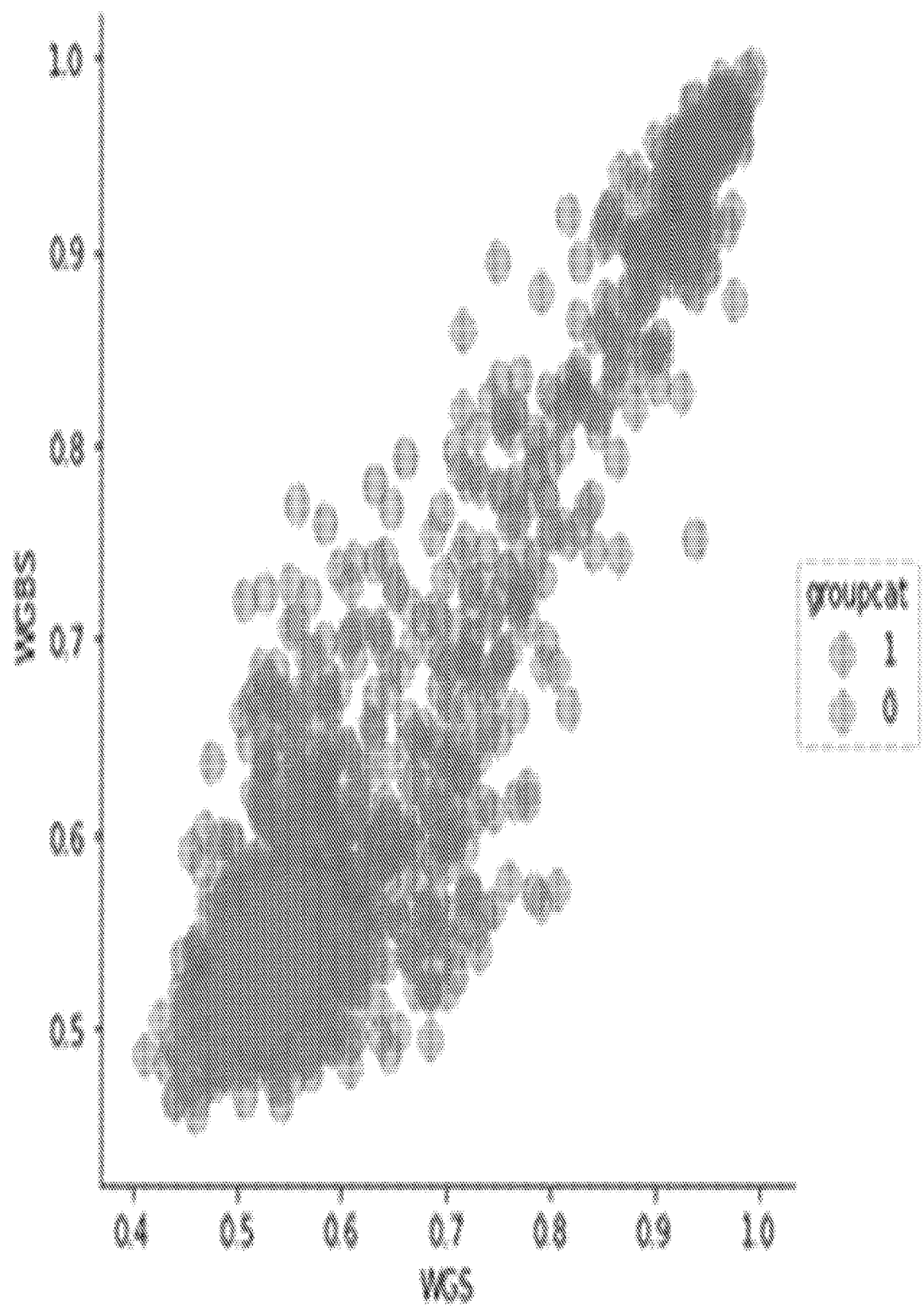
FIG. 22 illustrates similarities between whole genome sequencing and whole genome bisulfite sequencing detection of somatic copy number aberrations in accordance with some embodiments of the present disclosure.
Figure 23:
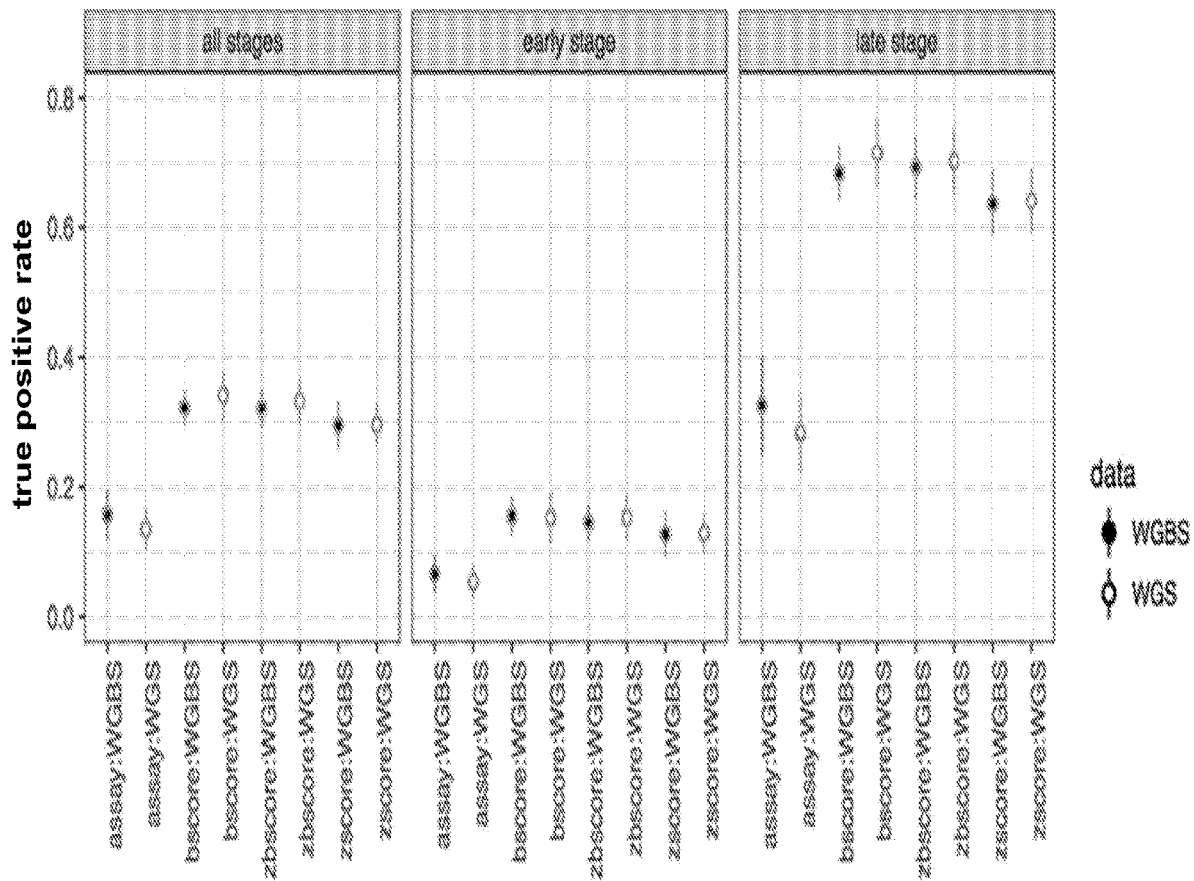
FIG. 23 illustrates true positive rates computed for patients at different stages of cancer using whole genome sequencing data and whole genome bisulfite sequencing data using different scoring models in accordance with some embodiments of the present disclosure.

FIG. 22 illustrates that WGSB and WGS true positive rates follow similar patterns. The similarity between these data sets holds across all cancer stages, as shown in FIG. 23. All true positive rates were calculated at 95% specificity levels. The true positive rates for each data type (WGBS vs WGS) are similar across the four metrics: assay (e.g., the average), B-score, Z-score, and combined Z/B-score. As is seen with other metrics, the true positive rate was elevated for patients with late stage cancer. These data demonstrate the similarity between WGBS and WGS data for detecting SCNAs (although, there appear to be some differences as well), and support the premise that both or either of these data types can be used for most such analyses. In particular, WGBS data can be analyzed for both SCNA signals and methylation status assessment and results from the analyses can be complimentary (e.g., FIGS. 10-13).

CONCLUSION

Plural instances may be provided for components, operations or structures described herein as a single instance. Finally, boundaries between various components, operations, and data stores are somewhat arbitrary, and particular operations are illustrated in the context of specific illustrative configurations. Other allocations of functionality are envisioned and may fall within the scope of the implementation(s). In general, structures and functionality presented as separate components in the example configurations may be implemented as a combined structure or component. Similarly, structures and functionality presented as a single component may be implemented as separate components. These and other variations, modifications, additions, and improvements fall within the scope of the implementation(s).

It will also be understood that, although the terms first, second, etc. may be used herein to describe various elements, these elements should not be limited by these terms. These terms are only used to distinguish one element from another. For example, a first subject could be termed a second subject, and, similarly, a second subject could be termed a first subject, without departing from the scope of the present disclosure. The first subject and the second subject are both subjects, but they are not the same subject.

The terminology used in the present disclosure is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting (the stated condition or event (" or "in response to detecting (the stated condition or event)," depending on the context.

The foregoing description included example systems, methods, techniques, instruction sequences, and computing machine program products that embody illustrative implementations. For purposes of explanation, numerous specific details were set forth in order to provide an understanding of various implementations of the inventive subject matter. It will be evident, however, to those skilled in the art that implementations of the inventive subject matter may be practiced without these specific details. In general, well-known instruction instances, protocols, structures and techniques have not been shown in detail.

The foregoing description, for purpose of explanation, has been described with reference to specific implementations. However, the illustrative discussions above are not intended to be exhaustive or to limit the implementations to the precise forms disclosed. Many modifications and variations are possible in view of the above teachings. The implementations were chosen and described in order to best explain the principles and their practical applications, to thereby enable others skilled in the art to best utilize the implementations and various implementations with various modifications as are suited to the particular use contemplated.

What is claimed is:

1. A method of training an untrained first classifier to classify a test subject of a given species to a cancer class in a plurality of cancer classes using a computer system comprising one or more processors, the method comprising:

obtaining, by the computer system and for each respective reference subject in a first plurality of reference subjects, (i) a cancer class of the respective reference subject and (ii) a sequencing construct for the respective reference subject that includes a first bin count for each respective bin in a plurality of bins that collectively represent all or a portion of a reference genome of the species, wherein each respective first bin count representative of a number of nucleic acid fragments measured from nucleic acids in a biological sample obtained from the respective reference subject that maps onto a different and non-overlapping portion of the reference genome of the species, wherein, for each respective cancer class in the plurality of cancer classes, the first plurality of reference subjects includes at least one reference subject that has the respective cancer class;

improving a computational efficiency of the computer system by collectively subjecting, by the computer system, the first bin count of each bin in the plurality of bins for each reference subject in the first plurality of reference subjects to a dimensionality reduction method thereby obtaining a feature set, wherein the feature set consists of a number of features that is fewer than the number of bins in the plurality of bins;

resampling, using the computer system, the feature set a plurality of times, wherein the resampling comprises forming, for each respective training iteration in a plurality of training iterations, a trained component classifier via:

omitting, from the feature set, a subset of values for features in the feature set for the first plurality of reference subjects; and forming the trained component classifier by inputting, in conjunction with the cancer class of respective reference subjects in the first plurality of reference subjects as ground truth, remaining values for the features in the feature set as collective input to a respective untrained component classifier; and constructing, as a result of the resampling and by collectively leveraging output generated by the trained component classifier formed in each of the plurality of training iterations, a trained first classifier having an improved cancer class recognition ability over the untrained first classifier.

2. The method of claim 1, wherein the sequencing construct for each respective reference subject in the first plurality of reference subjects is obtained by targeted panel or whole genome sequencing.

3. The method of claim 1, wherein each respective reference subject in the first plurality of reference subjects is human.

4. The method of claim 1, wherein the plurality of cancer classes is at least two or more cancer classes selected from the group consisting of non-cancer, bladder cancer, brain cancer, breast cancer, colorectal cancer, endometrial cancer, esophageal cancer, head/neck cancer, kidney cancer, liver cancer, hematological cancer, lung cancer, a lymphoma, leukemia, a melanoma, a lymphoma, ovarian cancer, pancreatic cancer, prostate cancer, rectal cancer, renal cancer, thyroid cancer and uterine cancer.

5. The method of claim 1, wherein:

the biological sample or methylation biological sample obtained from the respective reference subject is a whole blood sample from the respective reference subject, and the nucleic acids in the biological sample or methylation biological sample obtained from the respective reference subject are genomic DNA.

6. The method of claim 1, wherein:

the biological sample or methylation biological sample obtained from the respective reference subject is a plasma sample from the respective reference subject.

7. The method of claim 1, wherein the dimensionality reduction method further comprises application of principal component analysis using the cancer class and the sequencing construct of each reference subject in the first plurality of reference subjects thereby identifying the feature set comprising a plurality of principal components.

8. The method of claim 1, further comprising regularizing the first plurality of reference subjects set using the cancer class and the sequencing construct of each reference subject in the first plurality of reference subjects.

9. The method of claim 1, further comprising scaling the first bin count for each respective bin in the plurality of bins for each respective reference subject in the first plurality of reference subjects by:

taking a log transformation of the respective first bin count thereby forming a log transformed first bin count for the respective bin, subtracting a mean value of the respective log transformed first bin count across the first plurality of reference subjects from the log transformed first bin count of the respective bin thereby forming a first normalized first bin count for the respective bin; and dividing, subsequent to the subtracting, the respective first normalized first bin count for the respective bin by a standard deviation of the first normalized bin first count across the first plurality of reference subjects thereby scaling the first bin count for each respective bin in the plurality of bins for each respective reference subject in the first plurality of reference subjects.

10. The method of claim 1, further comprising estimating a performance of the first trained classifier as an average performance of the trained component classifier formed in each respective iteration in the plurality of training iterations.

11. The method of claim 1, wherein:

the sequencing construct for the respective reference subject further includes a second bin count for each respective bin in the plurality of bins, each respective second bin count representative of a number of nucleic acid fragments that are in a second size range that were measured from nucleic acids in the biological sample obtained from the respective reference subject that maps onto the different and non-overlapping portion of the reference genome, each respective first bin count representative of a number of nucleic acid fragments that are in a first size range that were measured from nucleic acids in the biological sample obtained from the respective reference subject that maps onto the different and non-overlapping portion of the reference genome, the collectively subjecting step further provides the second bin count of each bin in each respective plurality of bins across the first plurality of reference subjects to the dimensionality reduction method thereby obtaining the feature set, and the first size range is different than the second size range.

12. The method of claim 1, wherein:

the sequencing construct for the respective reference subject includes a respective set of bin counts for each respective bin in the plurality of bins, wherein the respective set of bin counts includes the first bin count, and wherein each respective bin count in the respective set of bin counts is representative of a number of nucleic acid fragments that are in a size range corresponding to the respective bin count that were measured from nucleic acids in the biological sample obtained from the respective reference subject that maps onto the different and non-overlapping portion of the reference genome, and the collectively subjecting step provides the respective set of bin counts of each bin in the plurality of bins across the first plurality of reference subjects to the dimensionality reduction method thereby obtaining the feature set, and wherein the respective set of bins includes at least three different bin counts, and wherein each bin count in the respective set of bin counts corresponds to a different size range.

13. A method of classifying a test subject of a given species to a cancer class in a plurality of cancer classes using a computer system comprising one or more processors, the method comprising:

using a trained first classifier to classify the test subject to a cancer class in the plurality of cancer classes using nucleic acid fragments in a biological sample obtained from the test subject, wherein the trained first classifier having been trained via:

obtaining, by the computer system and for each respective reference subject in a first plurality of reference subjects, (i) a cancer class of the respective reference subject and (ii) a sequencing construct for the respective reference subject that includes a first bin count for each respective bin in a plurality of bins that collectively represent all or a portion of a reference genome of the species, wherein each respective first bin count representative of a number of nucleic acid fragments measured from nucleic acids in a biological sample obtained from the respective reference subject that maps onto a different and non-overlapping portion of the reference genome of the species, wherein, for each respective cancer class in the plurality of cancer classes, the first plurality of reference subjects includes at least one reference subject that has the respective cancer class;

improving a computational efficiency of the computer system by collectively subjecting, by the computer system, the first bin count of each bin in the plurality of bins for each reference subject in the first plurality of reference subjects to a dimensionality reduction method thereby obtaining a feature set, wherein the feature set consists of a number of features that is fewer than the number of bins in the plurality of bins;

resampling, using the computer system, the feature set a plurality of times, wherein the resampling comprises forming, for each respective training iteration in a plurality of training iterations, a trained component classifier via:

omitting, from the feature set, a subset of values for features in the feature set for the first plurality of reference subjects; and forming the trained component classifier by inputting, in conjunction with the cancer class of respective reference subjects in the first plurality of reference subjects as ground truth, remaining values for the features in the feature set as collective input to a respective untrained component classifier; and constructing, as a result of the resampling and by collectively leveraging output generated by the trained component classifier formed in each of the plurality of training iterations, a trained first classifier having an improved cancer class recognition ability over the untrained first classifier.

14. The method of claim 13, wherein:

the using step combines a first call on cancer class made by the trained first classifier for the test subject with a second call made by a trained second classifier, input to the second trained classifier for the second call comprises a methylation pattern measured in a methylation biological sample obtained from the test subject, and the trained second classifier having been trained using a respective methylation pattern measured in a respective reference methylation biological sample from each reference subject in a second plurality of reference subjects.

15. The method of claim 14, wherein the test subject is deemed to have a first cancer class in the plurality of cancer classes when both the first call and the second call identify the test subject as having the same cancer class in the plurality of cancer classes.

16. The method of claim 14, wherein the test subject is deemed to have a first cancer class in the plurality of cancer classes when (i) the trained first classifier calls the first cancer class with a higher probability than all other cancer classes in the plurality of cancer classes and (ii) the second call identifies the test subject as having the first cancer class.

17. The method of claim 14, wherein the test subject is deemed to have a first cancer class in the plurality of cancer classes when (i) the first trained classifier calls the first cancer class with a call that is among the top two cancer classes in the plurality of cancer classes in terms of probability and (ii) the second call identifies the test subject as having the first cancer class.

18. The method of claim 14, wherein the test subject is deemed to have a first cancer class in the plurality of cancer classes when (i) the first trained classifier calls the first cancer class with a higher probability than all other cancer classes in the plurality of cancer classes and (ii) the second trained classifier calls the first cancer class with a higher probability than all other cancer classes in the plurality of cancer classes.

19. The method of claim 14, wherein the test subject is deemed to have a first cancer class in the plurality of cancer classes when (i) the first trained classifier calls the first cancer class with a call that is among the top two cancer classes in the plurality of cancer classes in terms of probability and (ii) the second trained classifier calls the first cancer class with a call that is among the top two cancer classes in the plurality of cancer classes in terms of probability.

20. The method of claim 14, wherein:

the biological sample obtained from the test subject is a plasma sample from the test subject, and the biological sample or the methylation biological sample obtained from the respective reference subject during the training was a plasma sample from the respective reference subject.

21. The method of claim 14, wherein:
the classifying uses the trained first classifier to classify the test subject to the cancer class in the plurality of cancer classes and an aggressiveness of the cancer class using (i) nucleic acid fragments of cell-free nucleic acids in the biological sample or the methylation biological sample obtained from the test subject and (ii) an indication of whether a predetermined genetic marker is absent or present in the test subject, and
the trained first classifier having been further trained such that:
the obtaining step further comprises, for each respective reference subject in the first plurality of reference subjects, an indication of whether the predetermined genetic marker is absent or present in the respective reference subject, and
the improving step further uses the indication of whether the predetermined genetic marker is absent or present in each respective reference subject in the first plurality of reference subjects as ground truth.

22. The method of claim 13, wherein:
the trained first classifier is a multinomial classifier that provides a plurality of likelihoods responsive to the nucleic acid fragments obtained from cell-free nucleic acids from the test subject, wherein each respective likelihood in the plurality of likelihoods is a likelihood that the test subject has a corresponding cancer class in the plurality of cancer classes.

23. The method of claim 13, further comprising:
identifying a recommended treatment to the test subject based upon the cancer class of the test subject determined by the first trained classifier.

24. The method of claim 13, further comprising:
identifying a recommended first treatment to the test subject when the first trained classifier determines that the test subject has a first cancer, and
identifying a recommended second treatment to the test subject when the first trained classifier determines that the test subject has a second cancer, wherein
the first cancer and the second cancer are different cancers.

25. The method of claim 24, wherein the first cancer and the second cancer are each independently selected from the group consisting of bladder cancer, brain cancer, breast cancer, colorectal cancer, endometrial cancer, esophageal cancer, head/neck cancer, kidney cancer, liver cancer, hematological cancer, lung cancer, a lymphoma, leukemia, a melanoma, a lymphoma, ovarian cancer, pancreatic cancer, prostate cancer, rectal cancer, renal cancer, thyroid cancer and uterine cancer.

26. A computer system comprising:
one or more processors; and
a non-transitory computer-readable medium including one or more sequences of instructions that, when executed by the one or more processors, cause the one or more processors to perform a method of training an untrained first classifier to classify a test subject of a given species to a cancer class in a plurality of cancer classes, the method comprising:
obtaining, by the computer system and for each respective reference subject in a first plurality of reference subjects, (i) a cancer class of the respective reference subject and (ii) a sequencing construct for the respective reference subject that includes a first bin count for each respective bin in a plurality of bins that collectively represent all or a portion of a reference genome of the species, wherein each respective first bin count representative of a number of nucleic acid fragments measured from nucleic acids in a biological sample obtained from the respective reference subject that maps onto a different and non-overlapping portion of the reference genome of the species, wherein, for each respective cancer class in the plurality of cancer classes, the first plurality of reference subjects includes at least one reference subject that has the respective cancer class;
improving a computational efficiency of the computer system by collectively subjecting, by the computer system, the first bin count of each bin in the plurality of bins for each reference subject in the first plurality of reference subjects to a dimensionality reduction method thereby obtaining a feature set, wherein the feature set consists of a number of features that is fewer than the number of bins in the plurality of bins;
resampling, using the computer system, the feature set a plurality of times, wherein the resampling comprises forming, for each respective training iteration in a plurality of training iterations, a trained component classifier via:
omitting, from the feature set, a subset of values for features in the feature set for the first plurality of reference subjects; and
forming the trained component classifier by inputting, in conjunction with the cancer class of respective reference subjects in the first plurality of reference subjects as ground truth, remaining values for the features in the feature set as collective input to a respective untrained component classifier; and
constructing, as a result of the resampling and by collectively leveraging output generated by the trained component classifier formed in each of the plurality of training iterations, a trained first classifier having an improved cancer class recognition ability over the untrained first classifier.

27. A computer system, comprising:
one or more processors; and
a non-transitory computer-readable medium including one or more sequences of instructions that, when executed by the one or more processors, cause the one or more processors to perform a method of classifying a test subject of a given species to a cancer class in a plurality of cancer classes, the method comprising:
using a trained first classifier to classify the test subject to a cancer class in the plurality of cancer classes using nucleic acid fragments in a biological sample obtained from the test subject, the trained first classifier having been trained via:
obtaining, by the computer system and for each respective reference subject in a first plurality of reference subjects, (i) a cancer class of the respective reference subject and (ii) a sequencing construct for the respective reference subject that includes a first bin count for each respective bin in a plurality of bins that collectively represent all or a portion of a reference genome of the species, wherein each respective first bin count representative of a number of nucleic acid fragments measured from nucleic acids in a biological sample obtained from the respective reference subject that maps onto a different and non-overlapping portion of the reference genome of the species, wherein, for each respective cancer class in the plurality of cancer classes, the first plurality of reference subjects includes at least one reference subject that has the respective cancer class;

improving a computational efficiency of the computer system by collectively subjecting, by the computer system, the first bin count of each bin in the plurality of bins for each reference subject in the first plurality of reference subjects to a dimensionality reduction method thereby obtaining a feature set, wherein the feature set consists of a number of features that is fewer than the number of bins in the plurality of bins;

resampling, using the computer system, the feature set a plurality of times, wherein the resampling comprises forming, for each respective training iteration in a plurality of training iterations, a trained component classifier via:

omitting, from the feature set, a subset of values for features in the feature set for the first plurality of reference subjects; and forming the trained component classifier by inputting, in conjunction with the cancer class of respective reference subjects in the first plurality of reference subjects as ground truth, remaining values for the features in the feature set as collective input to a respective untrained component classifier; and constructing, as a result of the resampling and by collectively leveraging output generated by the trained component classifier formed in each of the plurality of training iterations, a trained first classifier having an improved cancer class recognition ability over the untrained first classifier.

* * * * *